United States Patent
Dong et al.

(10) Patent No.: US 11,084,852 B2
(45) Date of Patent: Aug. 10, 2021

(54) UBIQUITIN INTERACTING MOTIF PEPTIDES AS THERAPEUTICS

(71) Applicant: OKLAHOMA MEDICAL RESEARCH FOUNDATION, Oklahoma City, OK (US)

(72) Inventors: Yunzhou Dong, Oklahoma City, OK (US); Hong Chen, Oklahoma City, OK (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 0 days.

(21) Appl. No.: 15/736,022

(22) PCT Filed: Jun. 8, 2016

(86) PCT No.: PCT/US2016/036308
§ 371 (c)(1),
(2) Date: Dec. 13, 2017

(87) PCT Pub. No.: WO2016/205027
PCT Pub. Date: Dec. 22, 2016

(65) Prior Publication Data
US 2018/0305423 A1 Oct. 25, 2018

Related U.S. Application Data

(60) Provisional application No. 62/175,801, filed on Jun. 15, 2015.

(51) Int. Cl.
*C07K 14/47* (2006.01)
*A61K 38/00* (2006.01)
*A61P 9/10* (2006.01)
*C12N 15/62* (2006.01)
*A61P 35/00* (2006.01)

(52) U.S. Cl.
CPC .......... *C07K 14/4702* (2013.01); *A61K 38/00* (2013.01); *A61P 9/10* (2018.01); *C12N 15/625* (2013.01); *A61P 35/00* (2018.01); *C07K 2319/033* (2013.01); *C07K 2319/035* (2013.01); *C07K 2319/95* (2013.01)

(58) Field of Classification Search
None
See application file for complete search history.

(56) References Cited

U.S. PATENT DOCUMENTS

| 6,342,379 B1 | 1/2002 | Tsien et al. |
| 8,367,621 B2 | 2/2013 | Ruoslahti et al. |
| 2012/0197059 A1 | 8/2012 | Dong et al. |
| 2014/0010861 A1 | 1/2014 | Bancel et al. |

OTHER PUBLICATIONS

Coon et al., "Epsins' novel role in cancer cell invasion," *Commun Integr. Biol.*, 4(1):95-7, 2011.
Dong et al., "Peptide Mimetic of Epsin Ubiquitin-interacting Motif Designed to Disable VEGF Receptor 2 Endocytosis and Promote Non-functional Angiogenesis in Vivo," Abstract #5 presented at Targeting VEGF-Mediated Tumor Angiogenesis in Cancer Therapy Meeting of the New York Academy of Sciences, Jun. 19, 2014.
Pasula et al., "Endothelial epsin deficiency decreases tumor growth by enhancing VEGF signaling," *The Journal of Clinical Investigation*, 122(12): 4424-38, 2012.
PCT International Search Report and Written Opinion issued in International Application No. PCT/US2016/036308, dated Nov. 15, 2016.
PCT Invitation to Pay Additional Fees issued in International Application No. PCT/US2016/036308, dated Sep. 12, 2016.
Sugahara et al., "Coadministration of a tumor-penetrating peptide enhances the efficacy of cancer drugs," *Science*, 328(5981):1031-5, 2010.
Sugahara et al., "Tissue-penetrating delivery of compounds and nanoparticles into tumors," *Cancer Cell*, 16(6):510-20, 2009.
Svensen et al., "Peptides for cell-selective drug delivery" *Trends Pharmological Sci.*, 33(4): 186-192, 2012.
Tessneer et al., "Endocytic Adaptor Protein Epsin Is Elevated in Prostate Cancer and Required for Cancer Progression," *ISRN Oncology*, vol. 2013, 8 pages, 2013.
Tessneer et al., "Epsin Family of Endocytic Adaptor Proteins as Oncogenic Regulators of Cancer Progression," *J. Can. Res. Updates*, 2(3):144-150, 2013.
Uniprot Q9Y6I3, "EPN1_HUMAN," Apr. 29, 2015. Retrieved from the Internet at http://www.uniprot.org/uniprot/Q9Y6I3.txt?version=143 on Aug. 22, 2016.

*Primary Examiner* — Christina Bradley
(74) *Attorney, Agent, or Firm* — Wolf, Greenfield & Sacks, P.C.

(57) ABSTRACT

The present disclosure describes the use peptides of comprising ubiquitin interacting motifs (UIMs) alone or in combination with other agents to treat conditions such as cancer, atherosclerosis and obesity.

14 Claims, 47 Drawing Sheets

Specification includes a Sequence Listing.

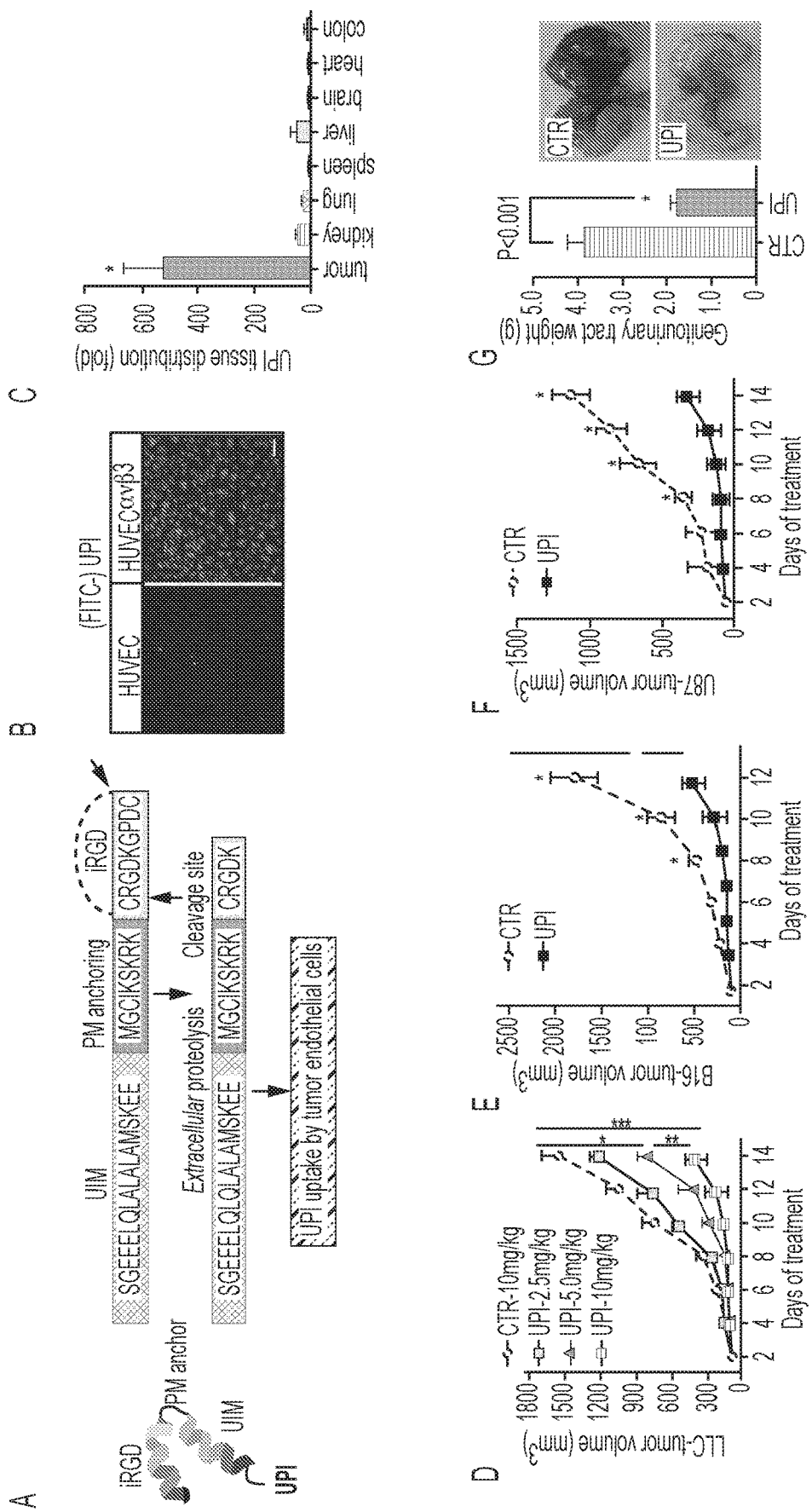
FIGS. 1A-G

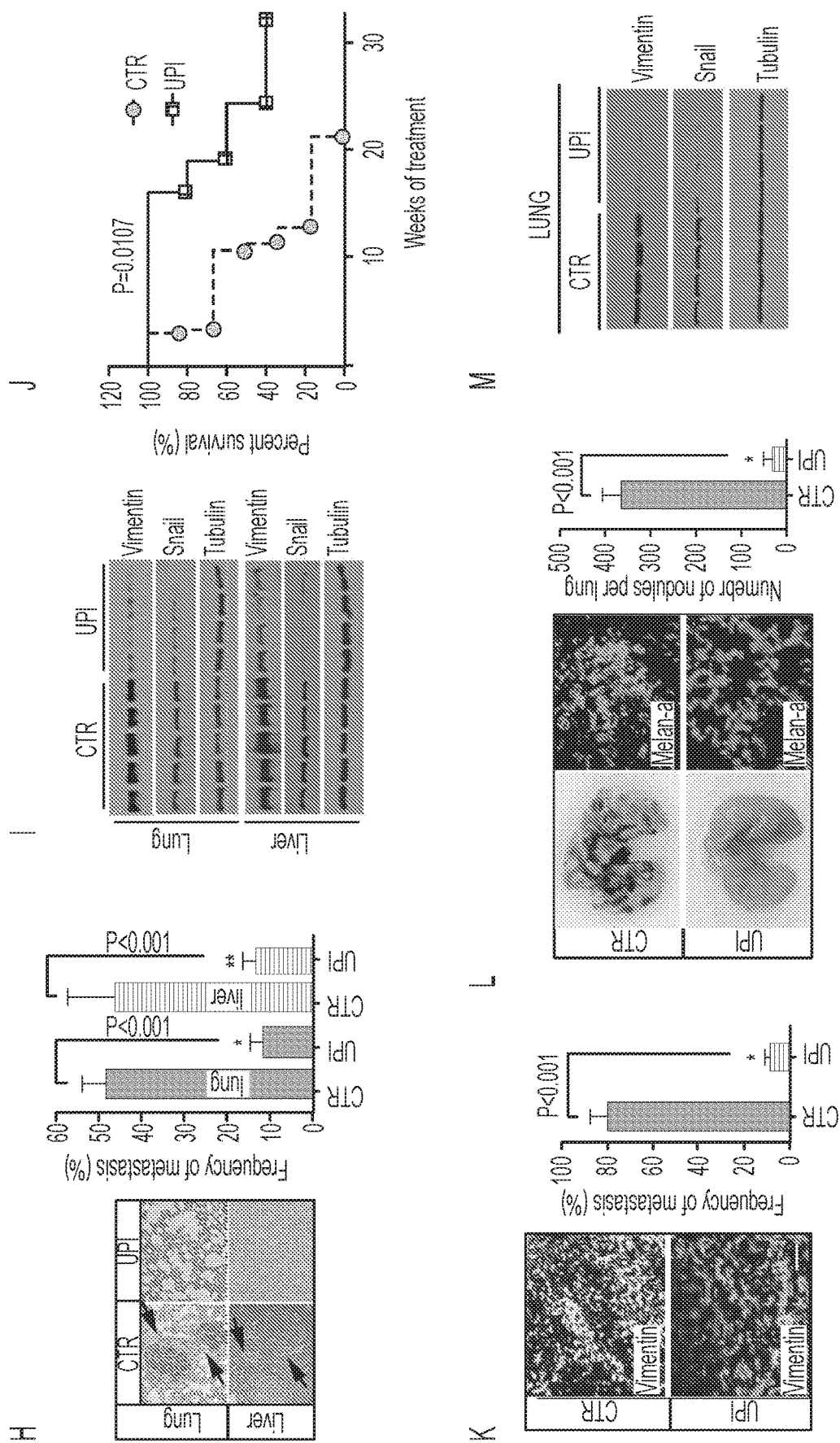
FIGS. 1H-M

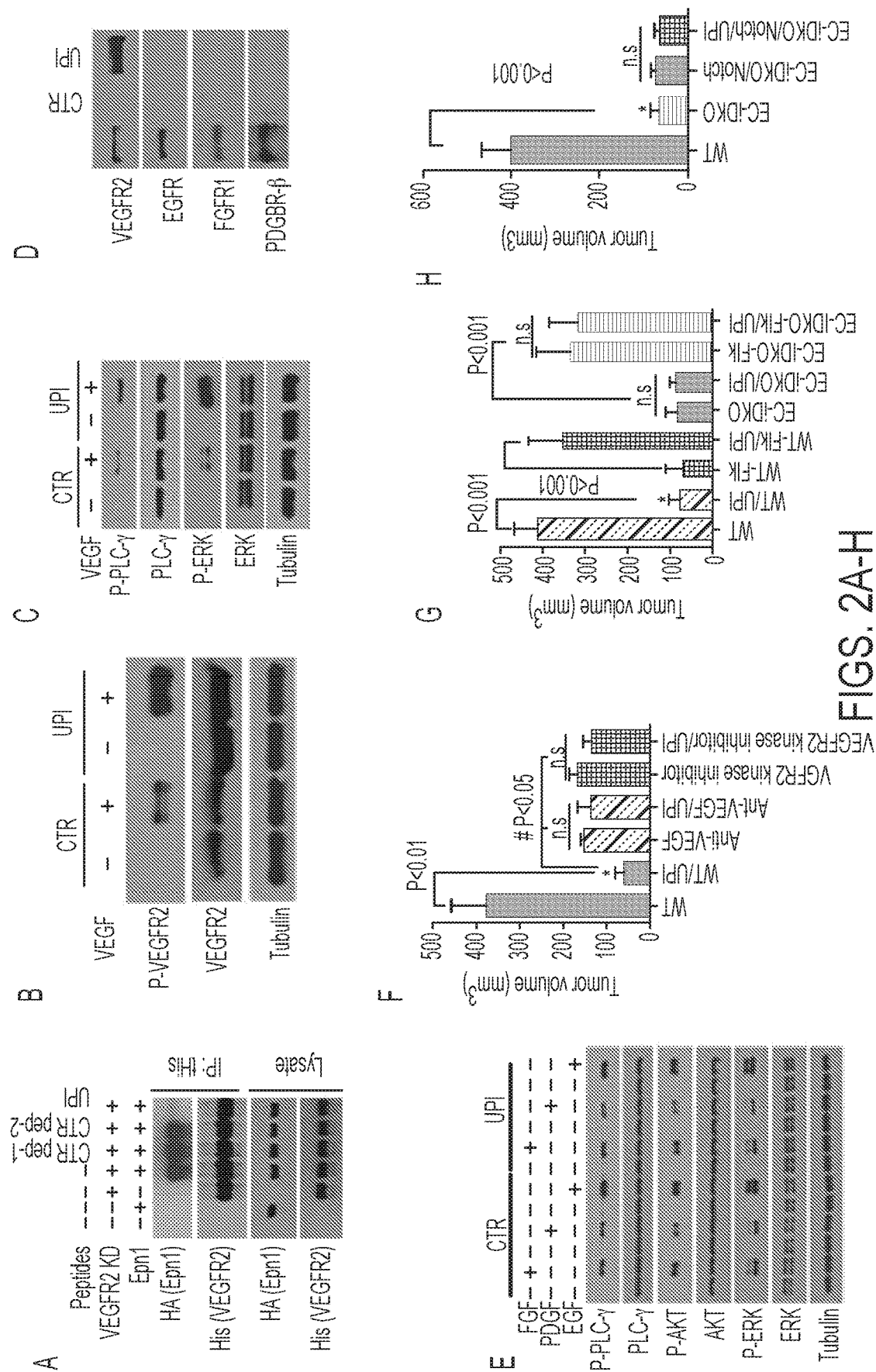
FIGS. 2A-H

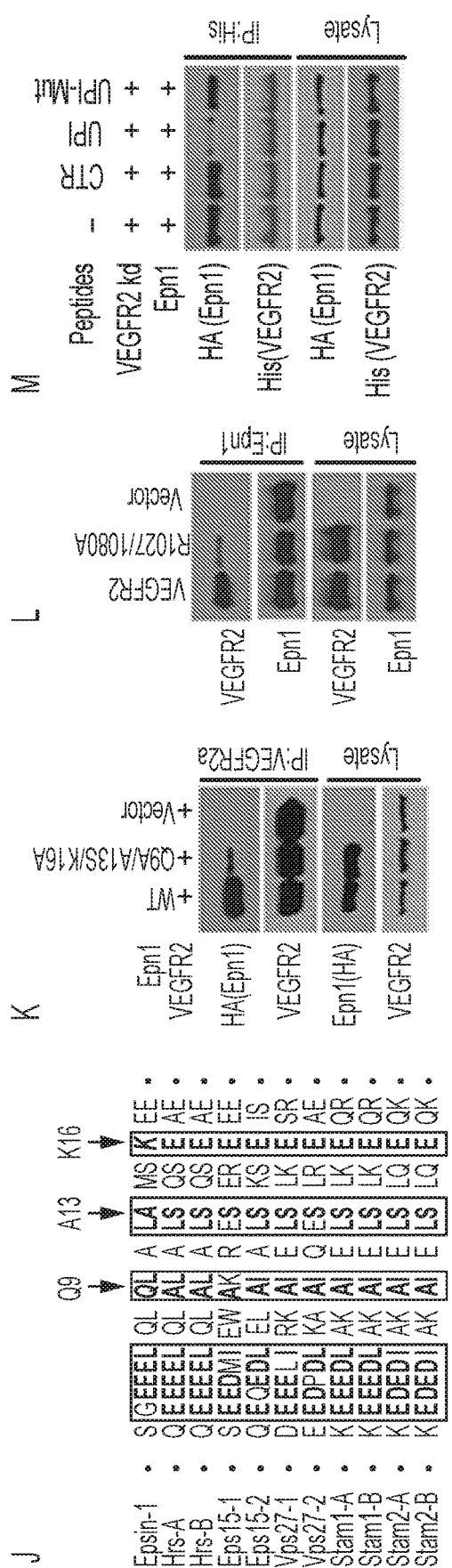
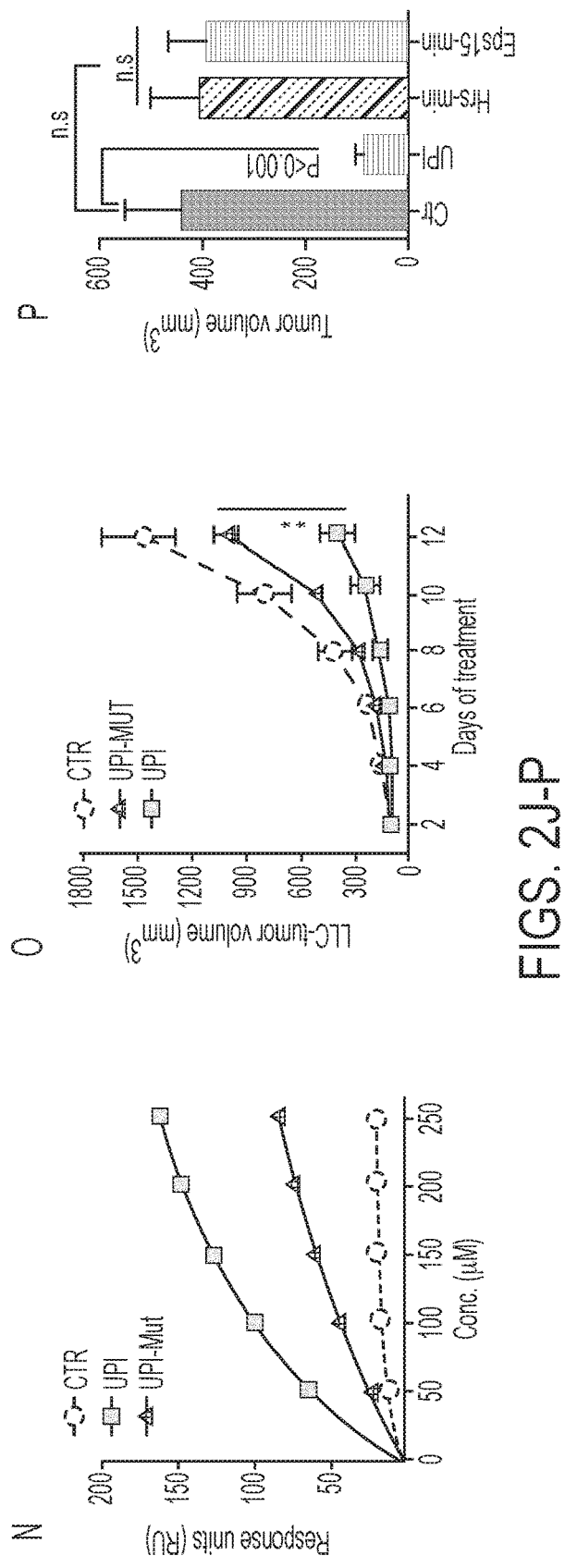
FIGS. 2J-P

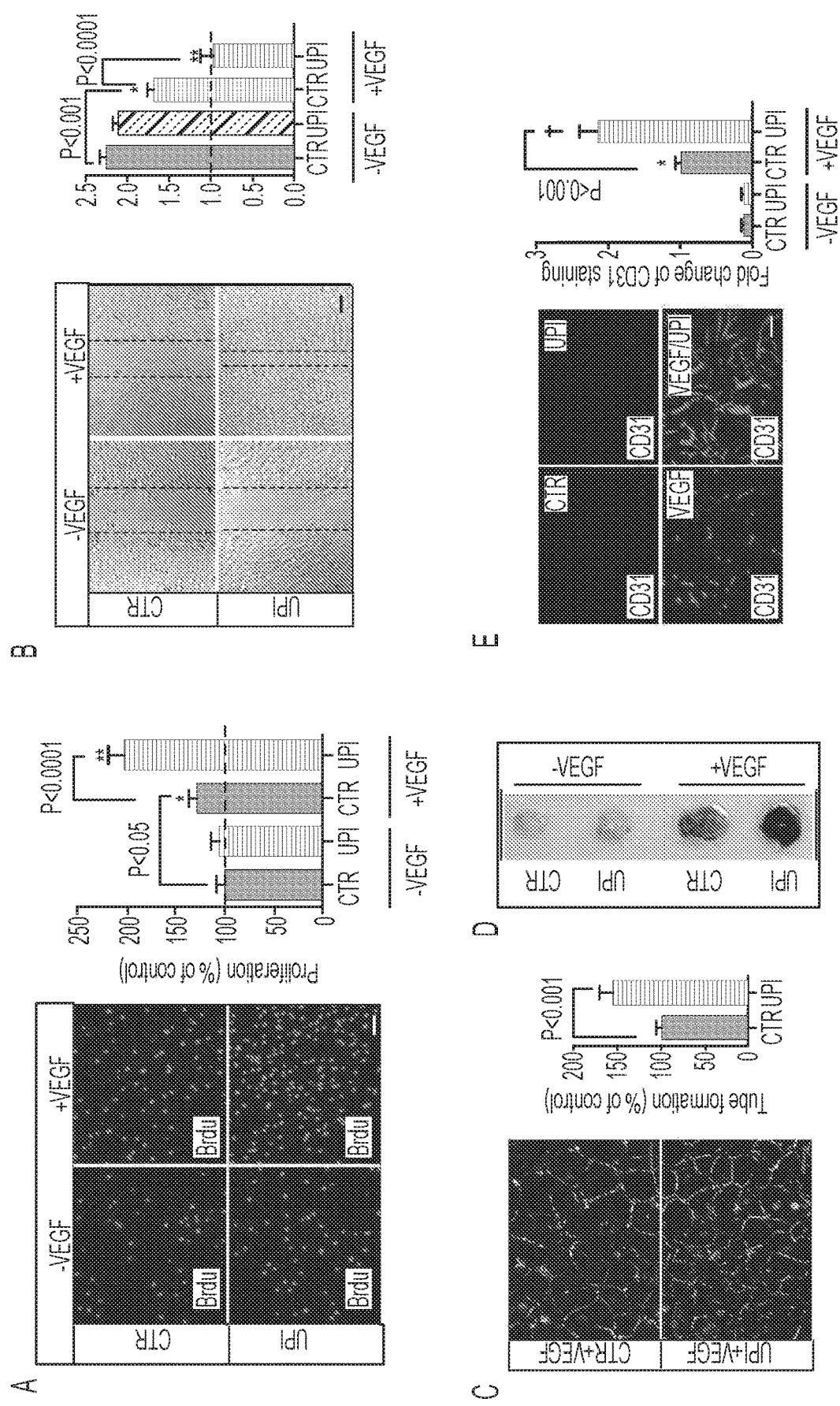
FIGS. 3A-E

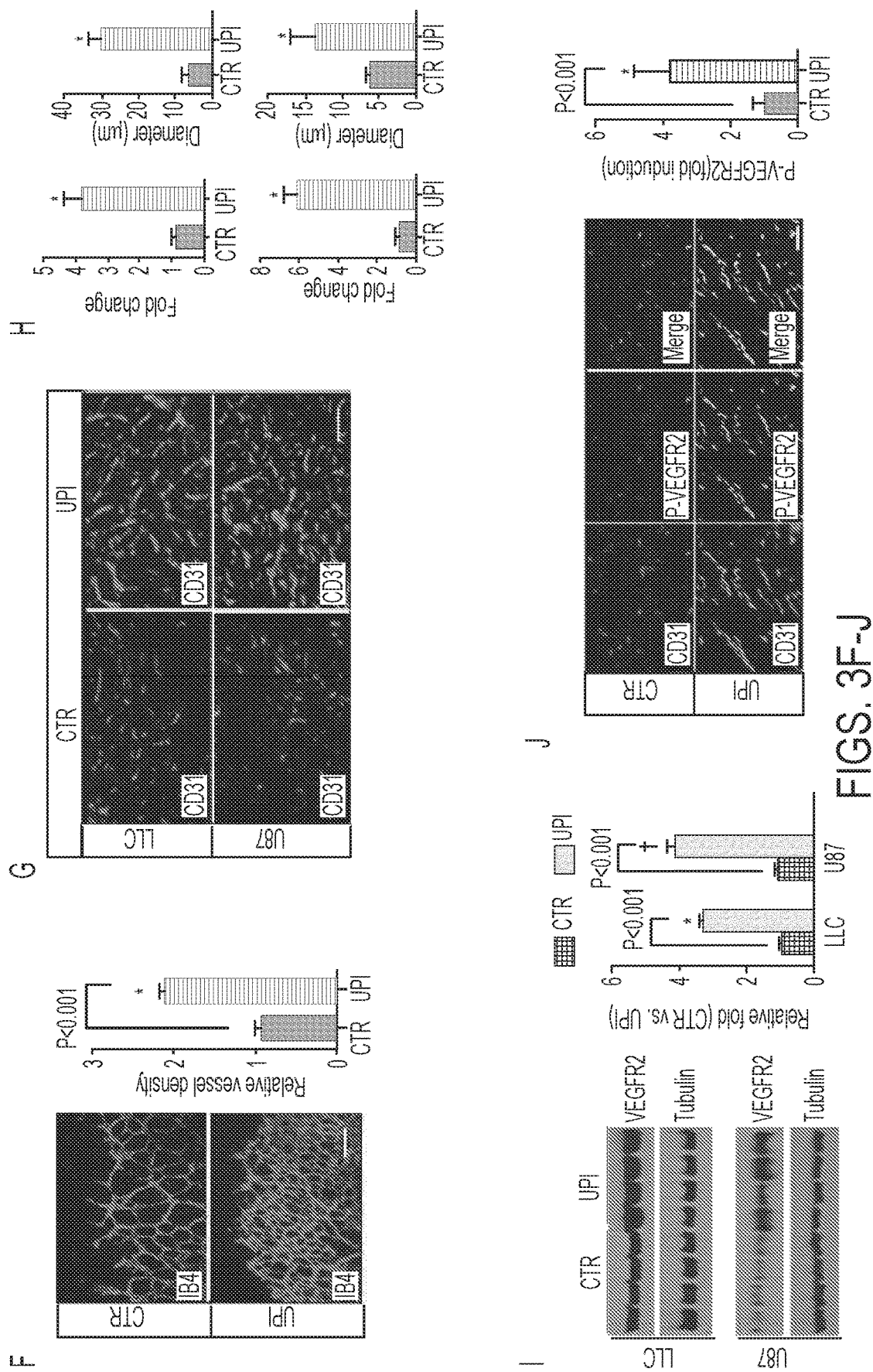
FIGS. 3F-J

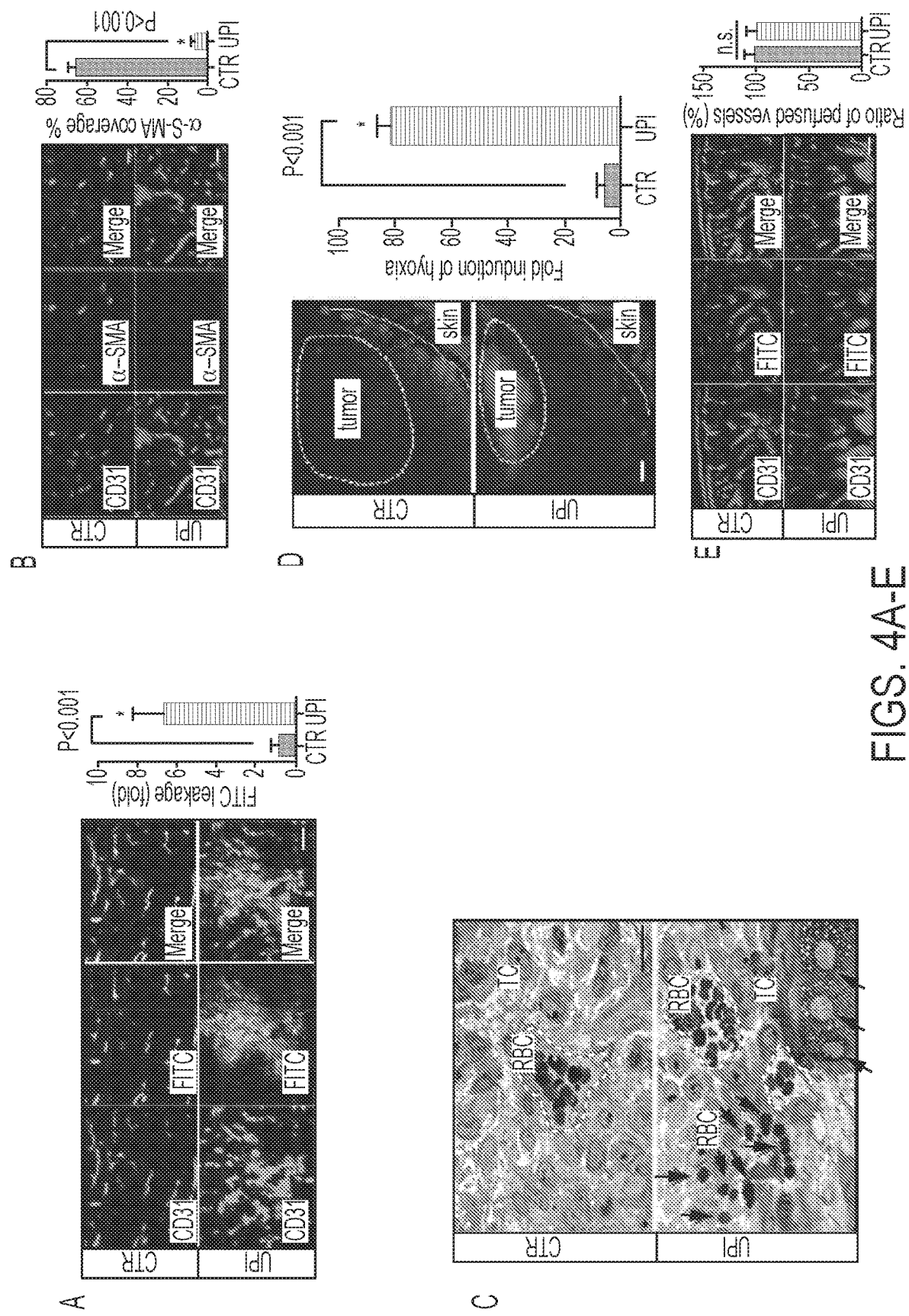
FIGS. 4A-E

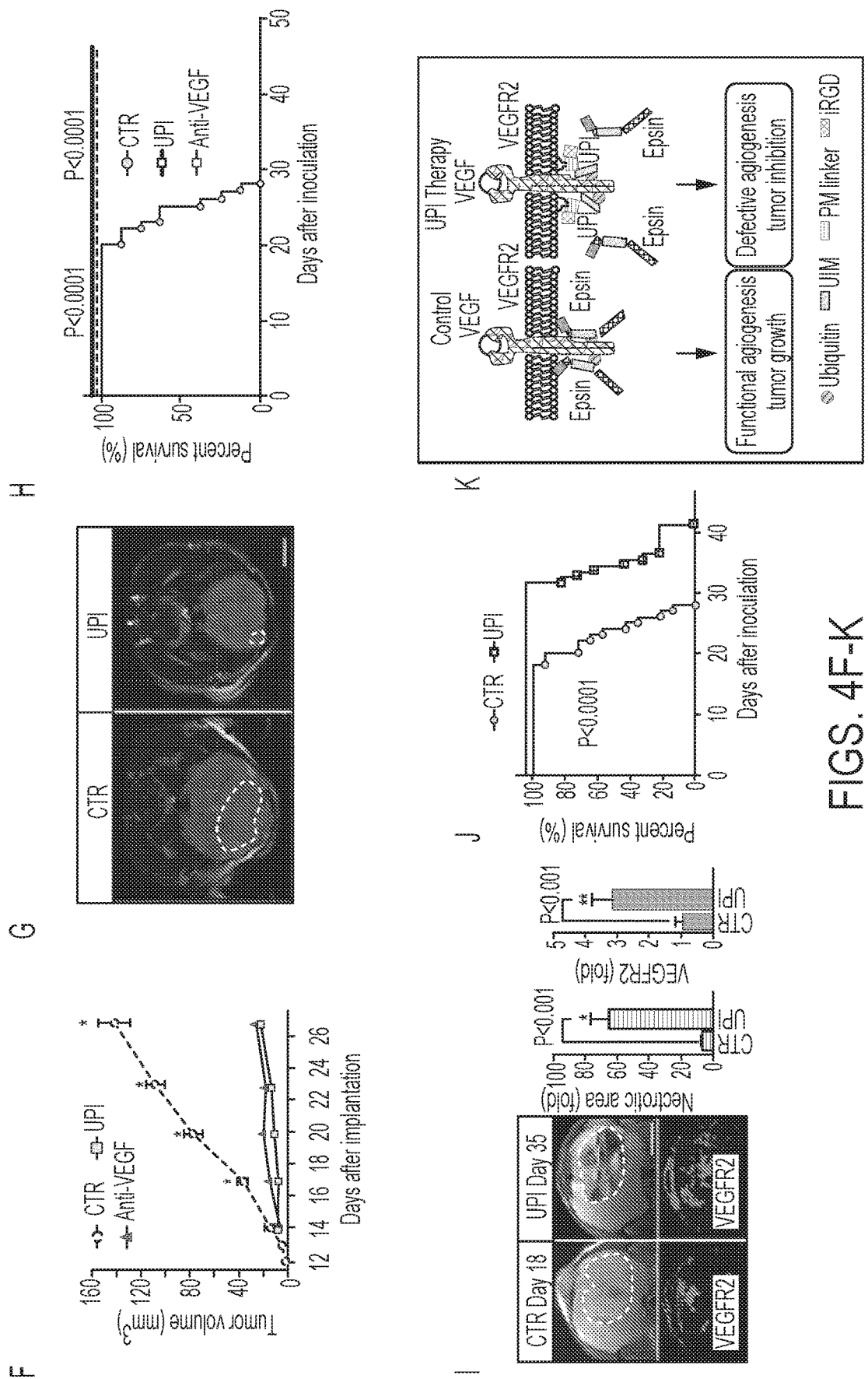
FIGS. 4F-K

A
```
                     1         10
                     .         .
    hEpsin1-UIM    SGEEELQLQLALAMSKEE..............
    mEpsin1-UIM    SGEEELQLQLALAMSKEE..............
    hEpsin2-UIM    SGEEELQLQLALAMSREV..............
    mEpsin2-UIM    SGEEELQLQLALAMSREV..............
    yVps27-UIM     ..EEEE-IRKAIELSLKE..............
    UPI_peptide    SGEEELQLQLALAMSKEEMGCIKSKRKCRGDK
```
B
  
Yeast Vps27 UIM | Model of epsin UIM | Model of UPI peptide
C
  
Yeast Vps27 UIM-Ub | Model of human epsin UIM-Ub | Model of synsthetic peptide UPI-Ub
D
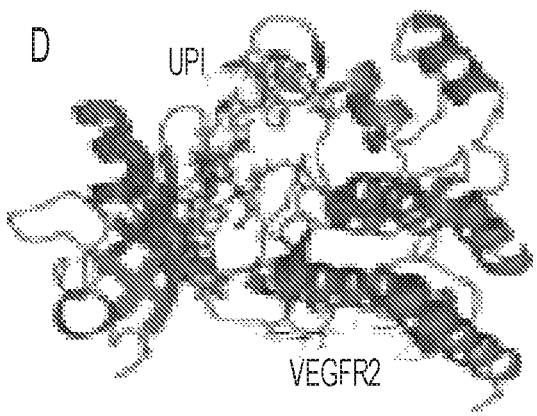 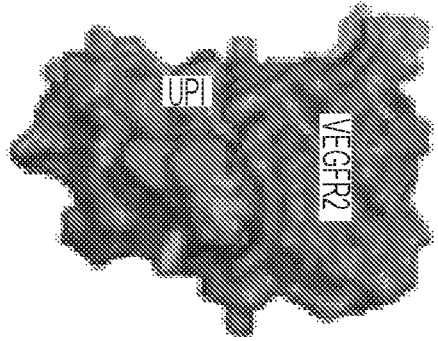
FIGS. 5A-D

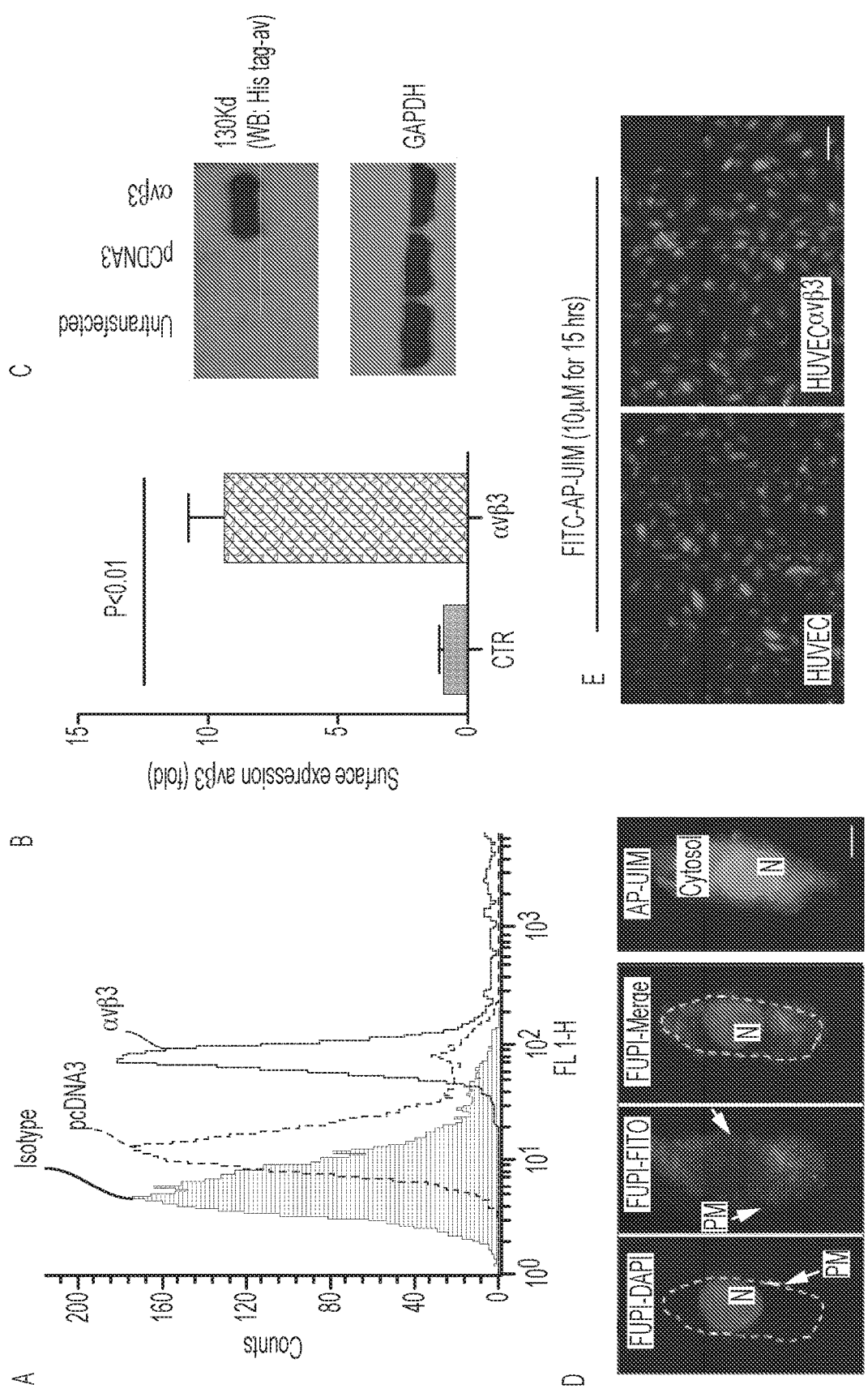
FIGS. 6A-E

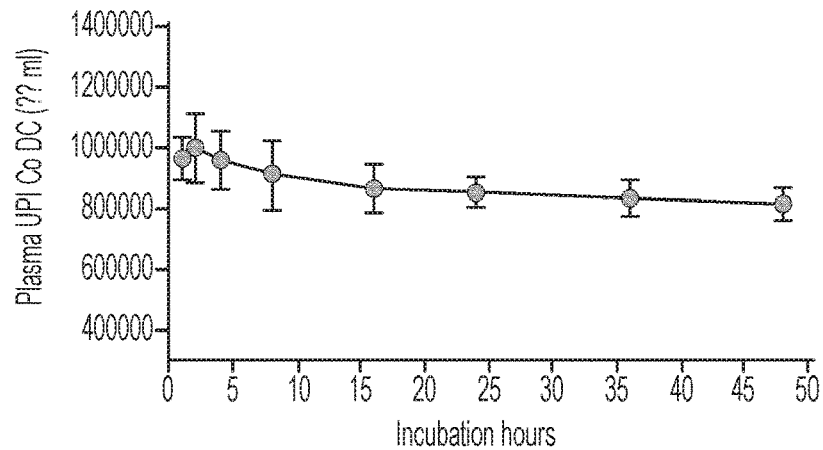
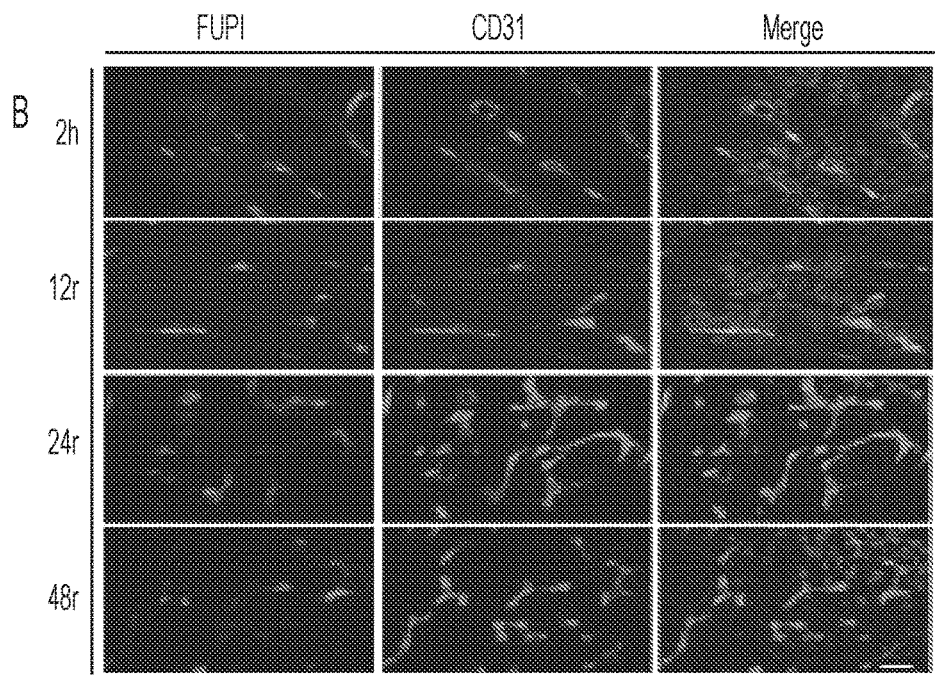
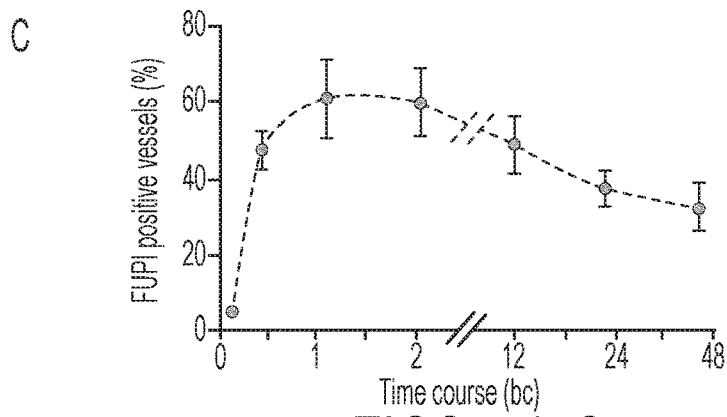
FIGS. 7A-C

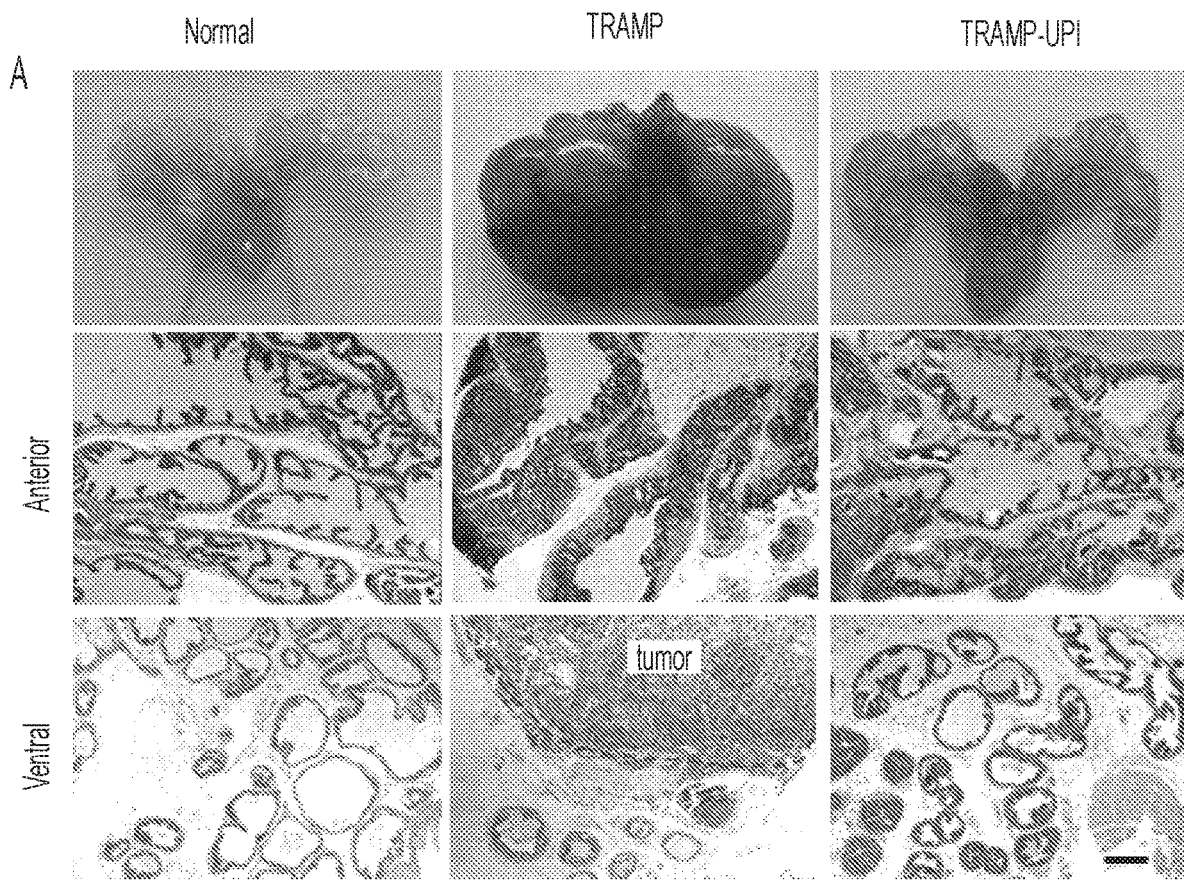
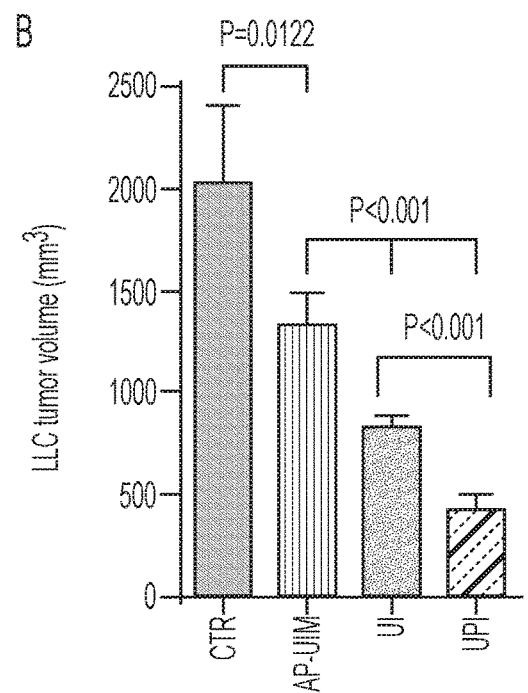
FIGS. 9A-B

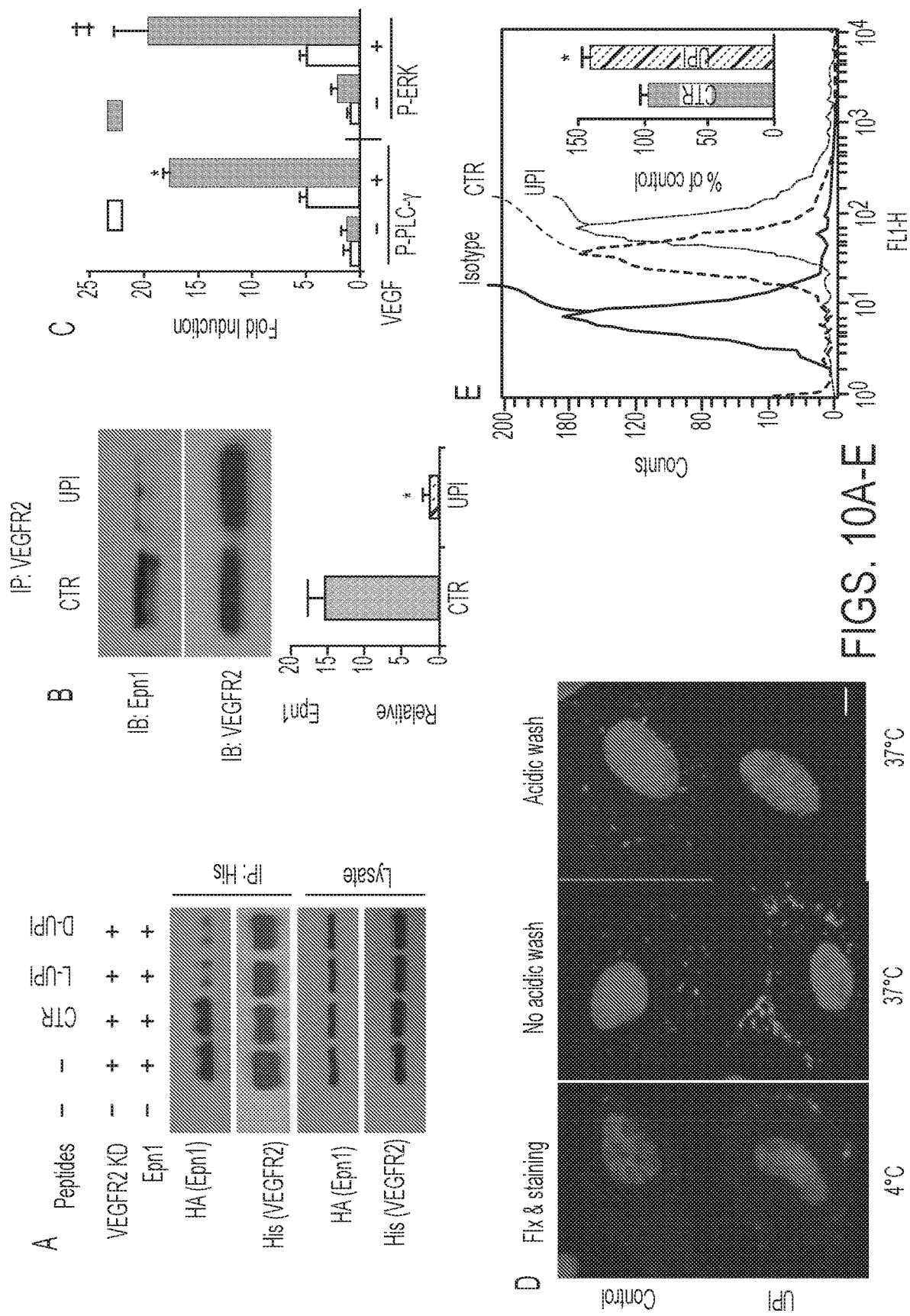
FIGS. 10A-E

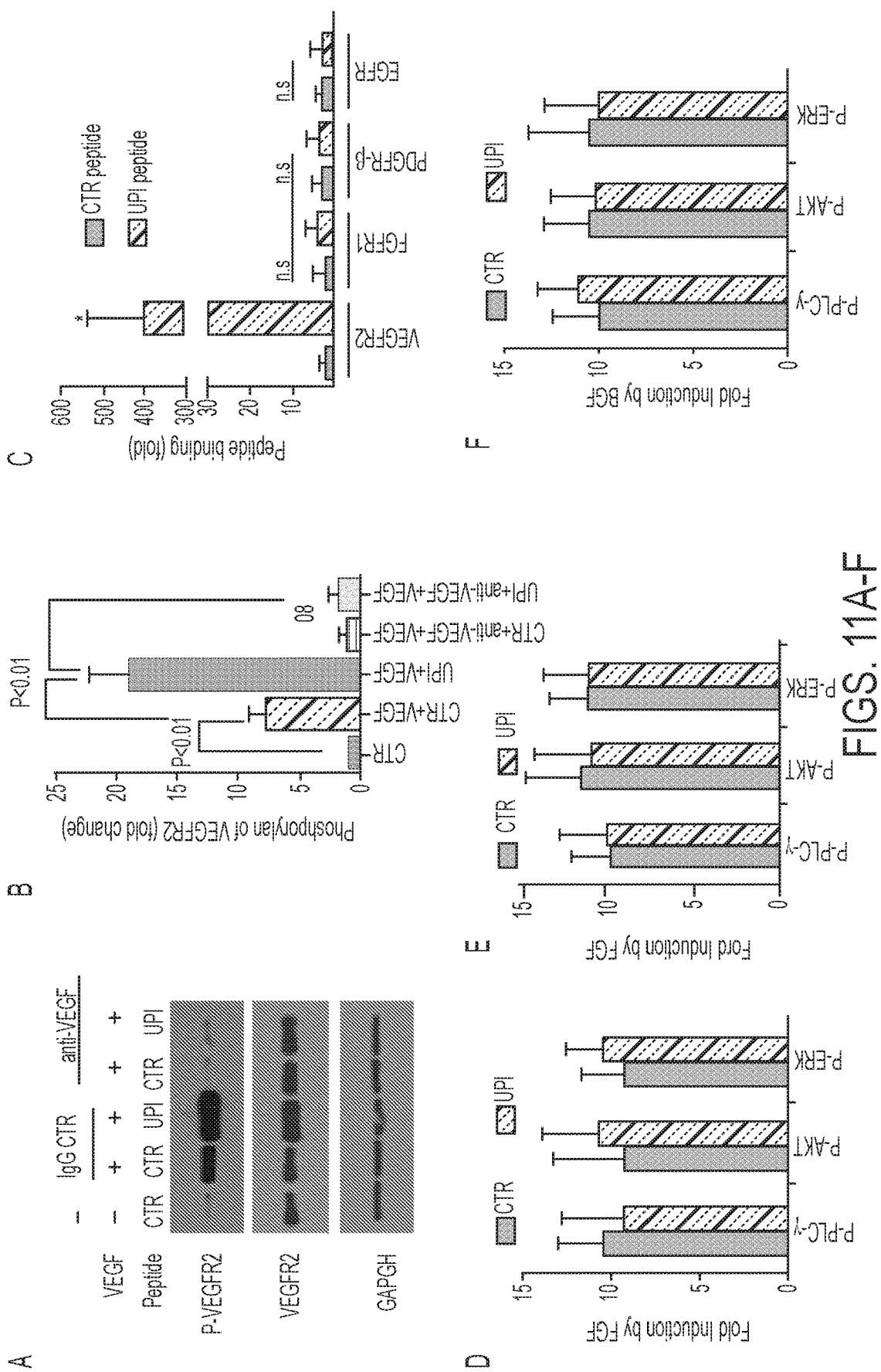
FIGS. 11A-F

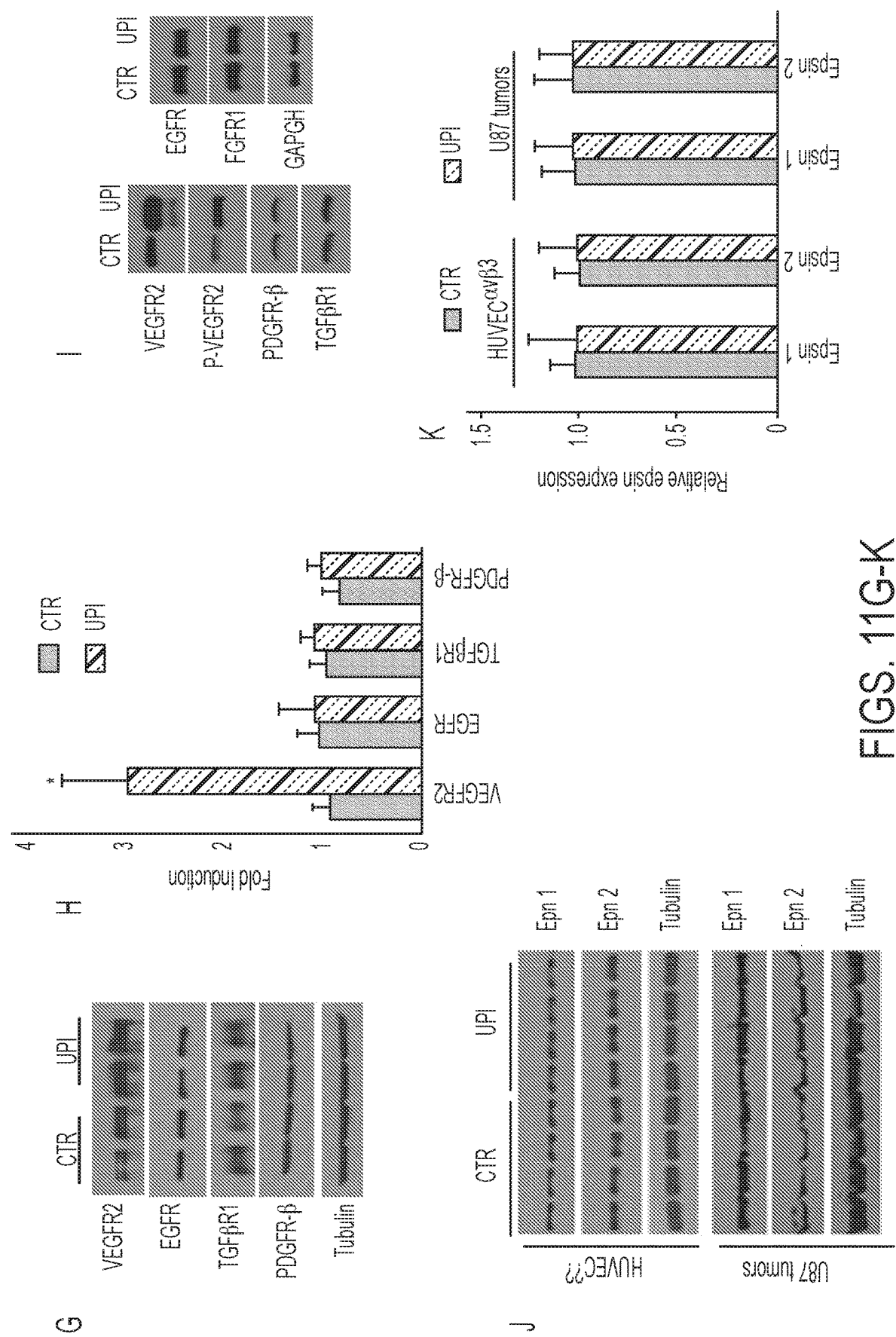
FIGS. 11G-K

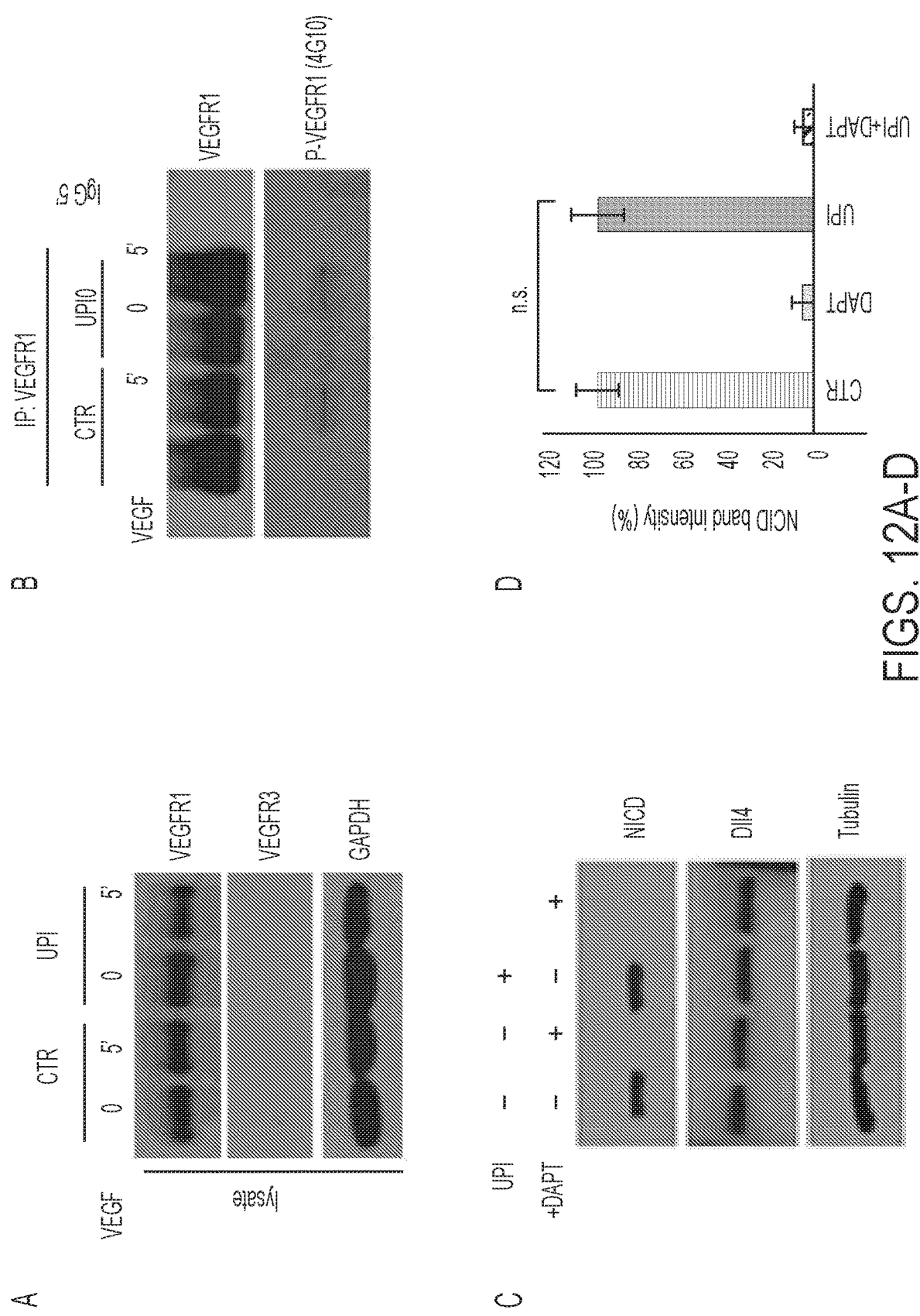
FIGS. 12A-D

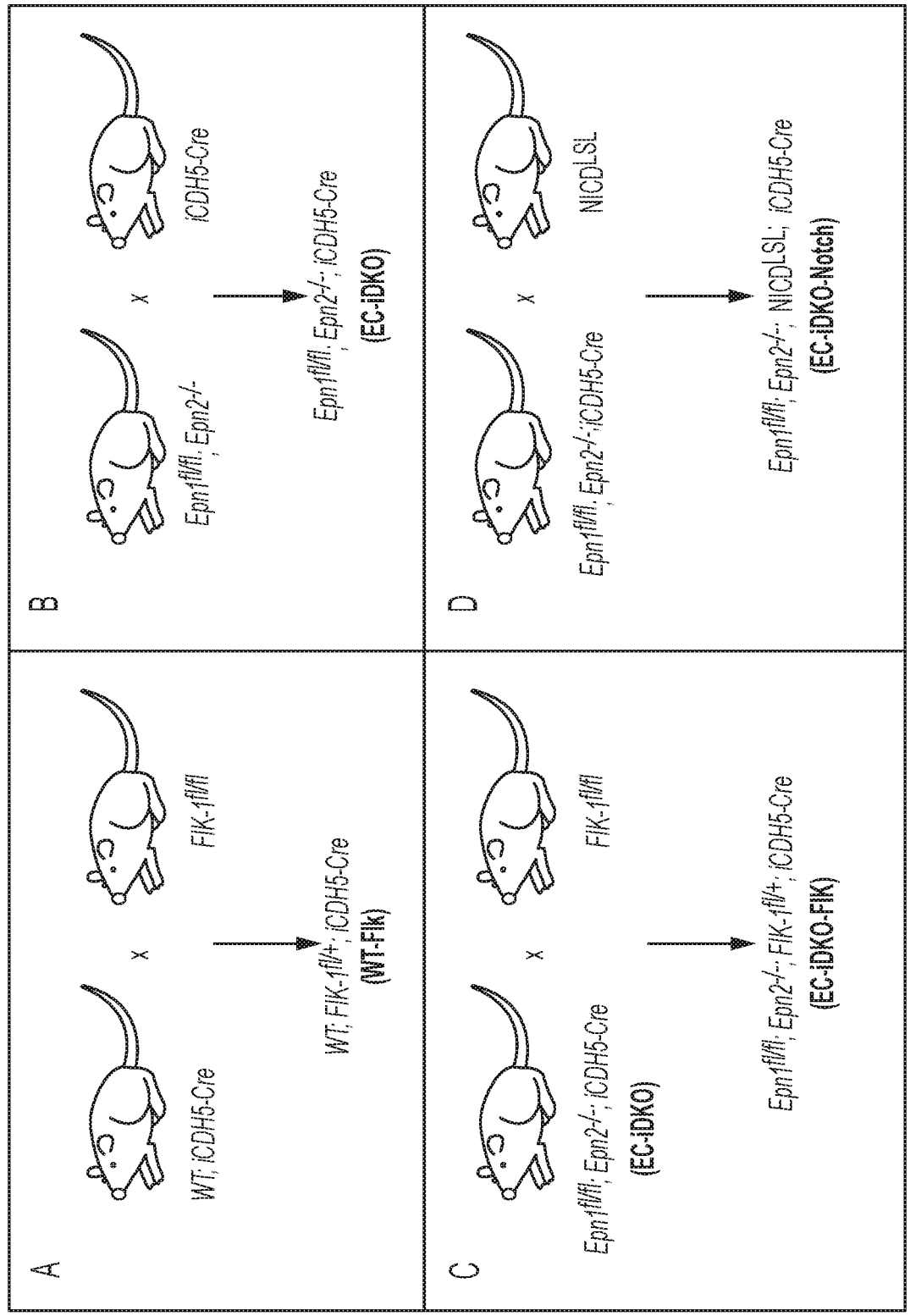
FIGS. 13A-D

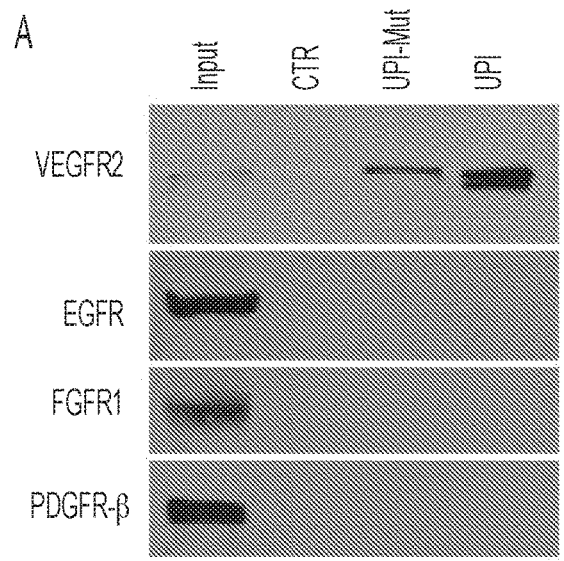
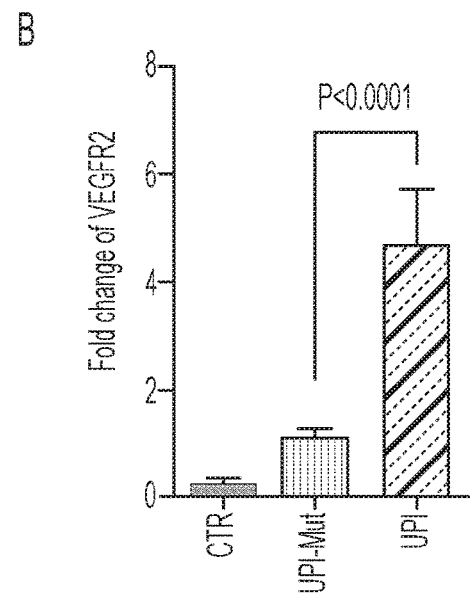
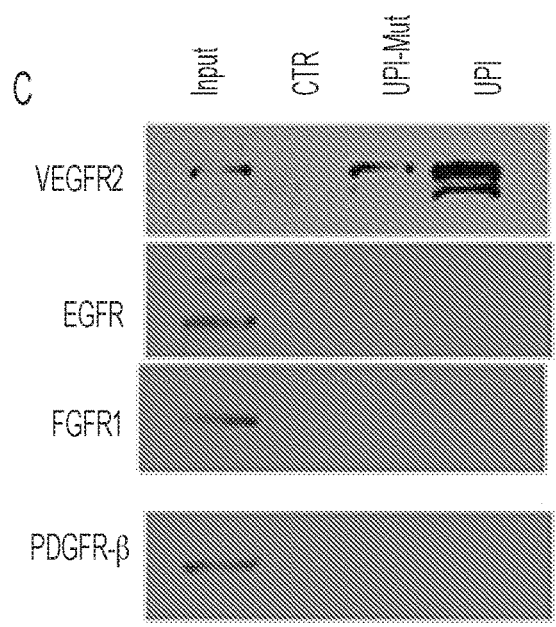
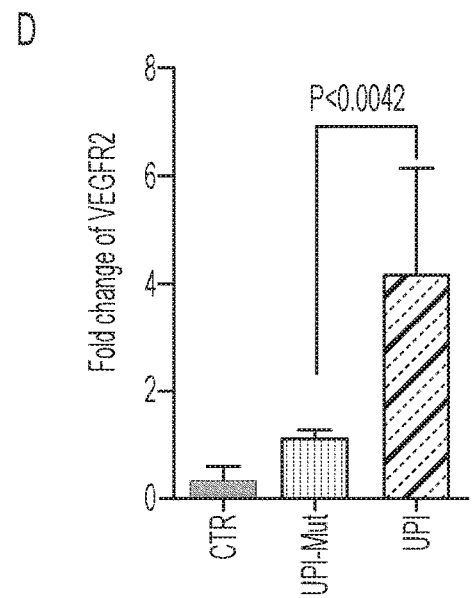
FIGS. 15A-D

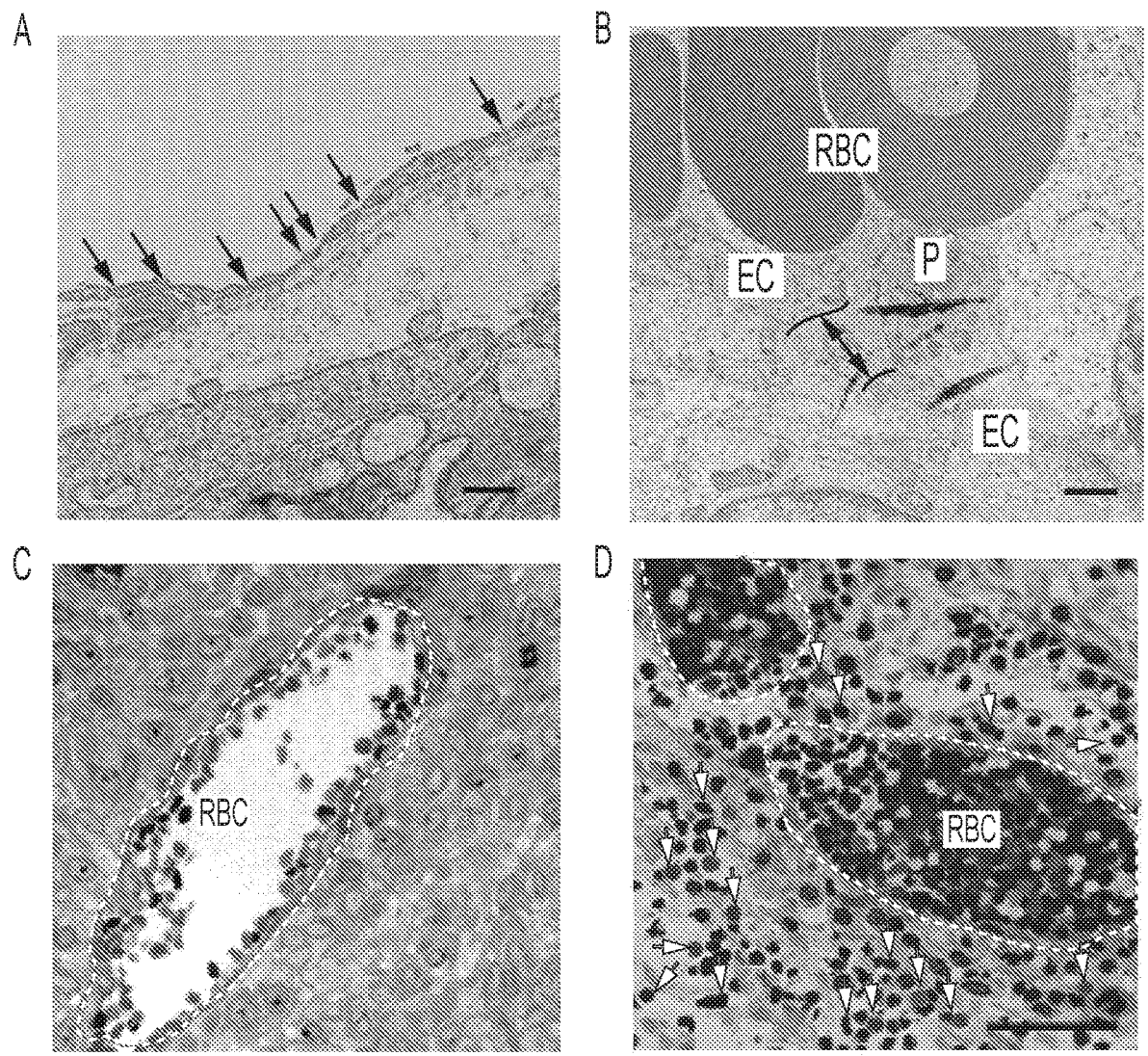
FIG. 16A-D

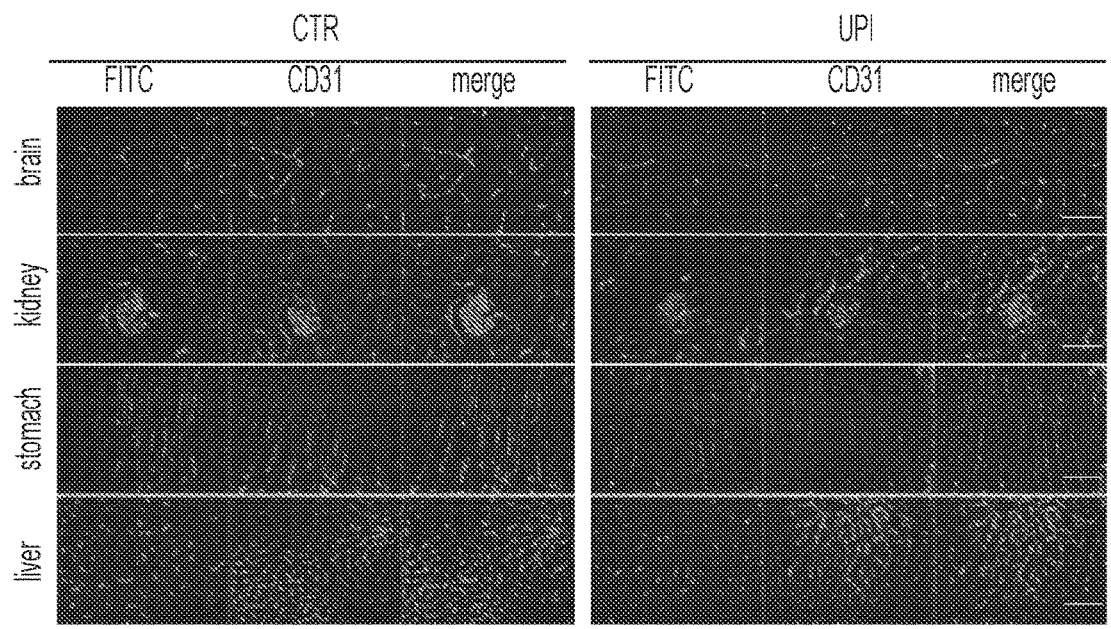
FIG. 17
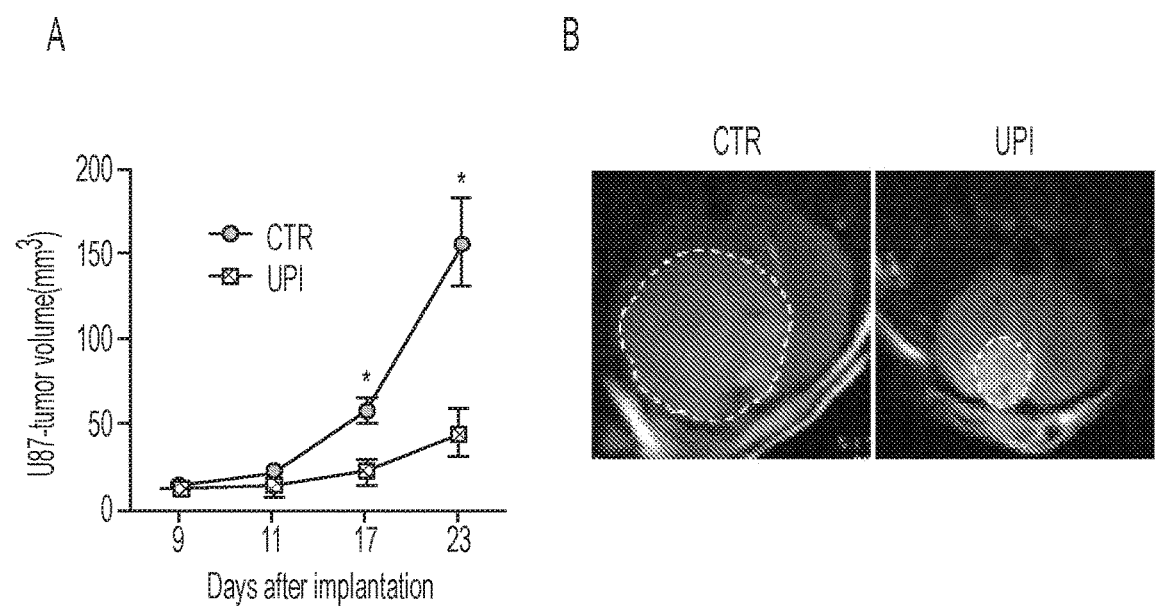
FIGS. 18A-B

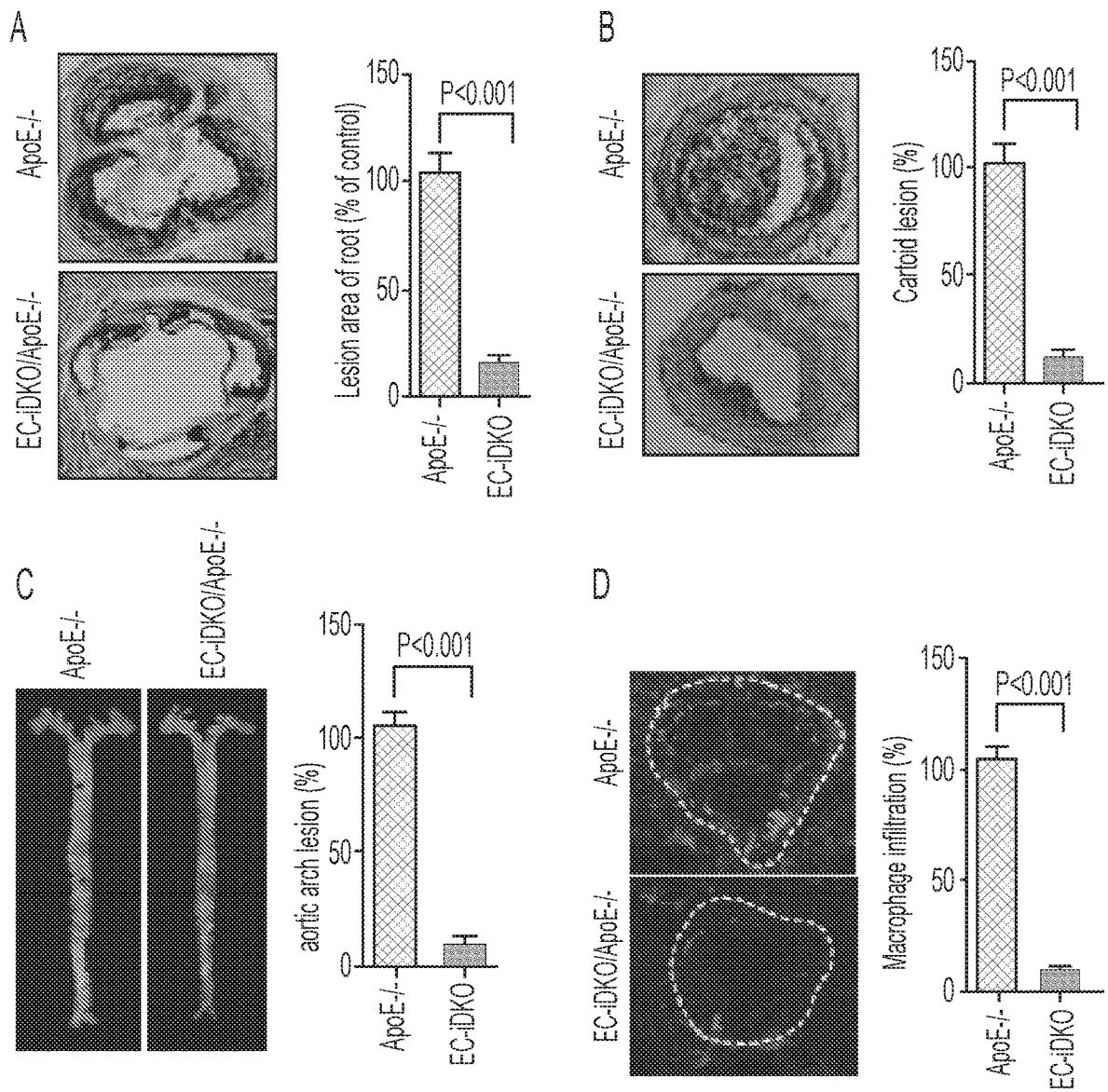
FIGS. 19A-D

E
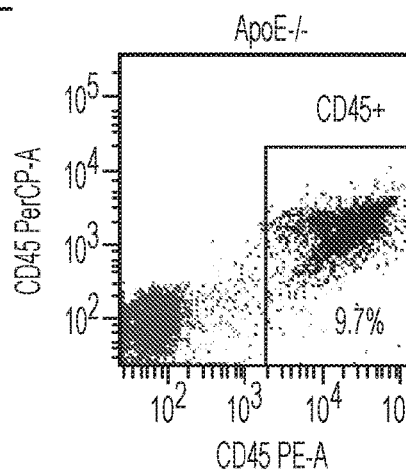
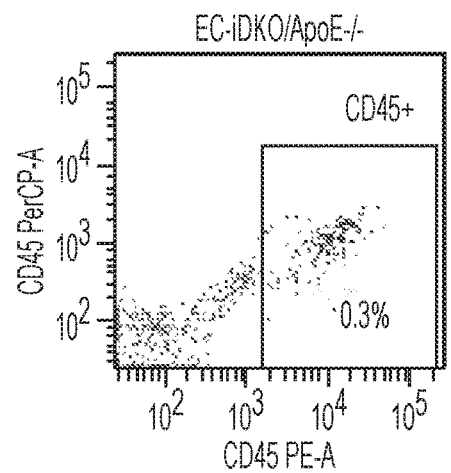
F
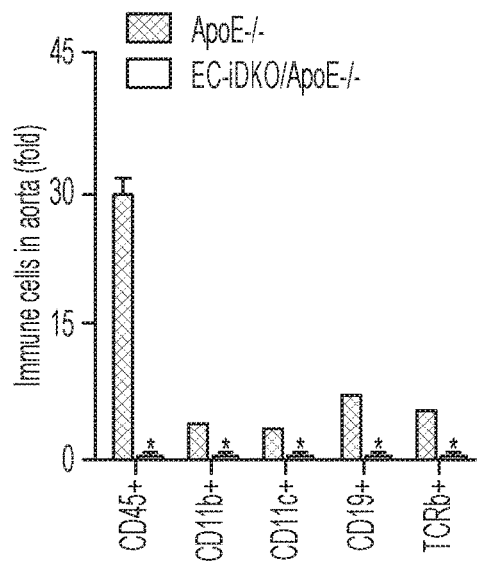
G
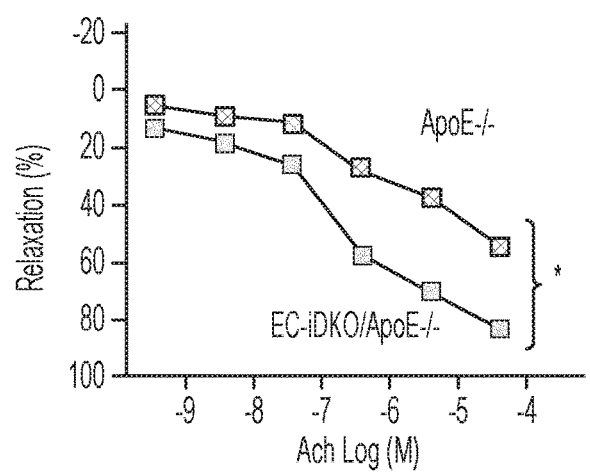
H
| | Plasma glucose and lipids ApoE-/- and EC-iDKO/ApoE-/- mice | | | | |
|---|---|---|---|---|---|
| | Glucose (mg/dl) | Cholesterol (mg/dl) | HDL (mg/dl) | LDL/VLDL (mg/dl) | Triglyceride (mmol/l) |
| ApoE-/- | 133.7±8.9 | 737.9±26.5 | 543±32.4 | 183.2±19.0 | 1.20±0.08 |
| EC-iDKO/ApoE-/- | 130.3±4.5 | 713.2±19.8 | 531±9.30 | 176.4±13.6 | 1.12±0.07 |
| P value | 0.7499 | 0.4766 | 0.7222 | 0.7783 | 0.4929 |
FIGS. 19E-H

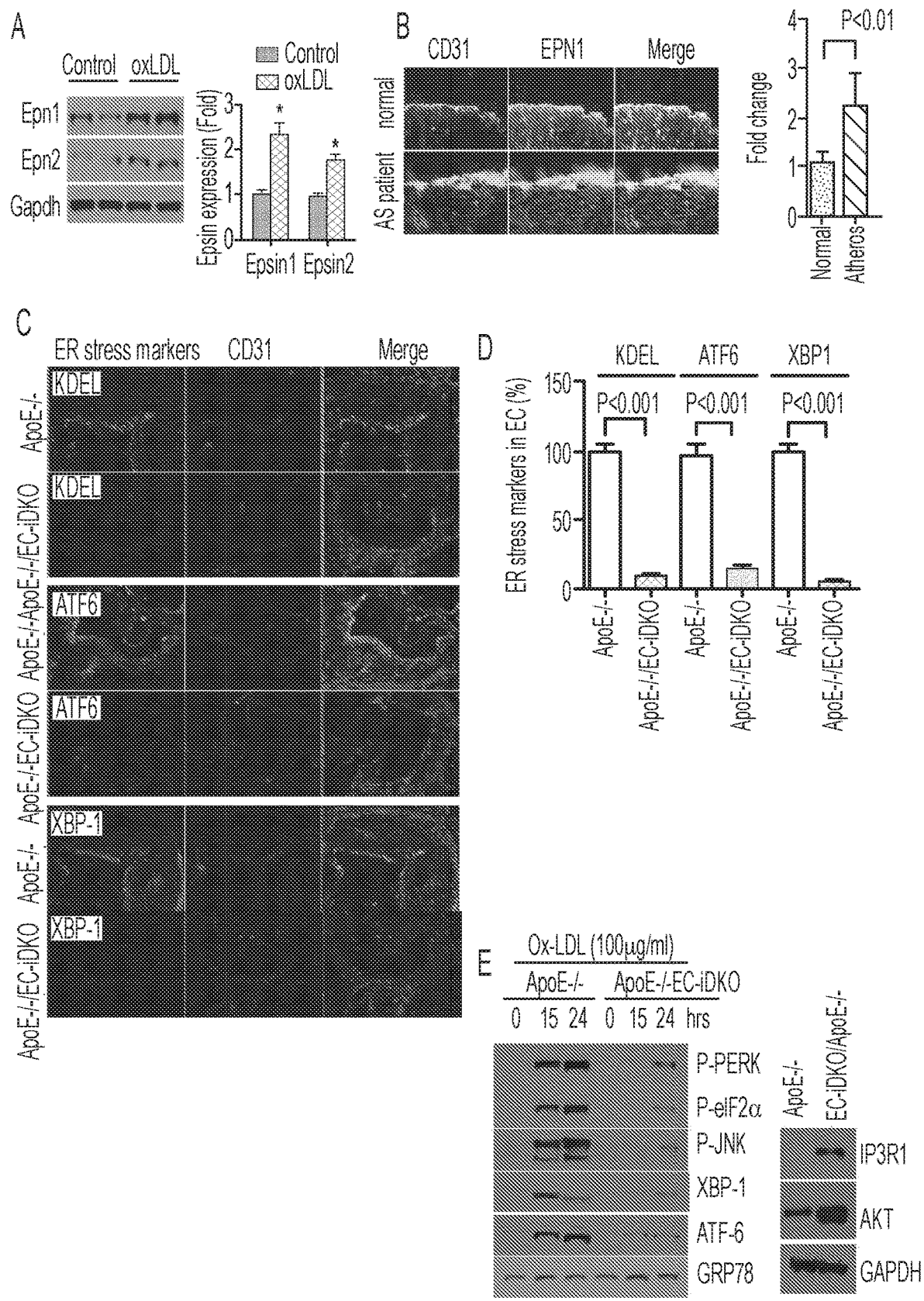
FIGS. 20A-E

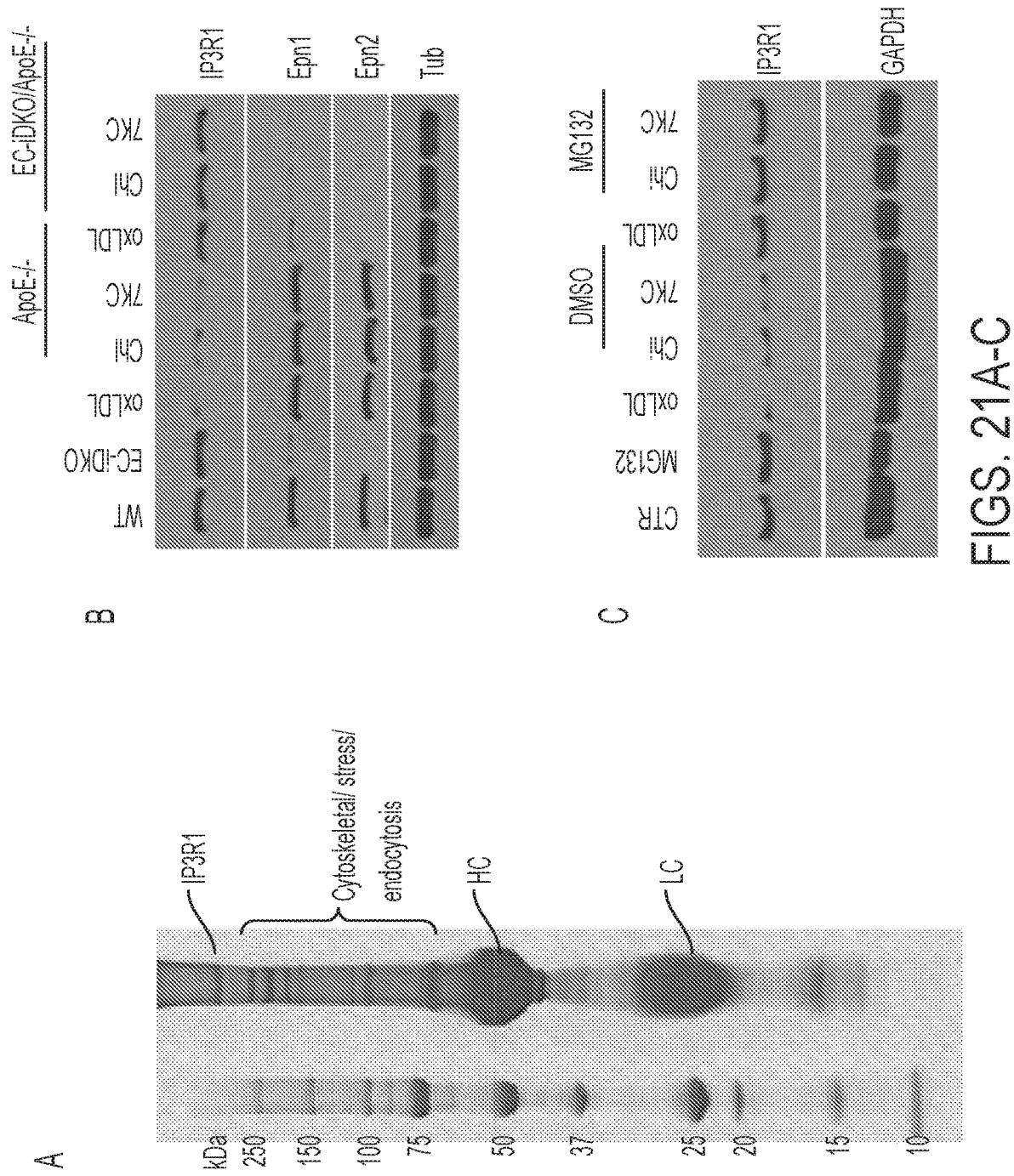
FIGS. 21A-C

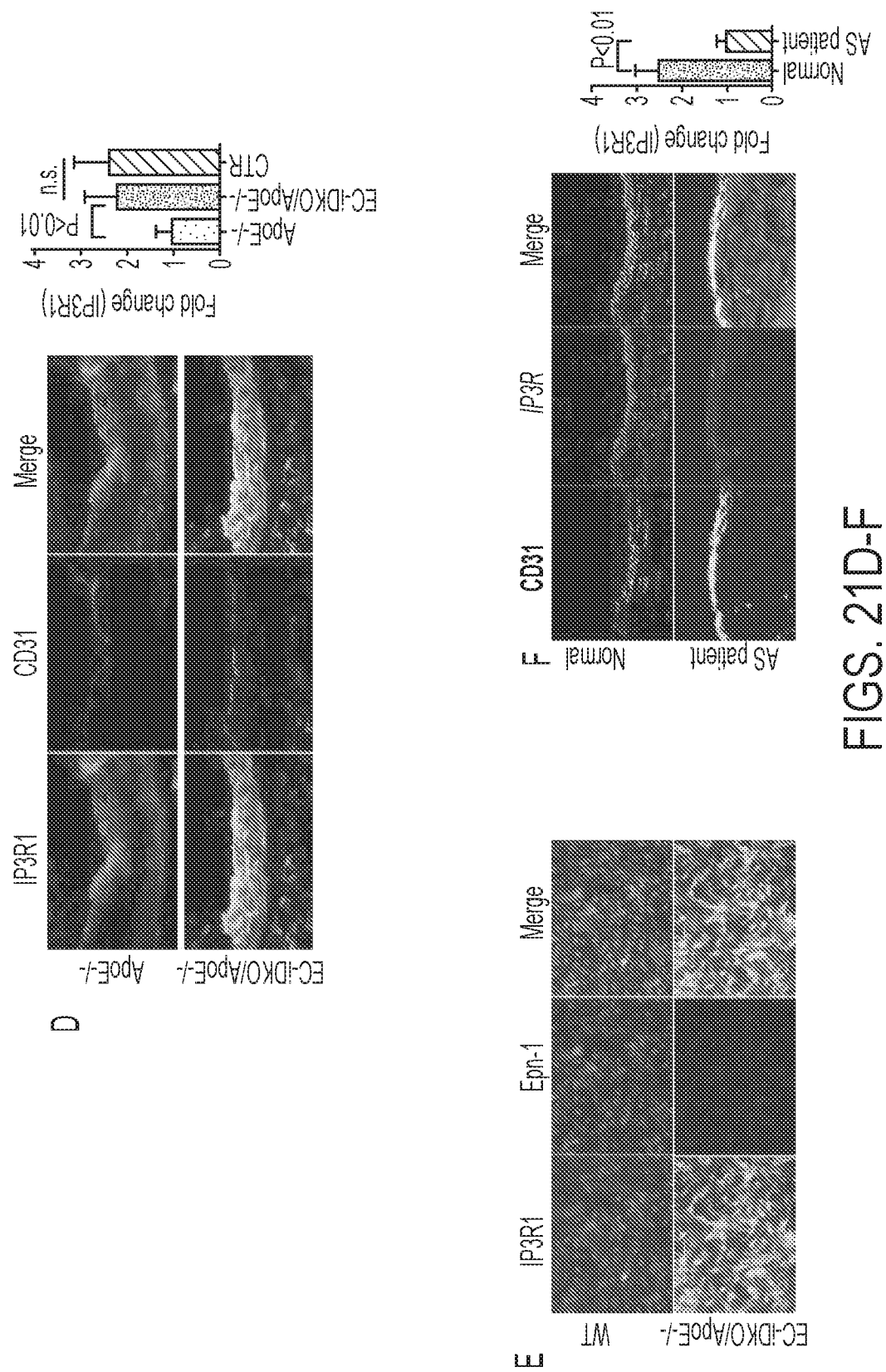
FIGS. 21D-F

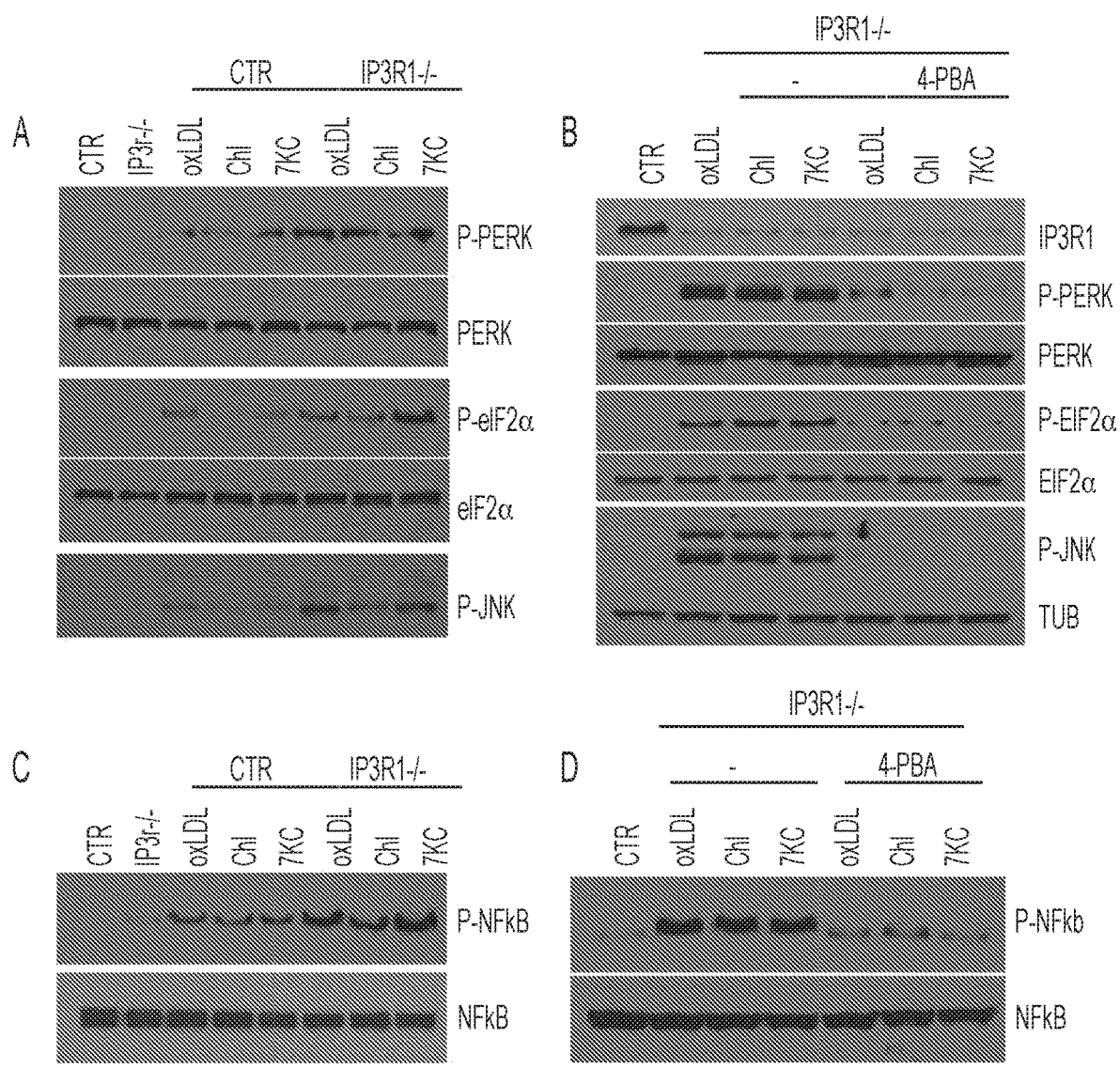
FIGS. 22A-D

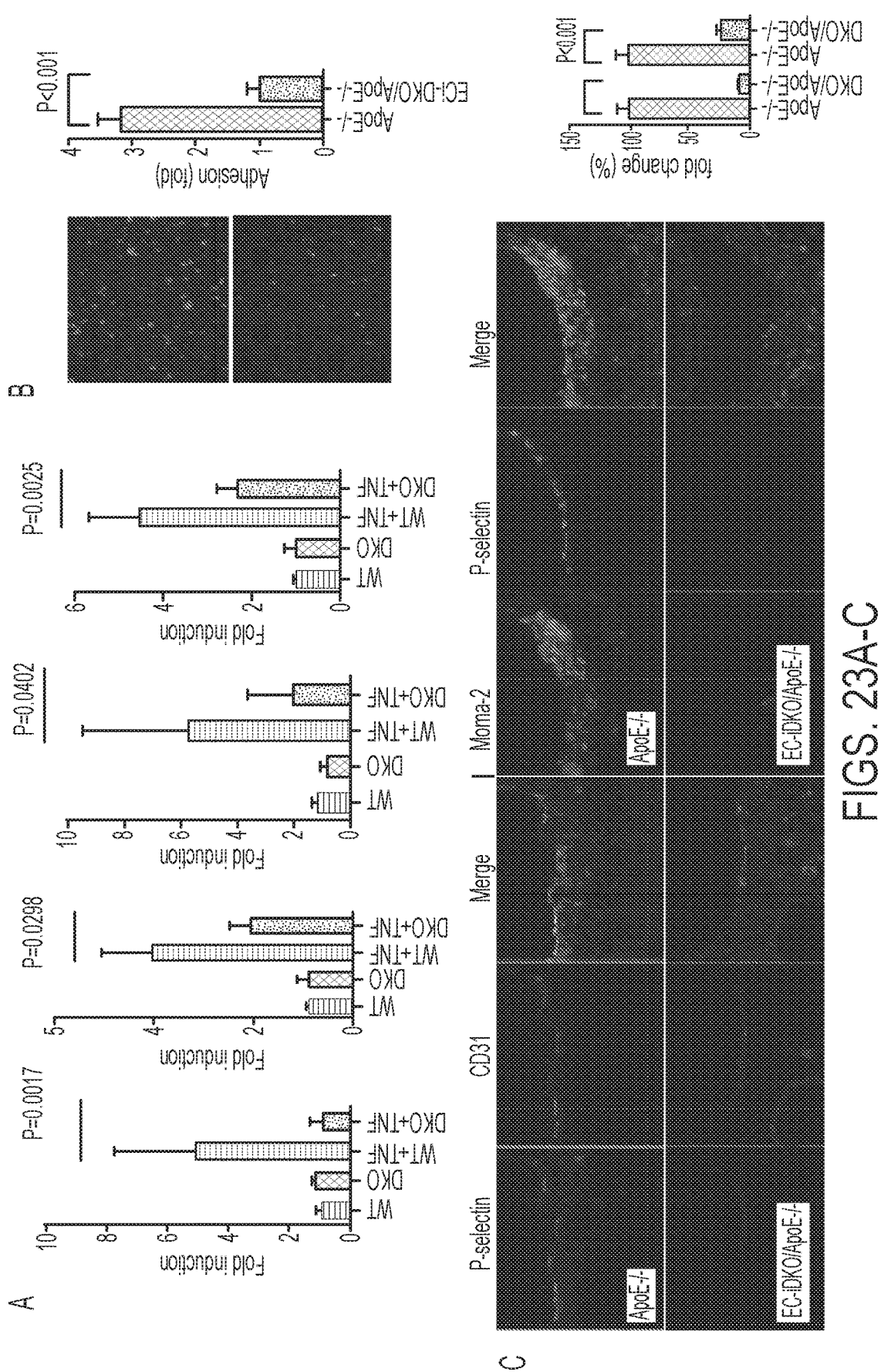
FIGS. 23A-C

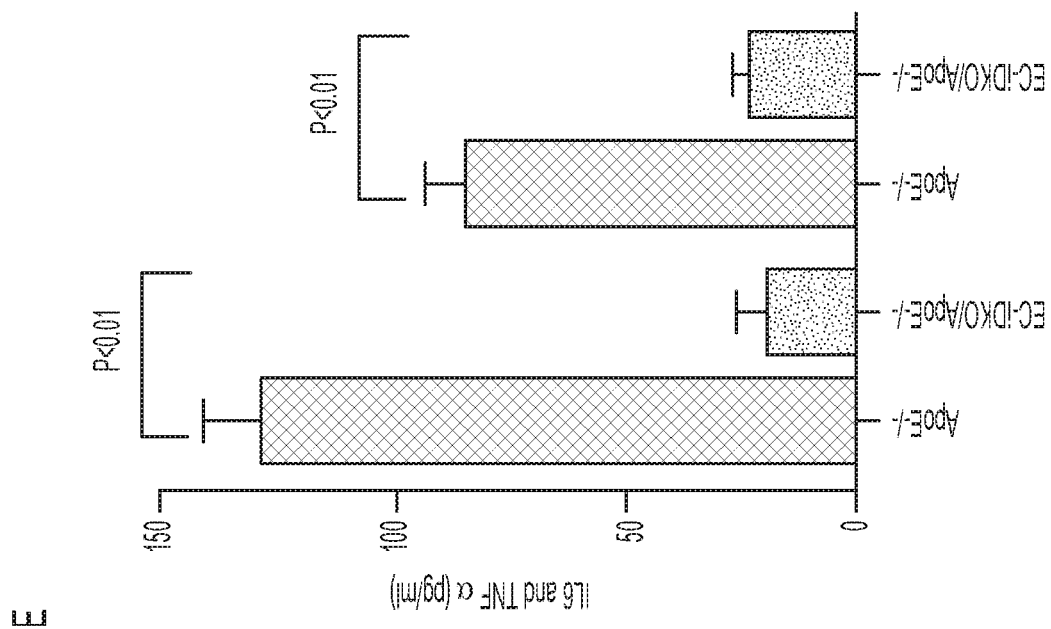
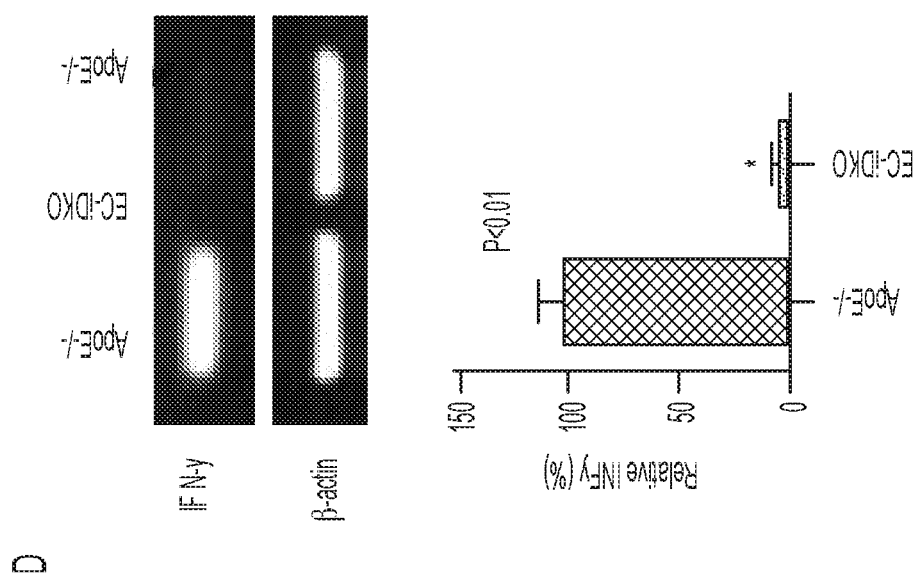
FIGS. 23D-E

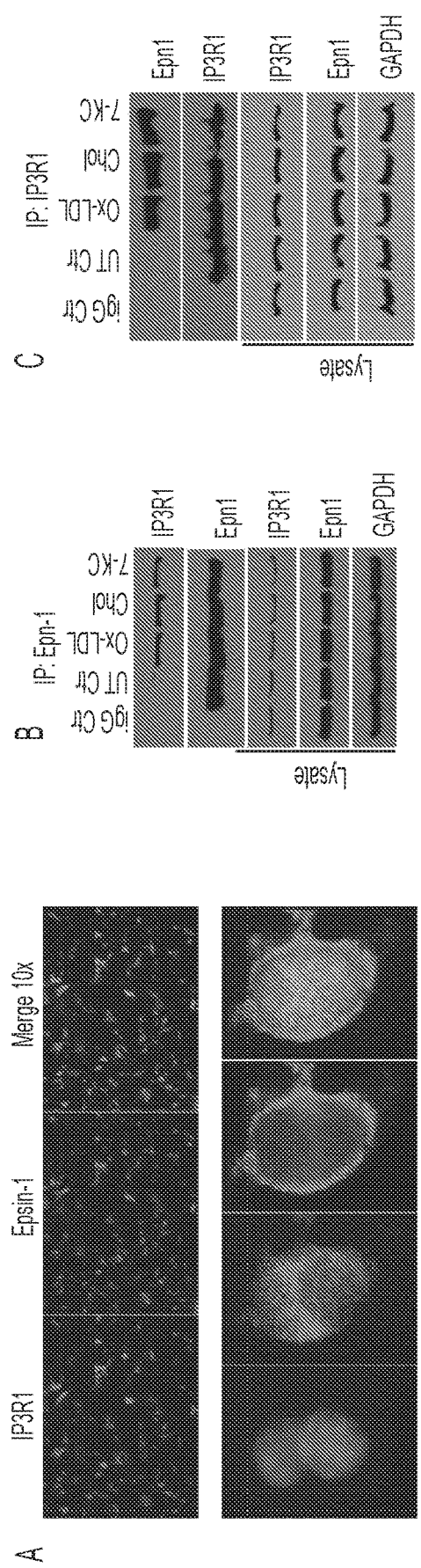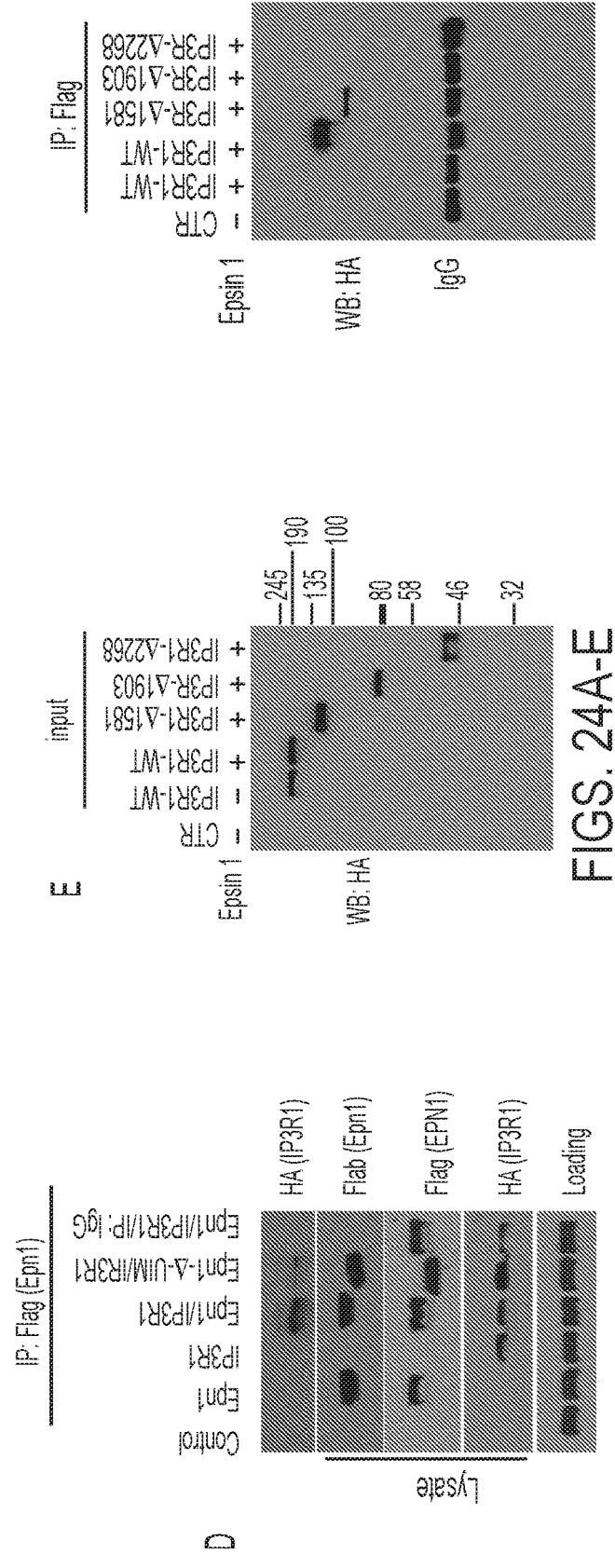
FIGS. 24A-E

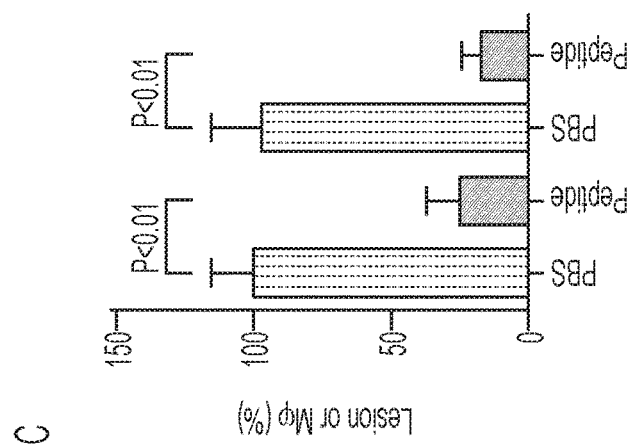
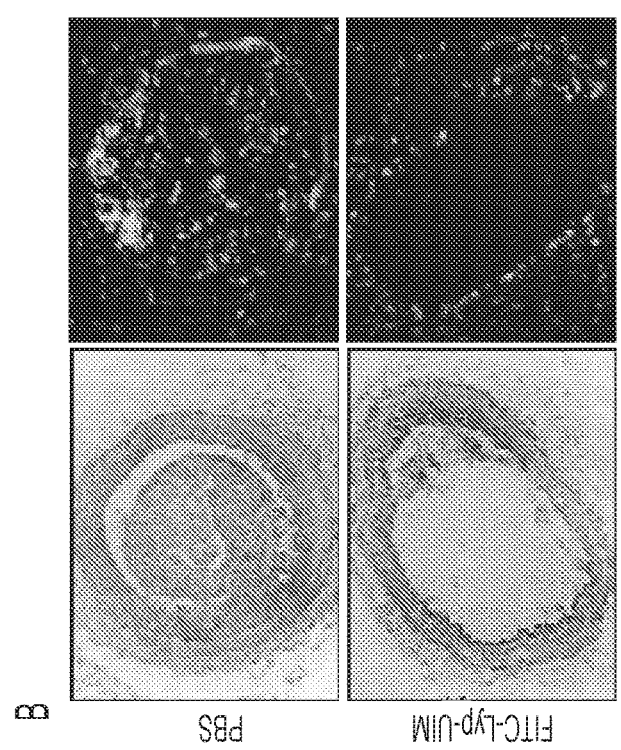
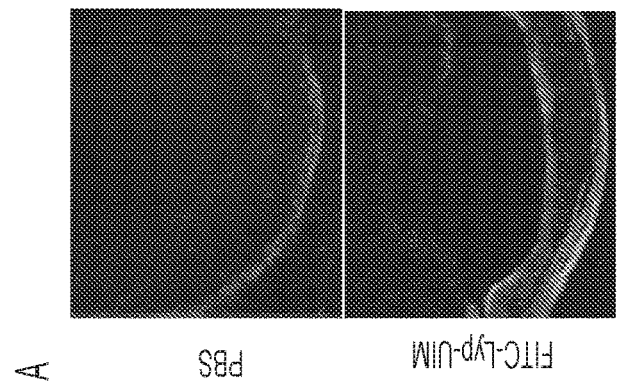
FIGS. 25A-C

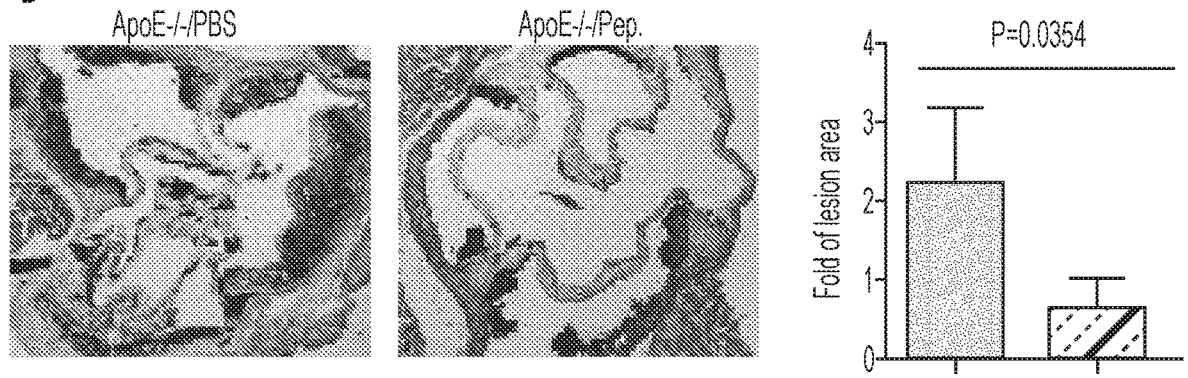
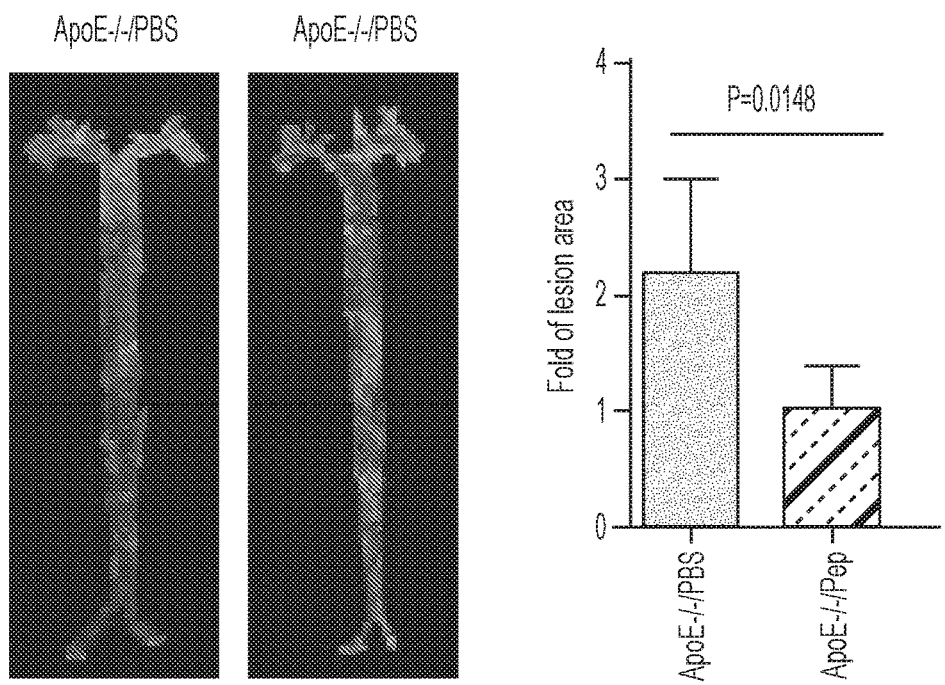
FIGS. 25D-E

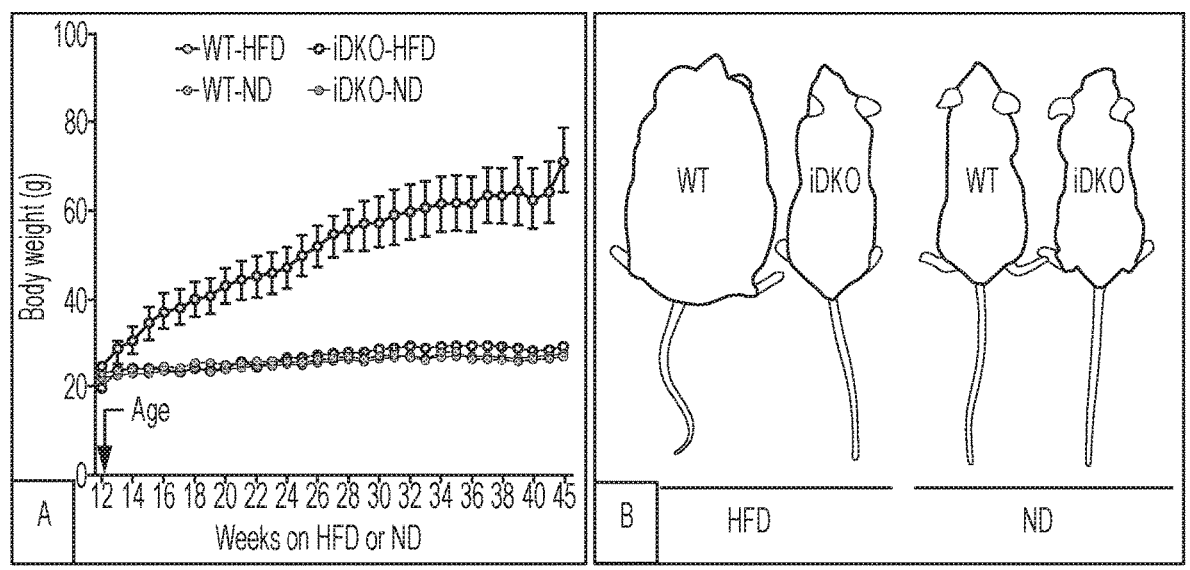
FIGS. 26A-B
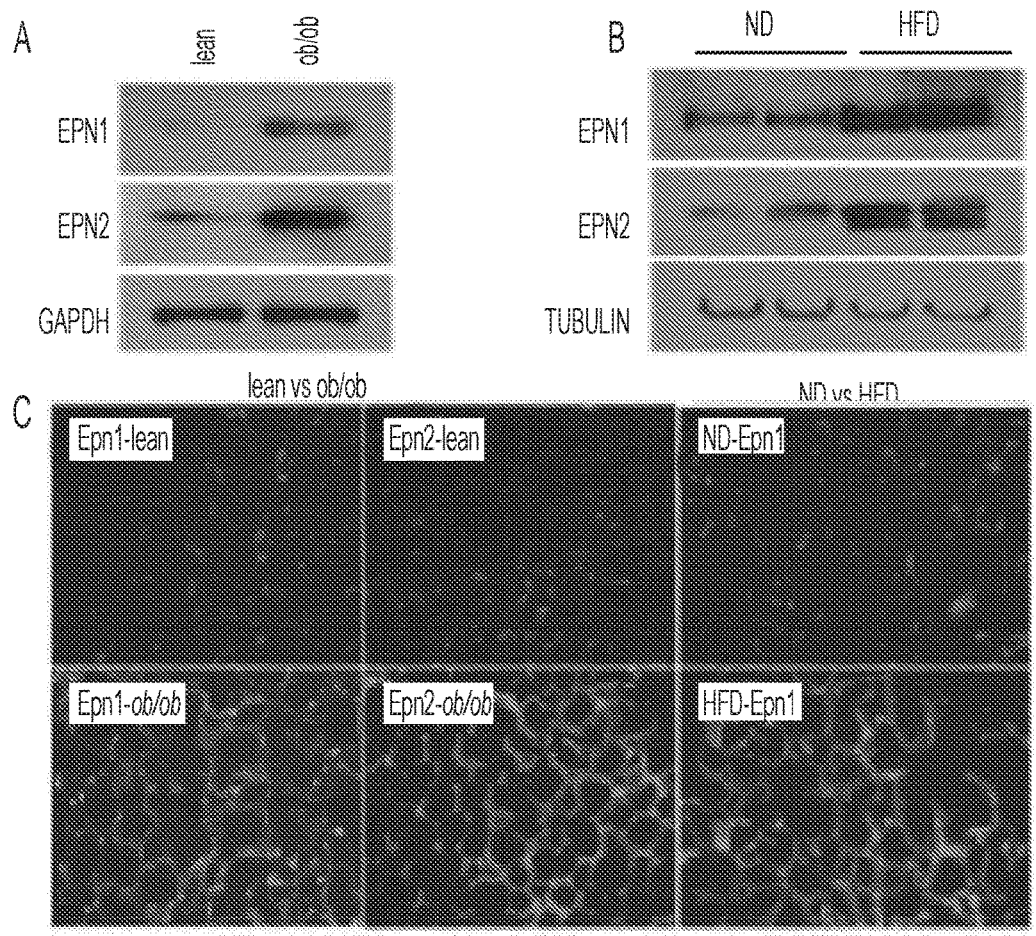
FIGS. 27A-C

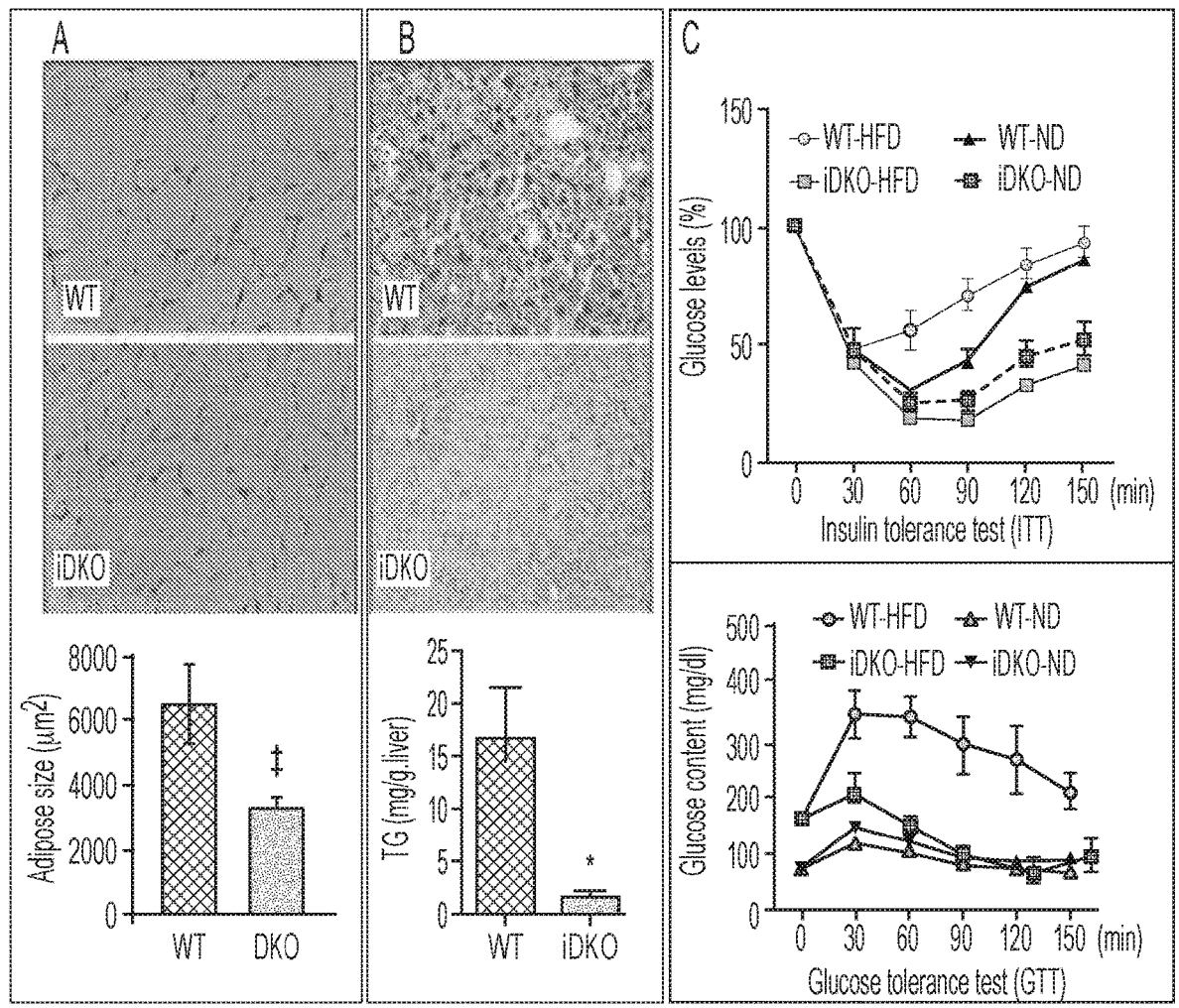
FIGS. 28A-C

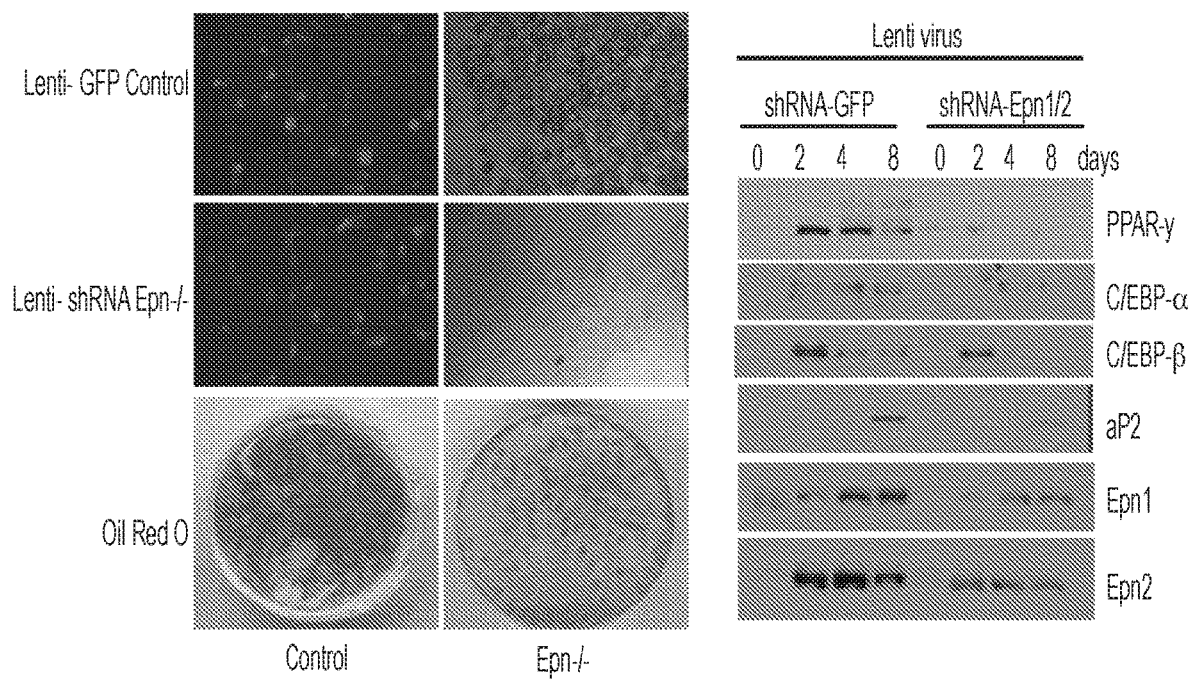
FIG. 30
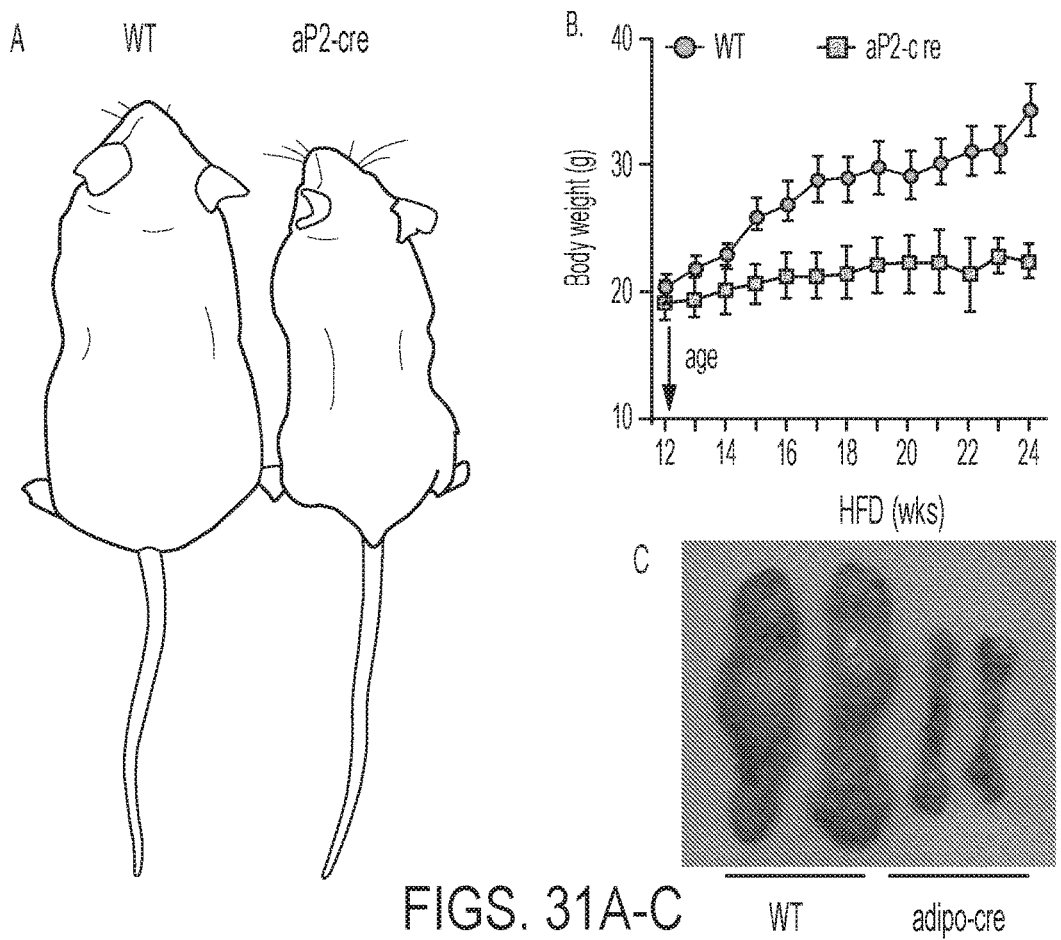
FIGS. 31A-C

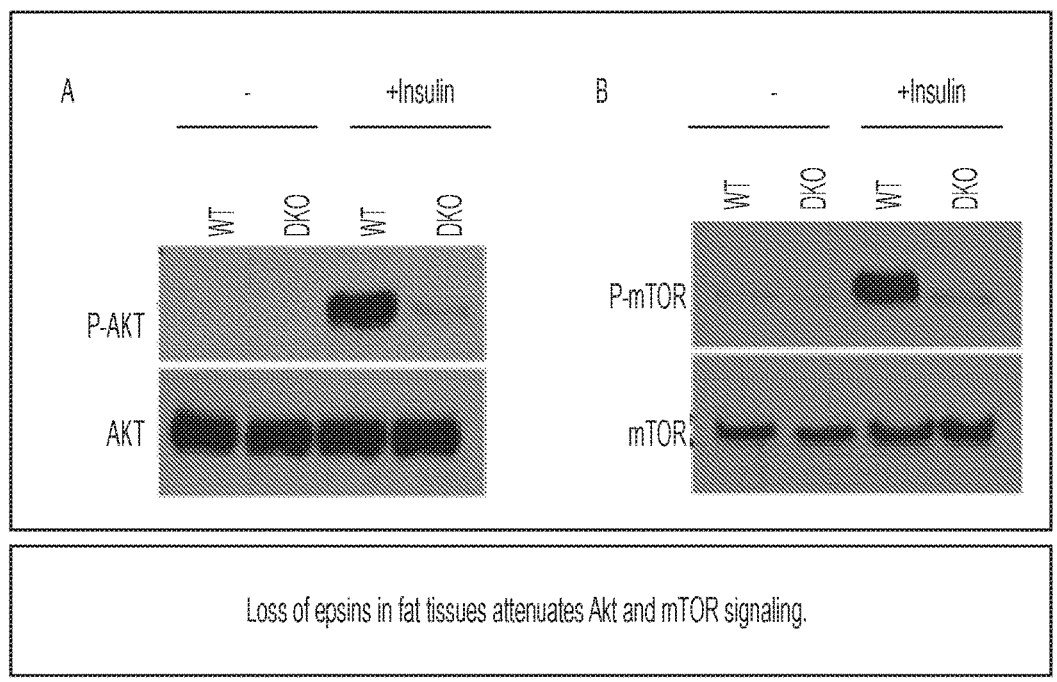
FIG. 32A-B
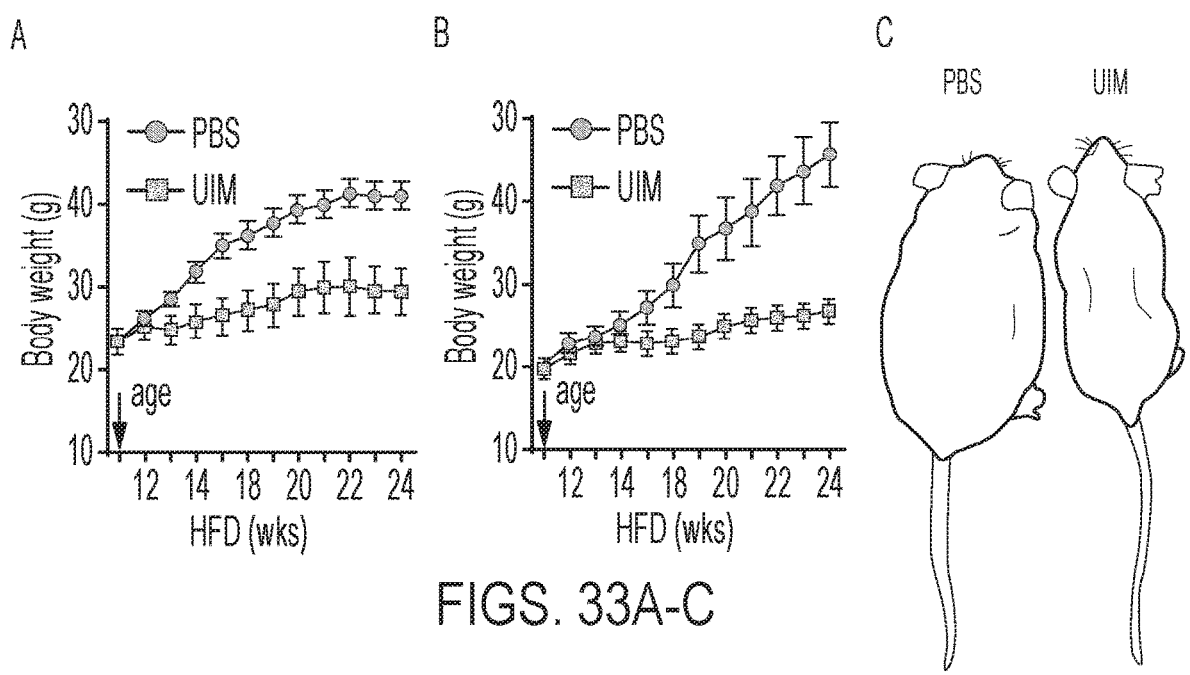
FIGS. 33A-C

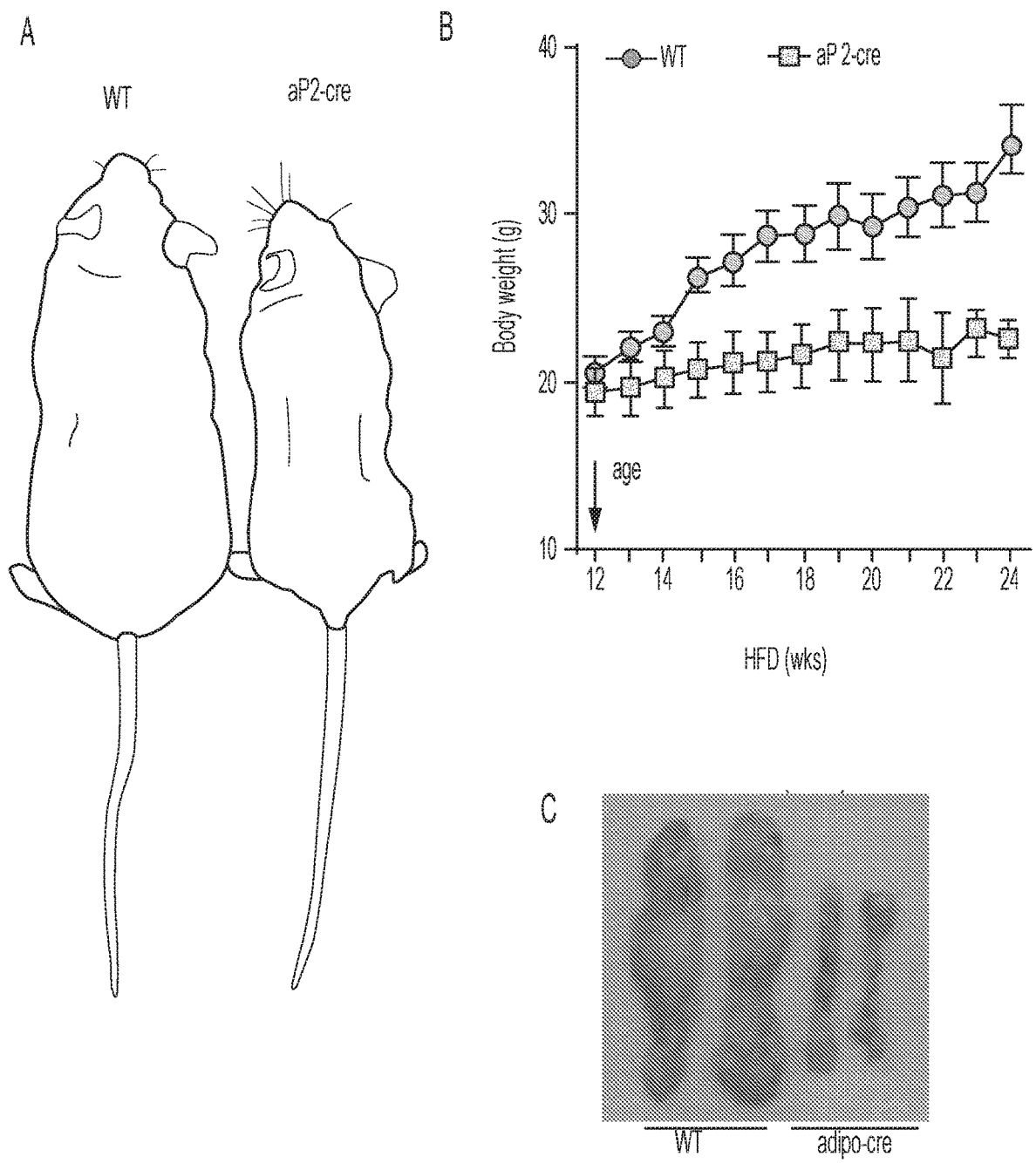
FIGS. 34A-C

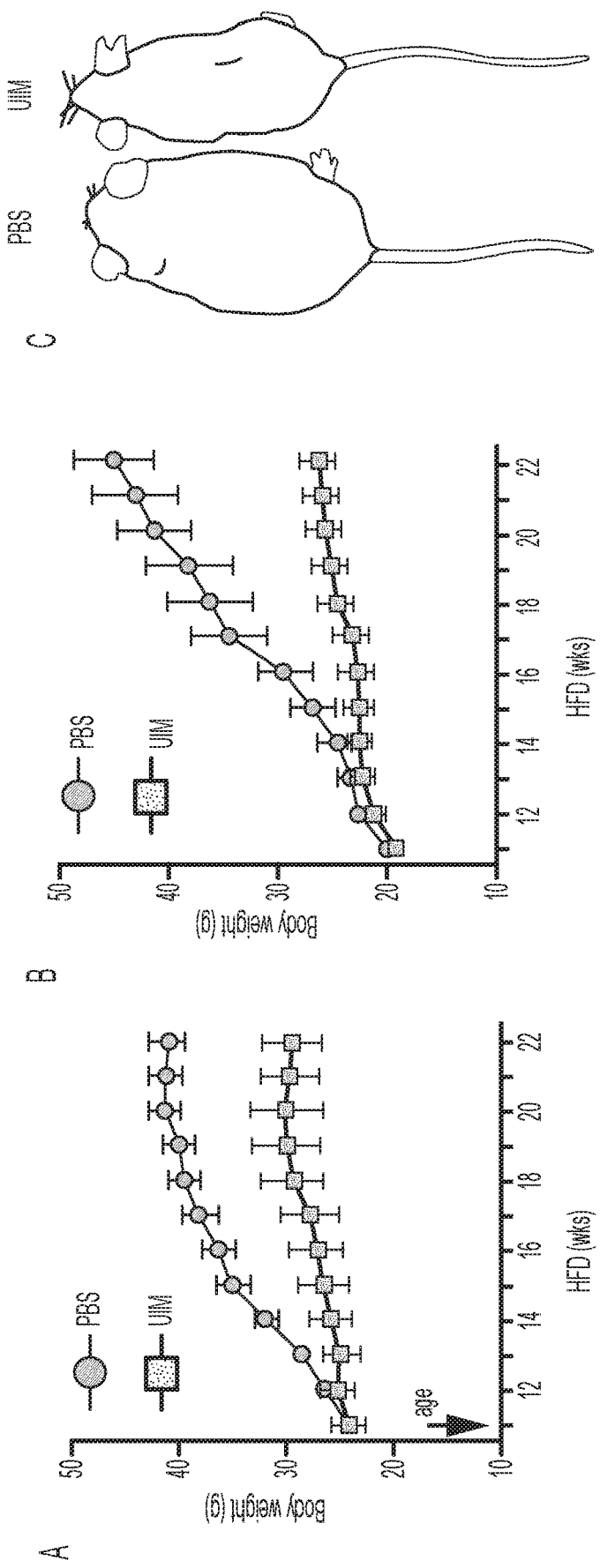
FIGS. 35A-C

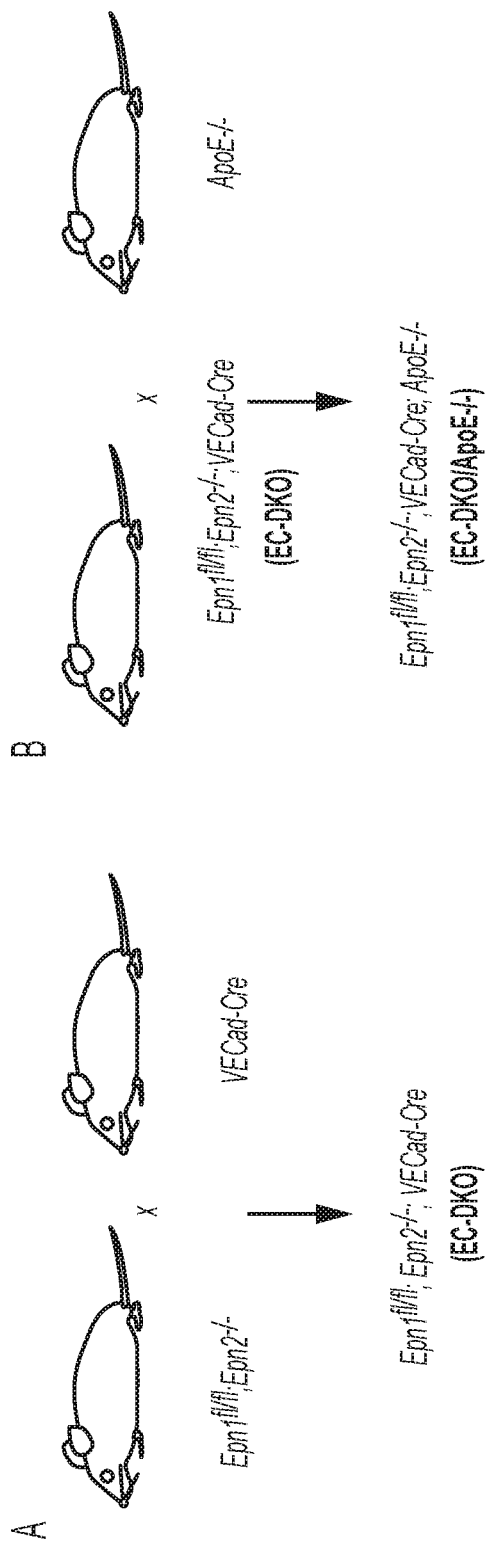
FIGS. 36A-B

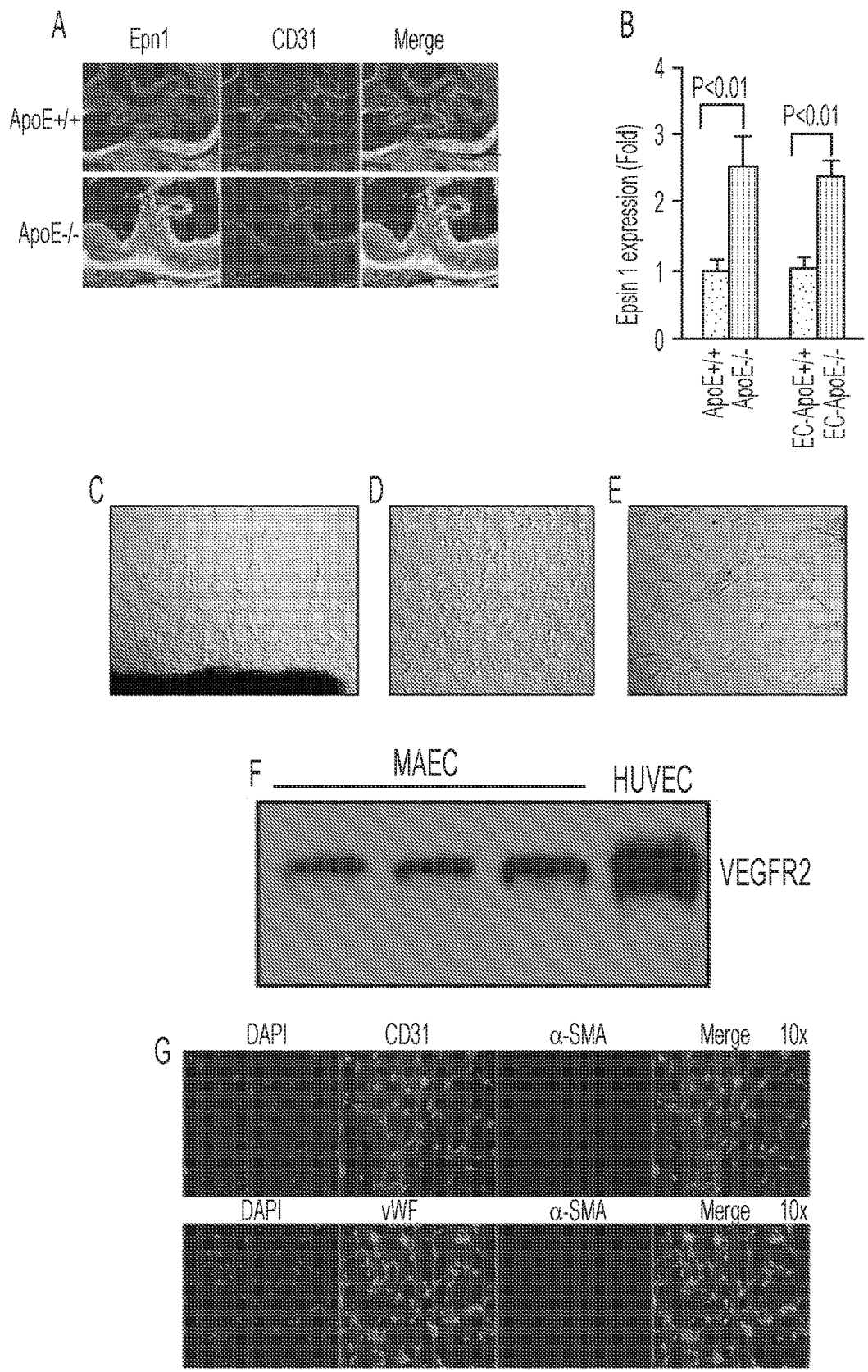
FIGS. 37A-G

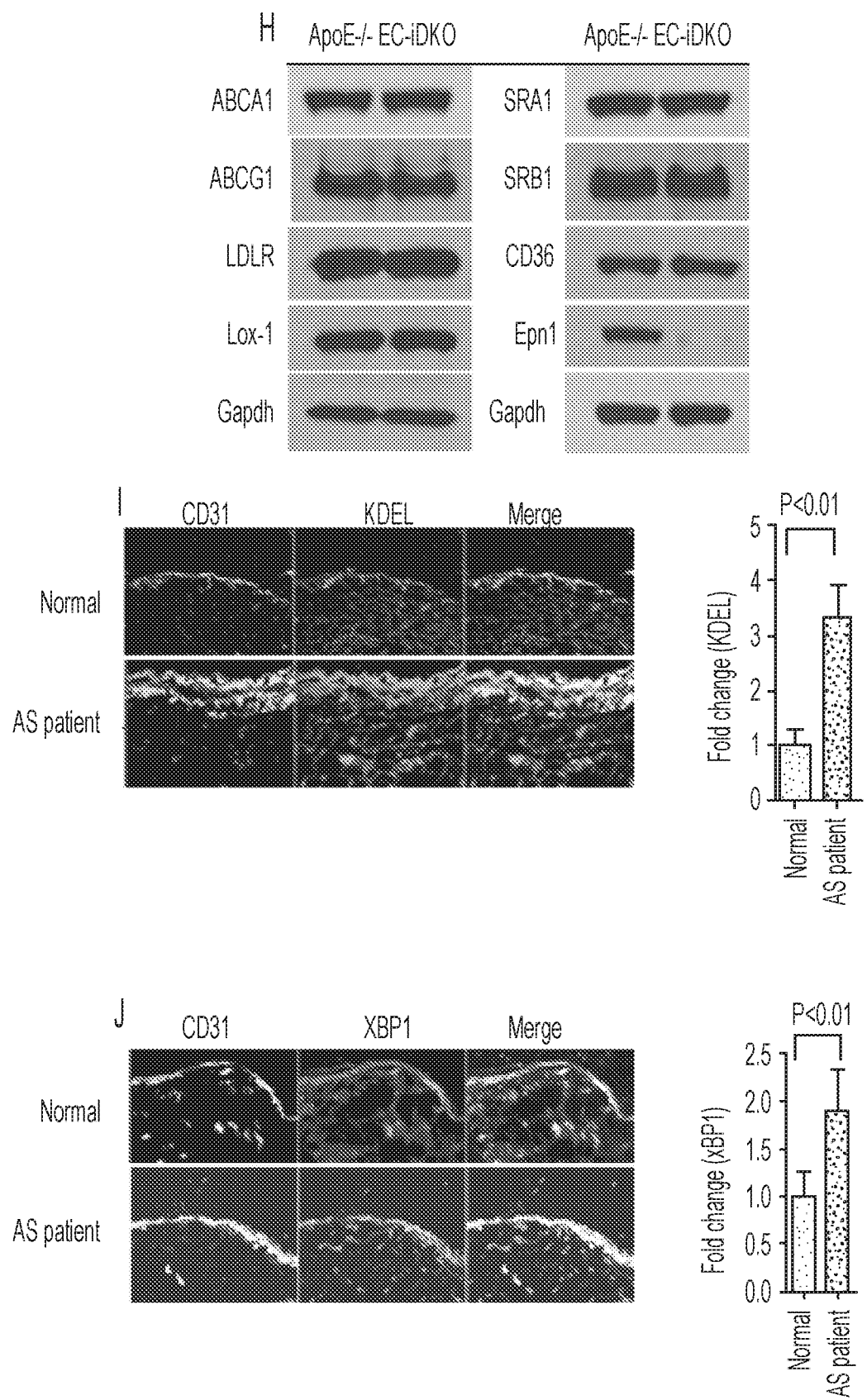
FIGS. 37H-J

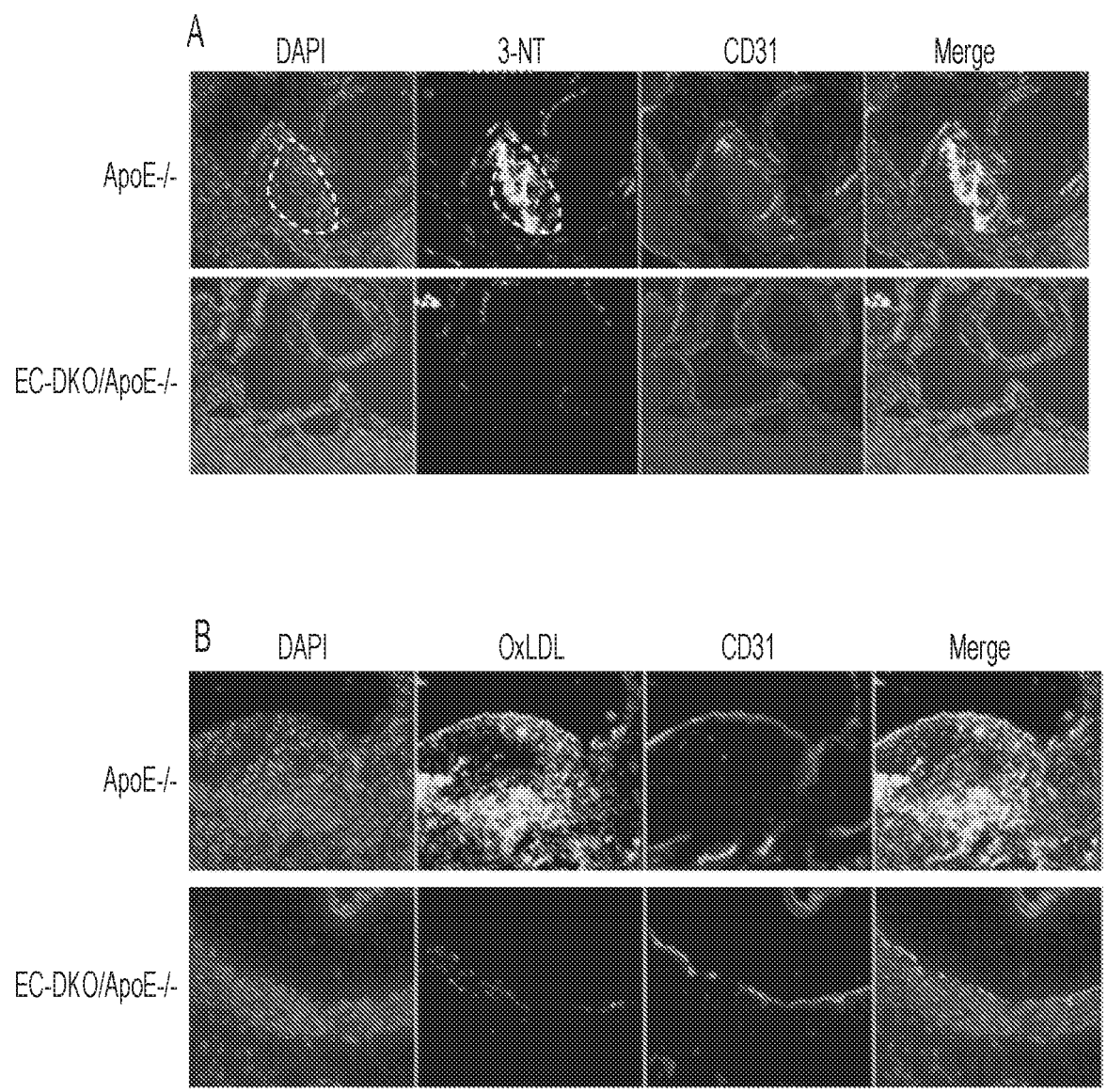
FIGS. 38A-B

UBIQUITIN INTERACTING MOTIF PEPTIDES AS THERAPEUTICS

This application is a national phase application under 35 U.S.C. § 371 of International Application No. PCT/US2016/036308, filed Jun. 8, 2016, which claims benefit of priority to U.S. Provisional Application Ser. No. 62/175,801, filed Jun. 15, 2015, the entire contents of which are hereby incorporated by reference.

Pursuant to 37 C.F.R. 1.821(c), a sequence listing is submitted herewith as an ASCII compliant text file named "OMRFP0125US_ST25.txt", created on Dec. 12, 2017 and having a size of ~17 kilobytes. The content of the aforementioned file is hereby incorporated by reference in its entirety.

BACKGROUND

1. Field

The present disclosure relates generally to the fields of oncology and anti-angiogenic therapy. More particularly, it concerns the use of UIM-containing peptides alone or in combination with other agents to treat cancer.

2. Description of Related Art

A. Cancer

Angiogenesis, essential for embryogenesis and postnatal tissue repair, is often exploited by tumors to support accelerated growth and exaggerated cancer cell proliferation (Folkman, 1971; Dvorak, 2002; Ferrara & Kerbel, 2005; Kerbel, 2008; Weis & Cheresh, 2011; Carmeliet & Jain, 2011 and Ziyad & Iruela-Arispe, 2011). The vascular endothelial growth factor (VEGF) signaling critical for angiogenesis has been therapeutically modulated to curb tumor expansion (Ferrara & Kerbel, 2005; Weis & Cheresh, 2011; Gaur et al., 2009; Kim et al., 1993; Brower, 1999 and Presta et al., 1997). Indeed, anti-VEGF therapies (Jain et al., 2006; Jubb et al., 2006 and Ferrara et al., 2004), such as Avastin (Ferrara et al., 2005), a humanized monoclonal anti-VEGF-A antibody, have proven effective in the treatment of a wide variety of cancers (Jain et al., 2006; Ferrara et al., 2004 and Ferrara et al., 2005). However, the rapid rate with which cancer cells mutate and adapt to changing microenvironments, including their dependence on tumor angiogenesis, stresses a continued need for new therapeutic strategies to combat developing drug resistance in cancer (Bergers & Hanahan, 2008). A better understanding of the molecular events governing tumor angiogenesis will therefore lead to alternative anti-angiogenic strategies to complement current anti-carcinogenic and anti-metastatic treatments. One such approach would be to shift the balance of VEGFR2 signaling towards uncontrolled angiogenesis and dysfunctional tumor vasculature (Pasula et al., 2012 and Tessneer et al., 2014). Identifying and designing therapeutics targeted to modulate these alternative events will significantly advance cancer therapy.

B. Atherosclerosis and Heart Disease

Atherosclerosis (also known as arteriosclerotic vascular disease or ASVD) is a specific form of arteriosclerosis in which an artery wall thickens as a result of invasion and accumulation of white blood cells (WBCs). The accumulation of the WBCs is termed "fatty streaks" early on because of appearance being similar to that of marbled steak. These accumulations contain both living, active WBCs (producing inflammation) and remnants of dead cells, including cholesterol and triglycerides. The remnants eventually include calcium and other crystallized materials, within the outermost and oldest plaque. The fatty streaks reduce the elasticity of the artery walls. However, they do not affect blood flow for decades, because the artery muscular wall enlarges at the locations of plaque. The wall stiffening may eventually increase pulse pressure; widened pulse pressure is one possible result of advanced disease within the major arteries.

Atherosclerosis is therefore a syndrome affecting arterial blood vessels due to a chronic inflammatory response of WBCs in the walls of arteries. This is promoted by low-density lipoproteins (LDL, plasma proteins that carry cholesterol and triglycerides) without adequate removal of fats and cholesterol from the macrophages by functional high-density lipoproteins (HDL). It is commonly referred to as a hardening or furring of the arteries. It is caused by the formation of multiple atheromatous plaques within the arteries.

The complications of advanced atherosclerosis are chronic, slowly progressive and cumulative. Most commonly, soft plaque suddenly ruptures, causing the formation of a thrombus that will rapidly slow or stop blood flow, leading to death of the tissues fed by the artery in approximately five minutes. This catastrophic event is called an infarction. One of the most common recognized scenarios is called coronary thrombosis of a coronary artery, causing myocardial infarction (a heart attack). The same process in an artery to the brain is commonly called stroke. Another common scenario in very advanced disease is claudication from insufficient blood supply to the legs. Atherosclerosis affects the entire artery tree, but mostly larger, high-pressure vessels such as the coronary, renal, femoral, cerebral, and carotid arteries. These are clinically silent because the person having the infarction does not notice the problem and does not seek medical help. Subsequently, major artery and heart disease can develop.

In sum, atherosclerosis plays a major role in the development of artery and heart disease, which are leading causes of mortality world-wide. Indeed, heart disease is perhaps the most significant healthcare burden in terms of cost in the world. Therefore, new treatment modalities are desperately needed.

C. Obesity

Obesity has become a major health problem in the United States and other developed nations. In the United States, 65% of the adult population is considered overweight or obese, and more than 30% of adults meet the criteria for obesity. The World Health Organization has estimated that more than 1 billion adults worldwide are overweight, with 300 million of these considered clinically obese. The incidence of obesity in children is also growing rapidly in many countries. Obesity is a major risk factor for cardiovascular disease, stroke, insulin resistance, type 2 diabetes, liver disease, neurodegenerative disease, respiratory diseases and other severe illnesses, and has been implicated as a risk factor for certain types of cancer including breast and colon cancer. Aside from its impacts on physical health, obesity has significant adverse effects on quality of life and psychological well-being. The incidence of obesity, already high, is likely to grow as a result of increasingly sedentary lifestyles in many countries. In addition, certain widely used psychiatric drugs, notably atypical antipsychotics, are associated with weight gain and increased risk of diabetes. Since these drugs must be used chronically to achieve adequate control of psychiatric symptoms, and treatment compliance in patients with mental disorders is frequently poor, these side effects present both a barrier to compliance and a significant additional health risk to patients.

Accordingly, there is a significant need for new anti-obesity treatments. In particular, there is a need for anti-obesity treatments with limited side effects that may be safely used in combination with other drugs that are in common use in obese patients, such as antidiabetic drugs, antihypertensive drugs, cholesterol-reducing agents, and insulin. Agents effective at treating of obesity would represent a significant advance.

SUMMARY

Thus, in accordance with the present disclosure, there is provided a method of treating cancer in a subject comprising administering to said subject a peptide comprising a ubiquitin interactive motif (UIM)-containing peptide having the sequence SGEEELQLQLALAMSKEE (SEQ ID NO: 1). The administration may be intra-tumoral, into the tumor vasculature, regional to a tumor, or systemic. The administration may be oral, intravenous, or intraarterial. The cancer may be recurrent, metastatic or multidrug resistant. The cancer may be brain cancer, head & neck cancer, throat cancer, nasopharyngeal cancer, esophageal cancer, lung cancer, stomach cancer, liver cancer, pancreatic cancer, colon cancer, rectal cancer, prostate cancer, testicular cancer, ovarian cancer, uterine cancer, cervical cancer, breast cancer, or skin cancer. Treating may comprise reducing tumor growth, reducing tumor size, reducing tumor burden, inducing apoptosis in cancer cells, inhibiting tumor tissue invasion, or inhibiting metastasis.

The UIM-containing peptide may further comprise a cell targeting peptide, a cell penetrating peptide and/or a lipid-targeting domain. The cell targeting domain may be an RGD peptide, such as an integrin binding peptide, and/or the lipid binding domain is derived from lyn kinase. The UIM-containing peptide may comprise L amino acids, D amino acids, or a mixture of L and D amino acids. The method may further comprise administering to said patient a second anti-cancer therapy, such as radiation, surgery, chemotherapy, hormone therapy, immunotherapy, or toxin therapy, including where the second anti-cancer therapy is given before, after, before and after or at the same time as said UIM-containing peptide. The UIM-containing peptide may be about 18-40 residues in length, including precisely or about 18, 19, 20, 21, 22, 23, 24, 25, 26, 27, 28, 29, 30, 31, 32, 33, 34, 35, 36, 37, 38, 39 or 40 residues in length. The UIM-containing peptide may comprises of or consist of the sequence SGEEELQLQLALAMSKEEMGCIKSKRKCRGDKGPDC (SEQ ID NO: 2).

In another embodiment, there is provided a method of inducing non-productive vessel formation in a subject comprising administering to said subject a peptide comprising a ubiquitin interactive motif (UIM)-containing peptide having the sequence SGEEELQLQLALAMSKEE (SEQ ID NO: 1). The administration may be oral, intramuscular, subcutaneous, intravenous, or intraarterial. The subject may have cancer, such as recurrent, metastatic or multidrug resistant cancer. The cancer may be brain cancer, head & neck cancer, throat cancer, nasopharyngeal cancer, esophageal cancer, lung cancer, stomach cancer, liver cancer, pancreatic cancer, colon cancer, rectal cancer, prostate cancer, testicular cancer, ovarian cancer, uterine cancer, cervical cancer, breast cancer, skin cancer or a blood cancer. The subject may have a non-cancer neovascular disease, such as retinal neovascularization, haemorrhagic telangiectasia (HHT), neurofibromatosis type 1, familial cavernous malformation, and forms of lymphangiogenesis.

The UIM-containing peptide may further comprise a cell targeting peptide, a cell penetrating peptide and/or a lipid-targeting domain. The cell targeting domain may be an RGD peptide, such as an integrin binding peptide, and/or the lipid binding domain is derived from lyn kinase. The UIM-containing peptide may comprise L amino acids, D amino acids, or a mixture of L and D amino acids. The method may further comprise administering to said patient a secondary therapy, such as ruboxistaurine, a VEGF inhibitor, anti-IL-20, ranibizumab, bevacizumab or pegaptanib, including where the second anti-cancer therapy is given before, after, before and after or at the same time as said UIM-containing peptide. The UIM-containing peptide may be about 18-40 residues in length, including precisely or about 18, 19, 20, 21, 22, 23, 24, 25, 26, 27, 28, 29, 30, 31, 32, 33, 34, 35, 36, 37, 38, 39 or 40 residues in length. The UIM-containing peptide may comprises of or consist of the sequence SGEEELQLQLALAMSKEEMGCIKSKRKCRGDKGPDC (SEQ ID NO: 2).

Also provided is a pharmaceutical composition comprising a ubiquitin interactive motif (UIM)-containing peptide comprising the sequence SGEEELQLQLALAMSKEE (SEQ ID NO: 1) dispersed in a pharmacalogically acceptable medium, carrier or diluent. The UIM-containing peptide may further comprise a cell targeting peptide, a cell penetrating peptide and/or a lipid-targeting domain. The cell targeting domain may be an RGD peptide, and/or the lipid targeting domain is membrane anchoring peptide. The cell targeting domain may comprise the sequence CRGDKGPDC (SEQ ID NO: 3). The lipid targeting domain may comprise the sequence MGCIKSKRK (SEQ ID NO: 4). The peptide may comprise L amino acids, D amino acids, or a mixture of L and D amino acids. The UIM-containing peptide may be about 18-50 residues in length, such as precisely or about 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 residues in length. The composition may be formulated in a lipid carrier. The UIM-containing peptide may comprise of or consist of the sequence SGEEELQLQLALAMSKEEMGCIKSKRKCRGDKGPDC (SEQ ID NO: 2), CGNKRTRGCSGEEELQLQLALAMSKEE (SEQ ID NO: 5), CKGGRAKDCSGEEELQLQLALAMSKEE (SEQ ID NO: 6), or SGEEELQLQLALAMSKEEMGCIKSKRK (SEQ ID NO: 7).

In still a further embodiment, there is provided a method of inhibiting atherosclerosis in a subject comprising administering to said subject a peptide comprising a ubiquitin interactive motif (UIM)-containing peptide comprising the sequence SGEEELQLQLALAMSKEE (SEQ ID NO: 1). The administration may be intravenous, intra-arterial, intranasal, transdermal or oral. The administration may be daily, every other day, weekly or monthly. The patient may exhibit one or more symptoms of heart disease. The one or more symptoms of heart disease may be selected from decreased exercise capacity, decreased blood ejection volume, increased left ventricular end diastolic pressure, increased pulmonary capillary wedge pressure, decreased cardiac output, pathologic cardiac index, increased pulmonary artery pressures, increased left ventricular end systolic and diastolic dimensions, increased left and right ventricular wall stress, or wall tension, decreased quality of life, or increased disease-related morbidity and mortality. Treating may comprise slowing atherosclerotic plaque growth in said subject, limiting the formation of new atherosclerotic plaques, limiting the size of atherosclerotic plaques, and inducing regression of an atherosclerotic plaque.

The UIM-containing peptide may further comprise a cell targeting peptide, a cell penetrating peptide and/or a lipid-targeting domain. The cell targeting domain may comprise CGNKRTRGC (SEQ ID NO: 8), and/or the lipid targeting domain is membrane anchoring peptide. The UIM-containing peptide may comprise L amino acids, D amino acids, or a mixture of L and D amino acids. The method may further comprise administering to said patient a second anti-atherosclerosis therapy, such as a statin. The second anti-atherosclerosis therapy may be given before, after, before and after or at the same time as said UIM-containing peptide. The UIM-containing peptide may be 27 to about 50 residues in length, such as precisely or about 27, 28, 29, 30, 31, 32, 33, 34, 35, 36, 37, 38, 39, 40, 41, 42, 43, 44, 45, 46, 47, 48, 49 or 50 residues in length. The UIM-containing peptide may consist of the sequence CGNKRTRGCSGEEELQLQLALAMSKEE (SEQ ID NO: 5).

In a further embodiment, there is provided a method of reducing the risk of myocardial infarction in a subject comprising administering to said subject a peptide comprising a ubiquitin interactive motif (UIM)-containing peptide comprising the sequence SGEEELQLQLALAMSKEE (SEQ ID NO: 1).

Also provided is a method of treating heart disease in a subject comprising administering to said subject a peptide comprising a ubiquitin interactive motif (UIM)-containing peptide comprising the sequence SGEEELQLQLALAMSKEE (SEQ ID NO: 1).

Additionally, there is provided a method of reducing atherosclerotic plaque rupture in a subject comprising administering to said subject a peptide comprising a ubiquitin interactive motif (UIM)-containing peptide comprising the sequence SGEEELQLQLALAMSKEE (SEQ ID NO: 1).

Another embodiment involves a method of reducing the risk of restenosis in a subject comprising administering to said subject a peptide comprising a ubiquitin interactive motif (UIM)-containing peptide comprising the sequence SGEEELQLQLALAMSKEE (SEQ ID NO: 1).

Yet a further embodiment provides for a method of reducing vascular inflammation in a subject comprising administering to said subject a peptide comprising a ubiquitin interactive motif (UIM)-containing peptide comprising the sequence SGEEELQLQLALAMSKEE (SEQ ID NO: 1).

Still further, there is provided a method of reducing weight in a subject in need thereof comprising administering to the subject a peptide comprising a ubiquitin interactive motif (UIM)-containing peptide comprising the sequence SGEEELQLQLALAMSKEE (SEQ ID NO: 1) in an amount sufficient to reduce the subject's weight. The UIM-containing peptide may comprise of or consist of the sequence CKGGRAKDCSGEEELQLQLALAMSKEE (SEQ ID NO: 6). The subject may have excess body fat, may be overweight, may have a body mass index (BMI) is from 25 kg/m² to 30 kg/m², may be obese and/or exhibit one of more symptoms of obesity, such as class I obesity, may have a BMI of from 30 kg/m² to 35 kg/m², may a have class II obesity, may have a BMI of from 35 kg/m² to 40 kg/m², may have class III obesity, or may have a BMI of from 40 kg/m² to 80 kg/m². The subject may be a human subject.

The weight of the subject may have been measured or may be measured. The weight of the subject may have been measured prior to administering the UIM-containing peptide and may be measured after administering the UIM-containing peptide. The body mass index (BMI) of the subject may have been measured or may be measured. The BMI of the subject may have been measured prior to administering the UIM-containing peptide and may be measured after administering the UIM-containing peptide. The subject may also suffer from renal disease, cardiovascular disease, diabetes, autoimmune disease, respiratory disease, neurodegenerative disease, liver disease, infectious disease, cancer or has or will undergo transplant. The method may further comprising treating said subject with a second weight reducing or weight regulating therapy. The administration may be intravenous, intra-arterial, intra-nasal, transdermal or oral, may be daily, every other day, weekly or monthly. The UIM-containing peptide may further comprise a cell targeting peptide, a cell penetrating peptide and/or a lipid-targeting domain. The cell targeting domain may comprise CKGGRAKDC (SEQ ID NO: 9), and/or the lipid targeting domain is membrane anchoring peptide. The UIM-containing peptide may comprise L amino acids, D amino acids, or a mixture of L and D amino acids. The may be about 18 to about 50 residues in length, such as precisely or about 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 residues in length.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the disclosure, and vice versa. Furthermore, compositions and kits of the disclosure can be used to achieve methods of the disclosure.

Throughout this application, the term "about" is used to indicate that a value includes the inherent variation of error for the device, the method being employed to determine the value, or the variation that exists among the study subjects.

The terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. As a result, a device or a method that "comprises," "has," "contains," or "includes" one or more elements possesses those one or more elements, but is not limited to possessing only those one or more elements or steps. Likewise, an element of a device or method that "comprises," "has," "contains," or "includes" one or more features possesses those one or more features, but is not limited to possessing only those one or more features.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIGS. 1A-M. UPI peptide exclusively homes to tumor vessels and inhibits tumor growth and metastasis. (FIG. 1A) Molecular modeling and schematic of UPI peptide (before proteolysis=SEQ ID NO: 42; after proteolysis=SEQ ID NO: 50); dotted line indicates site of in vivo proteolysis of iRGD.

(FIG. 1B) FUPI selectively enters and is retained in HUVEC$^{\alpha v \beta 3}$ cells, but not control HUVEC cells, at 15 hr, n=5. (FIG. 1C) Tissue distribution of FITC-UPI peptide in LLC tumor-bearing mice 4 h post i.v. injection. Tissues were fixed then FITC fluorescence captured by confocal microscopy; fluorescence intensity was quantified, n=4; *P<0.001. (FIG. 1D) Intravenous administration of UPI peptide inhibits subcutaneously implanted LLC tumor growth in a dose-dependent manner. CTR, 10 mg/kg, n=10; UPI, 2.5 mg/kg, n=8; UPI, 5 mg/kg, n=8; UPI, 10 mg/kg, n=10; *P<0.05; P<0.05, *P<0.01. (FIG. 1E) Intravenous administration of UPI peptide (10 mg/kg) inhibits growth of subcutaneously implanted B16 melanoma tumors, n=10 in each group; *P<0.05. (FIG. 1F) Intravenous administration of UPI peptide (10 mg/kg) inhibits subcutaneously implanted human glioma U87 tumor growth in immunodeficient SCID mice. n=8 in each group; *P<0.05. (FIG. 1G) Intraperitoneal administration of UPI peptide (20 mg/kg) inhibits prostate tumor growth in TRAMP models, n=15 in each group; *P<0.001. Right panel is a representative image. (FIG. 1H) UPI treatment attenuates frequency of metastasis to lungs and liver of TRAMP prostate cancer model, n=15 in each group; *, **P<0.001. H&E staining was shown for lungs and liver in control and UPI peptide treated TRAMP mice. Arrows indicate metastatic tumors. (FIG. 1I) Metastatic markers vimentin and snail were measured by Western blotting liver and lung tissue lysates, n>5 for each group. (FIG. 1J) Intraperitoneal administration of UPI peptide (20 mg/kg) in TRAMP mice at 20 weeks of age increases survival, n=20 in control group and n=18 in UPI peptide-treated group; P=0.0107. (FIG. 1K) UPI peptide treatment decreased frequency of metastasis to lymph nodes in B16 tumor-bearing mice post-surgical removal of primary tumors as revealed by anti-vimentin immunofluorescence staining (IF). (FIG. 1L) Representative images for lungs of control and UPI peptide-treated B16 tumor-bearing mice post-surgical removal of primary tumors. Right panels show IF staining for melanoma-specific marker, Melan-a. Number of tumor nodules present in lungs was greatly reduced by UPI treatment. (FIG. 1M) Western blotting analysis of lung tissue from control and UPI peptide-treated B16 tumor-bearing mice post-surgical removal of primary tumors, n>5 in each group.

FIGS. 2A-P. UPI peptide selectively disrupts epsin-VEGFR2 interaction and increases VEGFR2 signaling by specifically binding to VEGFR2 in vitro and in vivo. (FIG. 2A) UPI peptide treatment of lysates from 293T cells overexpressing HA-tagged epsin 1 and His-tagged VEGFR2 kinase domain (KD) greatly inhibits VEGFR2 KD co-immunoprecipitation of epsin 1, relative to control peptides, n=5. (FIG. 2B) Pretreatment with 10 µM UPI peptide increases VEGF-mediated (50 ng/ml, 5 min) phosphorylation and accumulation of VEGFR2 in cultured HUVEC$^{\alpha v \beta 3}$ cells, n=5. (FIG. 2C) UPI peptide increases VEGFR2-mediated downstream activation of PLC-γ and ERK in cultured HUVEC$^{\alpha v \beta 3}$ cells, n=5. (FIG. 2D) Biotinylated UPI peptide specifically targets VEGFR2, but not EGFR, FGFR1 or PDGFR-β, in biochemical pulldown assays using ex vivo LLC tumor lysates, n>5. (FIG. 2E) UPI peptide does not alter FGF, PDGF or EGF-mediated downstream signaling in HUVEC$^{\alpha v \beta 3}$ cells, n=5. (FIG. 2F) Therapeutic efficacy of UPI peptide is dependent on activated VEGFR2. Removal of VEGF by anti-VEGF antibody (1.5 mg/kg) or inactivation of VEGFR2 activity by VEGFR2 kinase inhibitor (0.5 mg/kg) abolished UPI peptide-mediated tumor inhibition, n=5 in each group; *P<0.001; n.s: no statistical difference. (FIGS. 2G-H) UPI peptide is specifically targeted to VEGFR2 in genetically modified animals deficient in endothelial epsins with homozygous or heterozygous VEGFR2 (FIG. 2G), or endothelial epsin deficient mice with restored Notch activity (FIG. 2H), n=5 tumors in each group. P value is indicated in each figure; n.s: no statistical difference. (FIG. 2J) Alignment of UIM sequences from endocytic proteins. Note: Q9, A13 and K16 are residues uniquely present in the epsin 1 UIM. Epsin-1=SEQ ID NO: 1; Hrs-A/B=SEQ ID NO: 51; Eps15-1=SEQ ID NO: 52; Eps15-2=SEQ ID NO: 53; Vps27-1=SEQ ID NO: 54; Vps27-2=SEQ ID NO: 55; Stam1-A/B=SEQ ID NO: 56; Stam2-A/B=SEQ ID NO: 57. (FIGS. 2K-L) Point mutations of Q9A, A13S and K16A in epsin UIM (FIG. 2K), or R1027 and R1080 in VEGFR2 (FIG. 2L), all attenuated the epsin 1-VEGFR2 interaction in 293T cells, n=4. (FIG. 2M) Mutant UPI (UPI-Mut) peptide (Q9A/A13S/K16A) failed to inhibit the epsin 1-VEGFR2 interaction, determined as described in FIG. 2A, n=5. (FIG. 2N) SPR analysis revealed significant increases in binding affinity of UPI peptide to VEGFR2 KD, compared to control or UPI-Mut peptide, n=4. (FIG. 2O) Compared to control peptide, UPI-Mut peptide reduces the tumor inhibitory effect in LLC tumor-bearing mice n>5 tumors in each group; **P<0.001. (FIG. 2P) UPI peptide, but not Eps15-UIM or Hrs-UIM containing peptides causes impaired tumor growth in LLC tumor-bearing mice, n>5 in each group. *P<0.001; n.s: no statistical difference.

FIGS. 3A-J. UPI peptide promotes in vitro and in vivo neoangiogenesis and disrupts tumor angiogenesis by stabilizing VEGFR2 signaling. (FIG. 3A) UPI peptide treatment causes increased cell proliferation in HUVEC$^{\alpha v \beta 3}$ cells, n=5. (FIG. 3B) UPI peptide treatment causes increased cell migration in HUVEC$^{\alpha v \beta 3}$ cells measured by "scratch" wound closure, n=4. (FIG. 3C) UPI peptide treatment increases tube formation of HUVEC$^{\alpha v \beta 3}$ cells in Matrigel plug assay,*P<0.05, n=4. (FIG. 3D-E) UPI peptide treatment increases in vivo angiogenesis in Matrigel plug assay, n=5; *, † CTR vs UPI in each group, P<0.001. (FIG. 3F) UPI peptide treatment increases retina neoangiogenesis in P6 pups, n=5; *P<0.001. (FIGS. 3G-H) UPI peptide treatment increases in vivo tumor angiogenesis. CD31 immunofluorescence (IF) staining for subcutaneously implanted LLC and U87 tumors (FIG. 3G). (FIG. 3H) Vessel density and diameter were quantified by averaging tumor vessels in at least 5 fields, n>5 tumors; *P<0.001. (FIG. 3I) UPI peptide treatment increases VEGFR2 expression in subcutaneous LLC or U87 tumors, n>5; *, † P<0.001. (FIG. 3J) UPI peptide treatment increases P-VEGFR2 in human U87 glioma tumor models analyzed by IF staining using anti-phospho-VEGFR2 antibody, n>5, *P<0.001.

FIGS. 4A-K. UPI peptide treatment produces dysfunctional and hyper-leaky tumor vessels, and retards tumor growth in orthotopic glioblastoma models. (FIG. 4A) UPI peptide treatment causes a significant increase in tumor vessel leakage. CTR or UPI peptides (10 mg/kg i.v. injection on alternating days) treated subcutaneous U87 tumor-bearing mice were perfused with FITC-Dextran for 10 min, and then tumors and major organs were harvested and fixed for CD31 staining. Representative images show FITC (green) and CD31 (red) immunofluorescence staining in tumors, n=5; *P<0.001; Scale bar: 100 µm. (FIG. 4B) UPI peptide treatment of subcutaneous U87 tumors reduces smooth muscle actin coverage around tumor vessels. Quantified by IF staining of α-SMA, n=5; *P<0.001; scale bar: 100 µm.

(FIG. 4C) UPI peptide treatment causes significant red blood cell leakage (blue arrows) from subcutaneous U87 tumor vessels (red dotted line) revealed by transmission electron microscopy (TEM) of semi-thin sections, n=5; scale bar: 50 µm. Red arrows indicate dying tumor cells. (FIG. 4D) UPI peptide treatment increases tumor hypoxia in subcutaneous U87 tumor tissues as measured by pimonidazole hydrochloride IF staining; n>5 in each group. For each tumor, a minimum of 5 fields were chosen for analysis, *P<0.001; scale bar: 100 µm. (FIG. 4E) UPI peptide does not cause vessel leakage in quiescent intestinal tissues. Determined as described in (FIG. 4A). Representative images show FITC (green) and CD31 (red) immunofluorescent staining of intestine, n=5; scale bar: 100 µm. (FIGS. 4F-H) Intravenous injection of UPI peptide (10 mg/kg) impairs orthotopic glioblastoma tumor growth (analyzed by MRI) (FIGS. 4F-G) and enhanced survival rate (FIG. 4H) of C57BL/6 mice bearing orthotopically implanted glioma GL261 tumor, n=10 in each group; *P<0.001; scale bar in (FIG. 4G): 3 mm. Anti-VEGF antibody (5 mg/kg) serves as a positive control, n=4. (FIG. 4I) UPI peptide treatment significantly increases tumor necrosis in orthotopic U87 tumor-bearing SCID mice. Comparison of MRI graphs between control (Day 18) and UPI peptide-treated (Day 35) U87 glioblastomas displayed severe necrosis and increased VEGFR2 levels in UPI peptide-treated tumor tissues of similar size. Arrows indicate tumors; lower panels show in situ VEGFR2 tracking analysis; green and red bars in (FIG. 4I) represent necrotic areas and VEGFR2 in glioblastoma, respectively, n=9 in each group; *, **P<0.001; scale bar: 3 mm. (FIG. 4J) UPI treatment significantly increases survival rate in human glioblastoma U87/SCID model, n=10 in each group; P<0.0001. (FIG. 4K) Molecular mechanisms proposed for the underlying therapeutic action of UPI. UPI competes with endogenous epsin to interfere with epsin-mediated downregulation of activated VEGFR2 in tumor endothelium, thus disrupting tumor angiogenesis leading to retarded tumor growth.

FIGS. 5A-D. UIM alignment and models of UIM-Ub, UPI-Ub and UPI-VEGFR2. (FIG. 5A) Alignment of human epsin UIM, mouse epsin UIM and yeast Vps27 UIM with UPI chimeric peptide (h/mEpsin1-UIM=SEQ ID NO: 1; h/mEpsin2-UIM=SEQ ID NO: 58; yVps27-UIM=SEQ ID NO: 59; UPI_peptide=SEQ ID NO: 50); (FIG. 5B) Ribbon diagrams show predicted models of yeast Vps27, epsin UIM and UPI peptide; (FIG. 5C) Ribbon diagrams show yeast Vps27 UIM interacts with ubiquitin (left), and models of human epsin UIM-Ub complex (middle) and UPI-Ub complex (right). The NMR structure of yeast Vps27 UIM-Ub and x-ray structure of ubiquitin were taken from the Protein Data Bank, entries 1Q0W and 1UBQ, respectively. The top scoring models of epsin UIM and UPI peptide were selected and docked into ubiquitin, respectively. The models with high scores and good topologies were shown. Yeast Vps27 UIM, epsin UIM and UIM of UPI peptide interact with ubiquitin in a highly similar manner. (FIG. 5D) Molecular modeling suggested that UPI peptide directly binds to VEGFR2. UPI peptide binding in the putative binding pocket is highlighted. Figures were prepared using PyMol.

FIGS. 6A-E. Targeting and localization of UPI peptides in cultured HUVEC$^{\alpha v \beta 3}$. (FIGS. 6A-C) HUVECs were co-transfected with integrins αv and β3 plasmids by electroporation (Nucleofactor device, Lonza), generating HUVEC$^{\alpha v \beta 3}$ cells. 10 µM FUPI (FITC-conjugated UPI) peptide was added to HUVEC$^{\alpha v \beta 3}$ cells or pcDNA transfected control HUVECs. Expression of αvβ3 was measured by FACS (FIGS. 6A-B) and Western blot (FIG. 6C) 15-hr post-transfection; (FIG. 6D) FUPI showed PM enrichment (left three panels), while AP-UIM showed random cytosolic localization (right panel); Scale bar: 10 µm; (FIG. 6E) AP-UIM peptides non-selectively entered HUVEC or HUVEC$^{\alpha v \beta 3}$ cells; scale bar: 100 µm.

FIGS. 7A-C. Pharmacokinetics of UPI peptide in ex vivo plasma and tumor vessels. (FIG. 7A) Biotinylated-UPI peptide was incubated in ex vivo plasma at 1 µg/ml concentration. The remaining biotin-labeled UPI peptide was quantified by ELISA as indicated at different time point, n=5; (FIG. 7B) FUPI peptide (10 mg/kg, one injection) was i.v.-injected into mice bearing B16 tumors. A time course was scheduled to sacrifice mice as indicated from 2-48 hrs. FUPI peptide positive vessels gradually decreased but sustained a significant FUPI peptide positive percentile up to 48 hrs post injection; Scale bar: 100 µm; (FIG. 7C) Quantification of percent FUPI peptide positive vessels relative to total CD31 positive vessels in FIG. 7B, n=5.

FIGS. 9A-B. UPI peptide administration significantly inhibits prostate tumor growth in TRAMP model and a comparison of therapeutic efficacy of AP-UIM, UI and UPI in LLC tumor model. (FIG. 9A) Control (CTR) or UPI peptide was i.p.-injected (20 mg/kg, every-other-day) from 20-35 weeks in normal and TRAMP animal models. Representative images of H&E stained vesicle in normal, TRAMP and TRAMP-UPI mice, n=18. Images show reduced tumors after UPI treatment; scale bar: 100 µm; (FIG. 9B) Comparison of therapeutic efficacy among AP-UIM, UI, UPI and CTR peptides in LLC tumor models, n>5; P values are indicated in the figure.

FIGS. 10A-E. UPI administration significantly inhibits epsin 1-VEGFR2 interaction, disables VEGFR2 endocytosis and increases VEGF downstream effector signaling. (FIG. 10A) UPI peptides made of D- or L-isomer amino acids had similar inhibitory effects on epsin 1-VEGFR2 interaction by co-IP analysis in 293T cells co-expressing VEGFR2 kinase domain (His-tag) and Epsin 1 (HA-tag) in biochemical peptide competition assays, n=5; (FIG. 10B) UPI peptide treatment blocked Epsin 1-VEGFR2 interaction in endogenous HUVEC$^{\alpha v \beta 3}$, n=5; *P<0.001; (FIG. 10C) UPI peptide treatment increased VEGF-stimulated P-PLC-γ and P-ERK in HUVEC$^{\alpha v \beta 3}$. Corresponding to FIG. 2C. *, ‡, UPI vs Control; P<0.001; (FIG. 10D) UPI peptide disabled VEGFR2 endocytosis measured by biotin-labeled-VEGF internalization in HUVEC$^{\alpha v \beta 3}$ cells visualized by confocal microscopy, n=5. At 4° C., labelled VEGF was bound to surface VEGFR2. After incubating at 37° C. for 15 min, VEGF-VEGFR2 complex was internalized. In control samples, a significant endocytosis was observed, while in UPI-treated samples, endocytosis of the VEGF-VEGFR2 complex was inhibited. Thus majority of VEGF-VEGFR2 was retained on the plasma membrane (PM). To further support this, the inventors used acidic buffer to wash away VEGF on the PM after incubation at 37° C. As shown, in the acidic-washed control samples, regular endocytosis was observed. However, in the UPI peptide-treated cells, VEGFR2 endocytosis was minimal; Scale bar: 10 µm; (FIG.

Figure 2I:
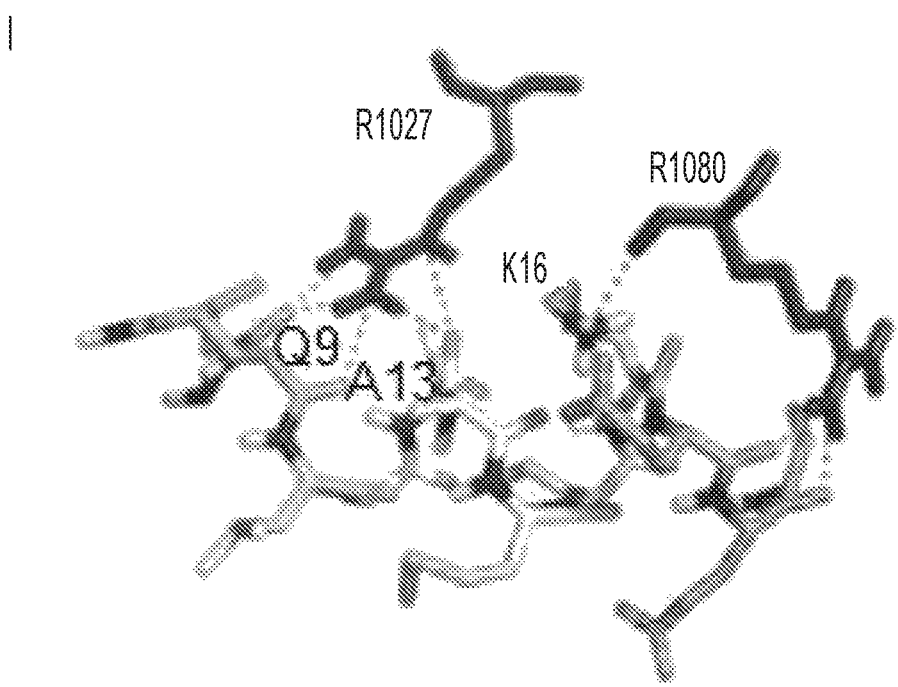
(FIG. 2I) Interacting residues predicted to mediate epsin UIM docking in a putative binding pocket of a ubiquitinated VEGFR2 kinase domain. Rainbow: epsin UIM, blue: VEGFR2.

10E) UPI peptide increases VEGFR2 retention on the PM of HUVEC$^{\alpha v \beta 3}$ cells revealed by FACS analysis, n=4; *P<0.05.

FIGS. 11A-K. UPI peptide is a specific VEGFR2 modifier but does not affect other major angiogenic factor signaling pathways in vitro or in tumors. (FIGS. 11A-B) Anti-VEGF antibody neutralizes VEGF/UPI peptide-mediated augmentation of VEGFR2 signaling. HUVEC$^{\alpha v \beta 3}$ cells were pre-treated with 10 µM control or UPI peptide for 15 hours. Cells were then starved for 3 hours, followed by pre-treatment with anti-VEGF antibody (200 µg/ml) for 1 hour and then stimulated by VEGF (50 ng/ml) for 5 min. Cell lysates were subjected to Western blot using antibodies as indicated in (FIG. 11A); (FIG. 11B) Quantification of P-VEGFR2 from FIG. 11A), n=4; P value of statistical analysis is indicated in the figure; (FIG. 11C) Binding affinity of biotinylated-UPI peptide to VEGFR2, FGFR1 PDGFR-β and EGFR determined by binding affinity-ELISA assay in HUVEC$^{\alpha v \beta 3}$ cells. Note that UPI peptide did not interact with FGFR1, PDGFR-β or EGFR, n=5; *P<0.001; n.s: no statistical difference. UPI peptide bound VEGFR2 only; n=5, *P<0.05; (FIGS. 11D-F) Quantifications of phosphorylated PLC-γ, AKT and ERK relative to total under different stimulations in FIG. 2E; (FIG. 11G) Western blot analysis of VEGFR2, EGFR1, TGFβR1 and PDGFR-β in representative control (CTR) or UPI peptide-treated B16 melanoma tumors; (FIG. 11H) Quantification of protein expression in FIG. 11G, n=5; *P<0.05; (FIG. 11I) Expression of angiogenic receptors and P-VEGFR2 in control (CTR) or UPI peptide-treated U87 glioma mouse tumors; (FIGS. 11J-K) UPI peptide treatment did not change the expression of epsin 1 and epsin 2 in HUVEC$^{\alpha v \beta 3}$ cells or U87 glioma tumors, n=5.

FIGS. 12A-D. UPI peptide does not affect VEGFR1, VEGFR3 or Notch signaling in endothelial cells. (FIG. 12A) HUVEC$^{\alpha v \beta 3}$ cells were treated with UPI or control (CTR) peptides. Prior to lysis, cells were stimulated with VEGF for 5 min. Lysates were analyzed by Western blot using anti-VEGFR1 and VEGFR3 antibodies; (FIG. 12B) HUVEC$^{\alpha v \beta 3}$ cells were treated as in FIG. 12A, then lysates were immunoprecipitated with anti-VEGFR1 antibody and phosphorylation analyzed by Western blotting using 4G10 antibody; (FIG. 12C) Mouse primary ECs (MEC) were isolated, cultured, and co-transfected with plasmids of αv and β3, pre-treated with 10 µM DAPT (γ-secretase inhibitor) or DMSO (vehicle) for 24 hrs, and then treated with UPI or CTR peptides at 25 µM for an additional 16 hrs. Cell lysates were Western blotted with anti-NICD and Dll4 antibodies; (FIG. 12D) Quantification of NICD expression in (C), n=4.

FIGS. 13A-D. Strategy for generating genetically modified animal models. Mice were crossed as shown to establish genetically modified animal models. Genotyping and selection of mice for breeding are routinely performed using standard procedures. (FIG. 13A) WT-Flk; (FIG. 13B) EC-iDKO; (FIG. 13C) EC-iDKO-Flk; (FIG. 13D) EC-iDKO-Notch.

Figure 14A:
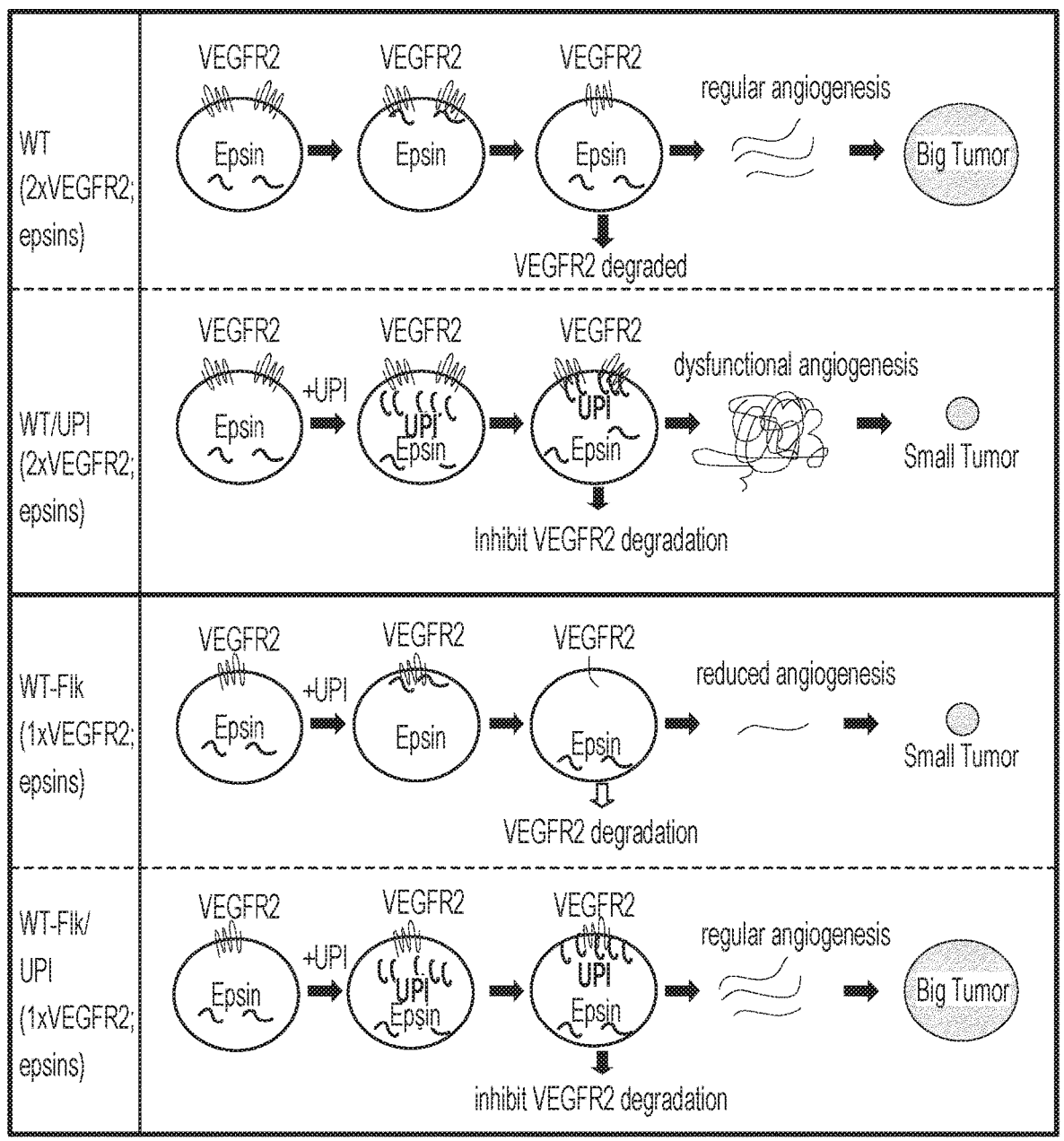

FIG. 14A. UPI peptide therapeutic concept and targeting specificity in genetically modified mice harboring a loss in VEGFR2 allele. Therapeutic efficacy of UPI peptide is predicted to be dependent on the expression level of VEGFR2 in vivo (WT-Flk); Less VEGFR2 normalizes UPI peptide effect on tumor angiogenesis.

Figure 14B:
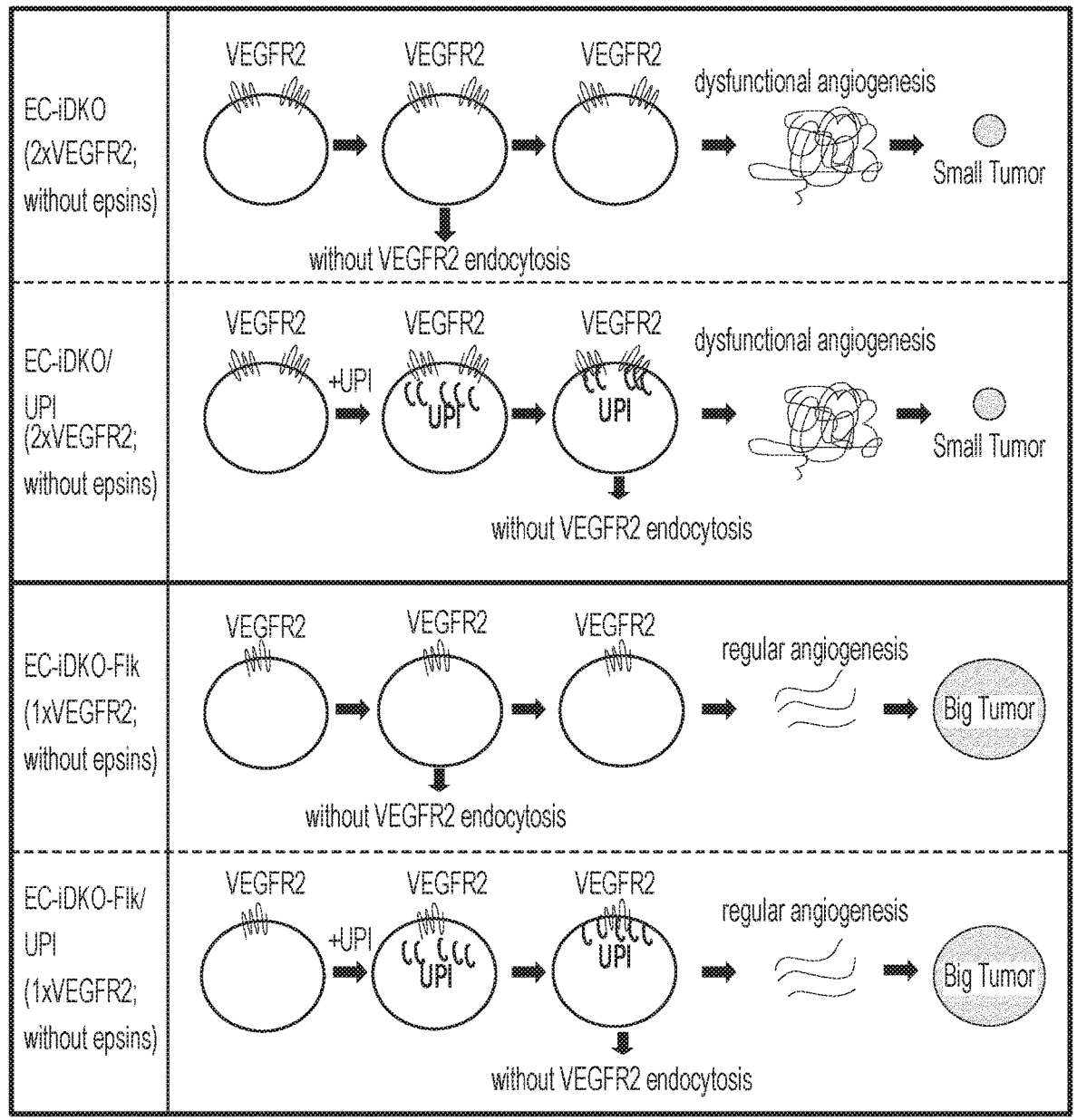

FIG. 14B. UPI peptide therapeutic concept and targeting specificity in genetically modified mice harboring epsin deficiency and a loss in VEGFR2 allele. Therapeutic efficacy of UPI peptide is predicted to be dependent on the expression level of epsins in vivo (EC-iDKO or EC-iDKO-Flk); Loss of epsins impairs UPI peptide effect on tumor angiogenesis.

FIGS. 15A-D. Biochemically, triple mutation of UPI peptide significantly attenuates binding to VEGFR2 in pull-down assay using ex vivo tumors. (FIGS. 15A and 15C) LLC (FIG. 15A) or Glioma GL261 (FIG. 15C) subcutaneous tumors removed from C57BL/6 mice were homogenized in lysis buffer containing 50 mM Tris-HCl pH 7.5, 150 mM NaCl, 0.05% NP-40, 10% glycerol, 1× cocktail (Roche) and 20 mM NEM (N-ethylmaleimide). Lysate protein concentration was determined by BCA kit (Pierce). 2 mg of total lysate was co-incubated with 50 µg of either biotinylated UPI peptide, UPI mutant (UPI-Mut) peptide or control peptide. Neutri-Avidin beads (Invitrogen) were then added to pulldown biotinylated UPI or control peptide. These beads were subjected to two washes with lysis buffer and two washes with ½ lysis solutions. Afterwards, beads were boiled in 2× loading buffer and the supernatant was used for Western blot analysis of VEGFR2, PDGFR-β, EGFR and FGFR1; (FIGS. 15B and 15D) Quantification of peptide pulldown of VEGFR2 in LLC (FIG. 15B) and Glioma GL261 (FIG. 15D) tumors, n=5; P values are indicated in the figures.

FIGS. 16A-D. UPI peptide increases tumor vessel permeability and leakage by generating fenestration and open junction between endothelial cells revealed by transmission electron microscope (TEM) and semi-thin sectioning. Tumors collected from UPI peptide treated U87/SCID animal models were prepared for TEM analysis. (FIG. 16A) Representative image of UPI peptide treated U87 tumor depicting fenestration in the endothelium; indicated by black arrows; (FIG. 16B) Representative image of UPI peptide treated U87 tumor showing platelet aggregations in an open junction (red arrow) between two ECs. RBC: red blood cell; P: platelet; EC: endothelial cells; (FIG. 16C) Representative image taken from U87 control tumor, showing red blood cells are inside vessels; (FIG. 16D) Representative image of UPI peptide treated U87 tumor showing increased permeability and significant RBC leakage in semi-thin sections (red arrows); n=5 for all data; scale bar (a, b): 500 nm; (c, d): 100 µm.

FIG. 17. UPI peptide injection does not cause vessel leakage in other major organs (non-tumor organs). B16-melanoma tumor bearing mice were i.v.-injected with control or UPI peptides for 16 days (dosage: 10 mg/kg, every other day). Mice were perfused with FITC-Dextran injection for 10 min. Tumors and other major organs were harvested and fixed for CD31 staining. FITC (green) and CD31 (red) was visualized simultaneously by confocal microscopy. Data showing no leakage in all examined organs; n=3 in all groups; scale bar: 100 µm.

FIGS. 18A-B. UPI peptide administration significantly inhibits orthotopic human glioma U87 tumor growth. (FIGS. 18A-B) UPI peptide treatment (10 mg/kg, i.v. injection every-other-day) inhibits orthotopically implanted human glioma U87 tumor growth in immunodeficient SCID mice. n=10 in all groups; *P<0.05. Representative MRI scans of terminal mice are shown in FIG. 18B.

FIGS. 19A-H. EC-specific deletion of epsins attenuates atherosclerosis in ApoE-deficient mouse model. (FIG. 19A) Deletion of epsins in endothelium significantly reduced atherosclerotic lesion in ApoE$^{-/-}$ animal models (root); n>5 in each group. (FIG. 19B) Deletion of epsins in endothelium significantly reduced atherosclerotic lesion in carotid animal models (root); n>5 in each group. (FIG. 19C) Deletion of epsins in endothelium significantly reduced atherosclerotic lesion in ApoE$^{-/-}$ animal models (Arch); n>5 in each group. (FIG. 19D) Macrophage infiltration in EC-iDKO/ApoE$^{-/-}$ mice is significantly reduced, n>5 in each group. (FIGS. 19E-F) Resident macrophage and immune cells in aortic arch are drastically reduced, n>5 in each group. (FIG. 19G) EC-dependent relaxation is significantly improved in EC-iDKO/ApoE$^{-/-}$ mice; n=3 in each group. (FIG. 19H) Plasma glucose and lipid profile are not affected in the loss of epsin mice; n>5 in each group.

FIGS. 20A-E. Epsins are upregulated in EC and promotes ER stress. (FIG. 20A). Expression of epsins is upregulated in MAEC treated by oxLDL for 24 hrs at 100 μg/ml. (FIG. 20B) In the arch of atherosclerosis patients, expression of epsins is upregulated. (FIG. 20C) Deletion of epsins in EC significantly attenuated ER stress in immunofluorescent staining, n>5. (FIG. 20D) Quantification for FIG. 20C. (FIG. 20E) Loss of epsins in EC of ApoE-deficient background attenuated ER stress and increase survival signaling.

FIGS. 21A-F. Epsins regulate intracellular ER homeostasis by destabilizing ER protein IP3R1. (FIG. 21A) IP-Mass spec identified IP3 Receptors and cytoskeletal and stress response proteins binds to Epsins. (FIG. 21B) Loss of epsins in EC stabilizes IP3 receptor1 degradation induced by athero-prone substances cholesterol, 7KC and oxLDL. (FIG. 21C) IP3R1 degradation mediated by athero-prone substances is via proteasome system. (FIG. 21D) Deletion of epsins stabilize IP3R1 in arotic roots. (FIG. 21E) Deletion of epsin1 in MAEC stabilize IP3R1. (FIG. 21F) In atherosclerosis patients, IP3R1 expression in aortic arch is downregulated.

FIGS. 22A-D. Downregulation of IP3R1 by epsins augments ER stress-mediated inflammation in Endothelium. (FIG. 22A) Deletion of IP3R1 augments ER stress mediated by athero-prone substances. (FIG. 22B) Inhibition of ER stress by 4-PBA protected athero-prone substances mediated ER stress due to loss of IP3R1. (FIG. 22C) Loss of epsins auguments NF-kB signaling. (FIG. 22D) NF-kB augmentation can be prevented by ER stress inhibitor 4-PBA.

FIGS. 23A-E. Loss of epsins attenuates EC activation and inflammatory signaling and inflammation readout. (FIG. 23A) Expression of selectins and adhesion molecules is attenuated in EC-iDKOMAEC by RT-PCR. (FIG. 23B) Adhesion binding of epsin-deficient MAEC versus WtMAEC using GFP-labelled macrophage (wt). (FIG. 23C) P-selectin expression and macrophage infiltration are downregulated in EC-iDKO aortic roots. (FIG. 23D) Interferon-gamma expression in MAEC deficient epsins is inhibited in RT-PCR analysis. (FIG. 23E) Circulating TNF and IL-6 are significantly reduced in EC-iDKO mice.

FIGS. 24A-E. IP3R1 interacts with epsins to promotes degradation. (FIG. 24A) IP3R1 and Epsin1 co-localization in IF staining. Cells were treated with oxLDL (200 μg/ml) for 1 hour. (FIG. 24B) IP3r1 interacts with Epsin1 in MAEC. (FIG. 24C) Epsin1 interacts with IP3R1 in MAEC. (FIG. 24D) Deletion of UIM domain in epsin1 significantly attenuated Epsin1-IP3r1 interaction. (FIG. 24E) Truncations of IP3R1 suggest that N-terminal of IP3R1 is the key region for IP3R1-Epsin 1 interaction.

FIGS. 25A-E. Therapeutic potential in atherosclerosis animal models. (FIG. 25A) Targeting lyp-UIM peptide to atheroma by FITC conjugated peptide. (FIG. 25B). In carotid mouse model, Lyp-UIM peptide (CGNKRTRGCS-GEEELQLQLALAMSKEE; SEQ ID NO: 5) significantly inhibited atherosclerosis development and reduced macrophage infiltration. n>5 in each group. (FIG. 25C) Quantification for FIG. 25B, red bars represent lesion area by percentile; green bars represent macrophage percentile in different treatment. P values is indicated in the graphs. (FIG. 25D) Lyp-UIM peptide treatment significantly attenuated atherosclerotic lesion development (root) in ApoE$^{-/-}$ mouse models. (FIG. 25E) Lyp-UIM peptide treatment significantly attenuated atherosclerotic lesion development (arch) in ApoE–/–mouse models.

FIGS. 26A-B. Epsins-deficient mice exhibit resistance to body weight gain on HFD. (FIG. 26A) WT and iDKO mice on HFD or ND. (FIG. 26B) Representative WT and iDKO mice fed on HFD and ND. Results taken from female mice. Male mice show similar trend. n=10 in each group. P<0.001.

FIGS. 27A-C. Epsins are upregulated in obesity models of Lep–/– mice (ob/ob) or HFD-induced obese mice. Epsin expression revealed by western blot (FIGS. 27A-B) and immunofluorescent staining (FIG. 27C).

FIGS. 28A-D. Deficiency of epsins significantly improves lipid metabolism accompanying increased whole body insulin sensitivity. (FIG. 28A) Reduced white adipose size (μm$^2$) revealed by histology staining (upper) and statistical analysis (bottom). (FIG. 28B) Oil Red O staining of triglyceride (TG) content in liver. (FIG. 28C) Insulin sensitivity is greatly increased in epsin-deficient iDKO mice revealed by Insulin tolerance test (ITT-top) and Glucose tolerance test (GTT-bottom). (FIG. 28D) Glucose levels in non-fasting (top) and fasting mice (bottom). n=8.

Figure 29:
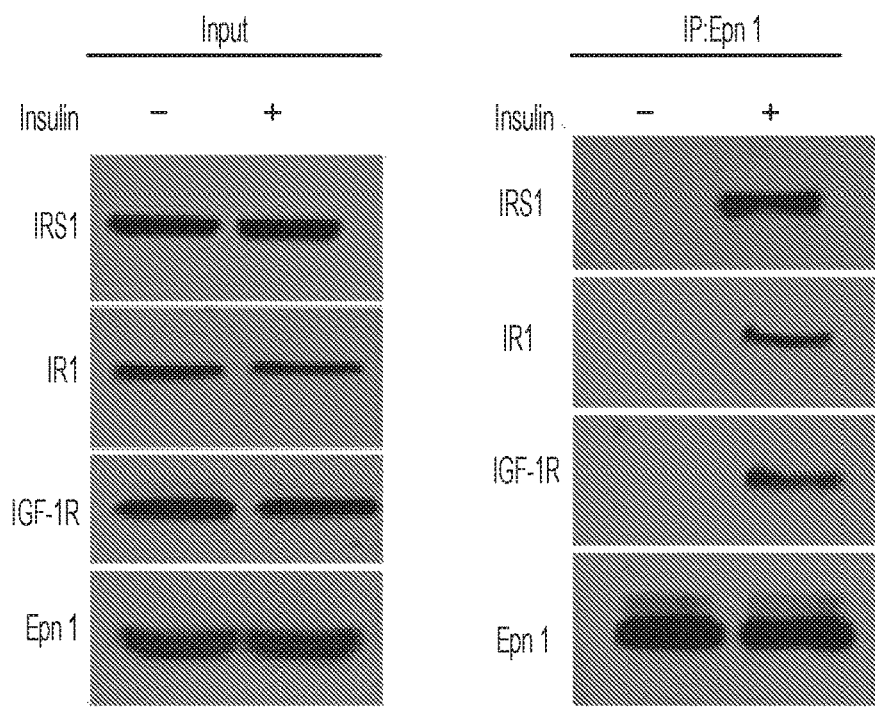

FIG. 29. Epsin 1 binds IRS1, insulin and insulin-like growth factor receptor in IP analysis in 3T3 L1 pre-adipocytes.

FIG. 30. Epsins promote adipocyte differentiation in 3T3-L1 cell line.

FIGS. 31A-C. Loss of epsins in adipocytes (aP2-cre) significantly attenuated fat pad development after HFD feeding. (FIG. 31A) Representative WT and aP2-cre mice. (FIG. 31B) Growth curve of BW gain, n=10 in each group. (FIG. 31C) Representative white adipose tissue. n=8-10; P<0.001.

FIG. 32A-B. Loss of epsins in fat tissues attenuates Akt and mTOR signaling.

FIGS. 33A-C. Administration of epsin UIM peptide significantly attenuates body weight gain in HFD fed mice. (FIG. 33A) Male and (FIG. 33B) Female mice, n=8 in each group; P<0.001. (FIG. 33C) Representative image of PBS or AP-UIM peptide administration for 3 months.

FIGS. 34A-C. Adipocyte-specific deletion of epsin significantly attenuated fat pad development after HFD feeding. (FIG. 34A) Representative WT and aPe-cremice. (FIG. 34B) Growth curve of BW gain, n=10 in each group. (FIG. 34C) Representative white adipose tissue.

FIGS. 35A-C. Administration of epsinUIM peptide significantly attenuates body weight gain in HFD fed mice. (FIG. 35A) Male and (FIG. 35B) Female mice, n=8 in each group. (FIG. 35C) Representative image of PBS or UIM peptide administration for 3 months.

FIGS. 36A-B. Strategy for generating EC-DKO/ApoE$^{-/-}$ (related to FIGS. 19A-H). Mice were crossed as shown to establish EC-DKO/ApoE$^{-/-}$. Genotyping and selection of mice for breeding are routinely performed using standard procedures. (FIG. 36A) EC-DKO; (FIG. 36B) EC-DKO/ApoE$^{-/-}$.

FIGS. 37A-J. Epsins are upregulated in atheroma; MAEC isolation/characterization; LDL scavenger expression in MAEC and ER stress markers in human atherosclerosis samples (related to FIGS. 20A-E). (FIGS. 37A-B) Epsins are upregulated in athroma. (FIGS. 37C-G) MAEC isolation and characterization. (FIG. 37C) Aortic segment was cultured in metrigel, showing EC-formed networks; (FIG. 37D)

isolated MAEC; (FIG. 37E) Networks formed by the isolated MAEC in Metrigel; (FIG. 37F) VEGFR2 expression in isolated MAEC; (FIG. 37G) co-staining of endothelial marker CD31 or vWF with α-SMA antibodies in isolated MAEC; (FIG. 37H) loss of epsins did not change the expression of scavenger receptors and LDL uptake in MAEC; (FIGS. 37I-J) ER stress markers in endothelium are upregulated in human atherosclerosis patients, n=4.

FIGS. 38A-B. Loss of epsins co-incidentally attenuated oxidative stress revealed by the reduction of ROS/RNS (related to FIGS. 22A-D). (FIG. 38A) IF staining of 3-NT for RNS; (FIG. 38B) IF staining of Ox-LDL for ROS.

Figure 39:
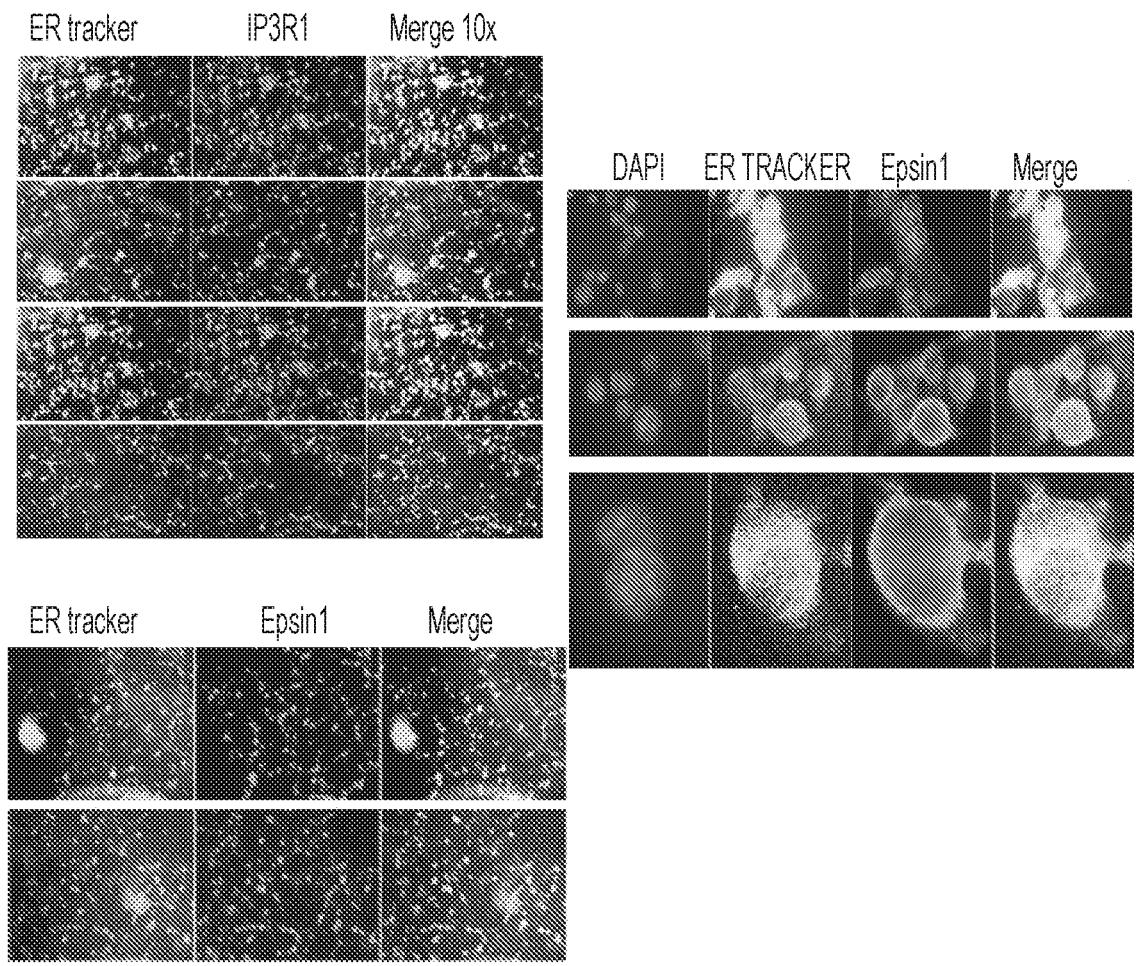

FIG. 39. IP3R1 and epsin colocalization in inflammatory condition. MAEC were treated by oxLDL (200 µg/ml) for 1 hour, ER tracker was loaded and followed by IF staining with IP3R1 antibody (related to FIGS. 24A-E).

DESCRIPTION OF ILLUSTRATIVE EMBODIMENTS

As stated above, epsins, via their ubiquitin interacting motif (UIM), recognize and recruit ubiquitinated VEGFR2 at the plasma membrane to clathrin-coated pits for internalization and subsequent degradation, thereby reducing VEGF signaling (Pasula et al., 2012). In this capacity, epsin loss exacerbated VEGF signaling, disrupted tumor angiogenesis and inhibited tumor progression (Pasula et al., 2012). This counter-intuitive finding that exacerbated tumor angiogenesis can actually inhibit tumors prompted us to search for a new strategy to combat human cancer by specifically disrupting epsin-mediated downregulation of VEGFR2 signaling in tumor endothelium. Given that the epsin UIM sequence is highly conserved among human and mouse epsins 1 and 2 (FIG. 5A), and that epsin UIM is critical for epsin-VEGFR2 binding (Pasula et al., 2012), the inventors wondered whether epsin UIM may be a central element in epsin function and, therefore, a potential target for clinical applications.

Thus, the inventors adopted a novel strategy in designing a tumor endothelium-targeting chimeric peptide (UPI) for the purpose of inhibiting endogenous tumor endothelial epsins by competitively binding activated VEGFR2. UPI peptide specifically targets tumor endothelial VEGFR2 through an unconventional binding mechanism driven by unique residues present only in the epsin ubiquitin interacting motif (UIM) and VEGFR2 kinase domain. UPI peptide increases VEGF-driven angiogenesis and neovascularization but spares quiescent vascular beds. Further, UPI peptide markedly impairs functional tumor angiogenesis, tumor growth and metastasis, resulting in a significant increase in survival. Equipped with localized tumor endothelium-specific targeting, this UPI peptide provides an effective alternative therapy for cancer. These and other aspects of the disclosure are described in detail below.

The inventors also provide compelling evidence that epsins play a critical role in promoting atherogenesis through the attenuation of leukocyte-endothelial interaction and inflammation in the atherogenetic initiation. The accelerated degradation of IP3R1 and increased ER stress-dependent inflammation facilitated by epsins may play a key role in atherosclerosis progression. These findings implicate a potential new therapeutic strategy for atherosclerosis treatment.

Finally, the inventors show data here that demonstrate epsin-deficient mice are resistant to high fat diet (HFD)-induced body weight (BW) gain. Significant reductions in fat mass contributed primarily to the loss of BW, suggesting an important regulatory role for epsins in the control of adiposity. Consistently, deletion of epsins in adipocyte using aP2-cre recombinase significantly reduced fat pads similar to HFD fed iDKO mice. Downregulation of epsins in 3T3-L1 cell line impaired adipocyte differentiation in vitro. Further analysis suggests that epsin binds to the complex of insulin receptor substrate (IRS1), insulin receptor (IR) or/and insulin-like growth factor receptor (IGF-1R) required for white and brown adipocyte differentiation and mTOR signaling-mediated lipogenesis. While the underlying molecular mechanisms responsible for epsin-mediated insulin signaling in adipocyte differentiation and lipid metabolism are completely unknown, it is clear that they have a significant affect on these important disease-related processes.

1. EPSINS AND UIM PEPTIDES

A. Epsins

Epsins are a family of endocytic clathrin adaptors and ubiquitin-binding proteins (Chen et al., 1998; Chen & De Camilli, 2005; Messa et al., 2014) with emerging importance in human disease (Coon et al., 2011 and Tessneer et al., 2013a). Despite abnormally high epsin expression in tumor tissues (Coon et al., 2011; Tessneer et al., 2013a; Tessneer et al., 2013b), its pro-cancer role remains elusive. Epsins are important in creating the needed membrane curvature and are involved in membrane deformations like endocytosis and block vesicle formation during mitosis. Structurally, at the N-terminus is an ENTH domain that binds phosphatidylinositol (Kerbel, 2008; Weis & Cheresh, 2011)-bisphosphate, a common lipid in biological membranes. This also is a possible site for cargo-binding. In the middle of the sequence are two UIM's (ubiquitin-interacting motifs). The C-terminus contains multiple binding sites, such as those for clathrin and AP2 adaptors.

Global deletion of both epsins 1 and 2 is embryonically lethal in mice (Chen et al., 2009), but post-natal endothelial cell-specific deletion of epsins produces adult mice with no gross physiological defects in quiescent vessels (Pasula et al., 2012; Tessneer et al., 2014). These mice did however exhibit altered tumor angiogenesis comprised of highly disorganized, non-productive and hyper-permeable tumor vasculature that resulted in inhibition of tumor growth (Pasula et al., 2012). The vascular dysfunction responsible for the profound tumor resistant phenotype was a result of impaired VEGFR2 internalization and degradation, resulting in failed down-regulation of VEGF signaling (Pasula et al., 2012; Tessneer et al., 2014). VEGF stimulates VEGFR2 internalization and degradation in part by inducing VEGFR2 ubiquitination (Pasula et al., 2012).

Epsin 4, which encodes the protein Enthoprotin (now known as Clathrin Interactor 1, or CLINT1) has been shown to be involved in the genetic susceptibility to schizophrenia in four independent studies. A genetic abnormality in CLINT1 is assumed to change the internalization of neurotransmitter receptors in the brains of people with schizophrenia.

B. UIMs

The recognition of ubiquitylated proteins is frequently mediated by conserved ubiquitin binding modules, which include the ubiquitin interacting motif (UIM). UIM permits binding of molecules containing such motifis to ubiquitin. UIM was originally identified based upon studies of the S5a subunit of the 19 S regulator in the human 26 S proteasome. Biochemical and mutational analyses revealed two copies of a ~30-residue sequence motif (initially denoted pUbS) that can bind ubiquitylated protein and polyubiquitin chains. The pUbS motifs have hydrophobic core sequences composed of alternating large and small residues (Leu-Ala-Leu-Ala-Leu (SEQ ID NO: 10)) that are flanked on both sides by patches of acidic residues. A more general definition of UIM, found in a number of different proteins that function in a variety of biological pathways, provides that UIM contains a 16 residue sequence corresponding to the consensus: X-Ac-Ac-Ac-Ac-Hy-X-X-Ala-X-X-X-Ser-X-X-Ac (SEQ ID NO: 11), where Hy represents a large hydrophobic residue (typically Leu), Ac represents an acidic residue (Glu, Asp), and X represents residues that are less well conserved.

UIMs are particularly prevalent in proteins that function in the pathways of endocytosis and vacuolar protein sorting, which serve to sort membrane-associated proteins and their cargo from the plasma membrane (or Golgi) for eventual destruction (or localization) in the lysosome (yeast vacuole). Endocytic proteins that contain UIMs include the epsins, including Eps15 and Eps15R. These proteins are required for endocytosis of receptor: ligand complexes, including the complex of the epidermal growth factor (EGF) with its receptor (EGFR). UIMs can both bind ubiquitin and also direct protein ubiquitylation, although the relationship between these two activities is not yet fully understood.

C. UIM Peptides

A UIM peptide according to the present disclosure is generally a small polypeptide having no more than about 50 residues, more typically no more than about 20 residues, such as 20- or 30-40 residues in length, including 18, 19, 20, 21, 22, 23, 24, 25, 26, 27, 28, 29, 30, 31, 32, 33, 34, 35, 36, 37, 38, 39 and 40 and ranges made from each of these numbers.

Also contemplated are peptides containing other functional domains, such as cell targeting domains (e.g., CKGRAKDC (SEQ ID NO: 9)) and lipid binding domains, e.g., lyn kinase (MGCIKSKRK (SEQ ID NO: 4)), integrin binding peptide, e.g., IRGD (CRGDKGPDC (SEQ ID NO: 3)) (see Tables A-C).

TABLE A

Cell Penetrating Peptides*

| Peptide | Origin | Sequence |
|---|---|---|
| Protein-derived | | |
| Penetratin | Antennapedia (43-58) | RQIKIWFQNRRMKWKK (SEQ ID NO: 12) |
| Tat peptide | Tat (48-60) | GRKKRRQRRRPPQ (SEQ ID NO: 13) |
| pVEC | Cadherin (615-632) | LLIILRRRIRKQAHAHSK (SEQ ID NO: 14) |
| Chimeric | | |
| Transportan | Galanine/Mastoparan | GWTLNSAGYLLGKINLKALA ALAKKIL (SEQ ID NO: 15) |
| MPG | HIV-gp41/SV40 T-antigen | GALFLGFLGAAGSTMGAWSQ PKKKRKV (SEQ ID NO: 16) |
| Pep-1 | HIV-reverse transcriptase/SV40 T-antigen | KETWWETWWTEWSQPKKKR KV (SEQ ID NO: 17) |
| Synthetic | | |
| Polyarginines | Based on Tat peptide | $(R)_n$; $6 < \underline{n} < 12$ |
| MAP | de novo | KLALKLALKALKAALKLA (SEQ ID NO: 18) |
| $R_6W_3$ | Based on penetratin | RRWWRRWRR (SEQ ID NO: 19) |

*Cherine Bechara and Sandrine Sagan, FEBS Letters, 587(12): 1693-1702, 2013

TABLE B

Homing peptides (HPs) conjugated to cell-penetrating peptides (CPPs)**

| Sequence (no. of amino acids) | Name | Mode of action | Target tissue | SEQ ID NO: |
|---|---|---|---|---|
| GRKKRRQRRRPPQ (13) | TAT | CPP | All cells | 13 |
| LLIILRRRIRKQAHAHSK (18) | pVEC | CPP | All cells | 14 |
| FCDGFYACYKDV (12) | ANHP | HP | Breast, ovarian and colon cancers | 20 |
| lgaswhrpdkcclgyqkrplp (21) | DIV1 | HP | Lymphoma cells | 21 |
| lgaswhrpdk (10) | DV3 | HP | Lymphoma cells | 22 |

TABLE B-continued

Homing peptides (HPs) conjugated to cell-penetrating peptides (CPPs)**

| Sequence (no. of amino acids) | Name | Mode of action | Target tissue | SEQ ID NO: |
|---|---|---|---|---|
| CPGPEGAGC (9) | PEGA | HP | Breast vasculature and tumors, premalignant breast tissue | 23 |
| CREKA (9) | | HP | Breast adenocarcinoma cells (MCF7) | 24 |

**-Nina Svensen, Jeffrey G.A. Walton, Mark Bradley, *Trends Pharmological Sci.*, 33(4): 186-192, 2012

TABLE C

Cell Penetrating Homing Peptides

| Sequence (no. of amino acids) | Name | Target tissue | SEQ ID NO: |
|---|---|---|---|
| CTPSPFSHC (9) | TCP-1 | Colorectal cancer | 25 |
| SFHQFARATLAS (12) | HAP-1 | Synovial cells | 26 |
| HIQLSPFQSWR (11) | HAP-2 | Synovial cells | 27 |
| LKKP (4) | | Myeloid leukemia cells (K562) | 28 |
| EPKK* (4) | | Embryonic stem cells | 29 |
| ELK*K* (4) | | Primary monocytes | 30 |
| PYEE (4) | | Amelanotic melanoma cells (ARN8) | 31 |
| HMGN2-N F3 (31) | F3 | Lymphatic endothelial cells (HL-60 and MDA-MB-435) | 48 |
| PFSSTKT (7) | BMHP1 | Neural stem cells | 32 |
| CTVALPGGYVRVC (13) | Pep42 | Melanomas | 33 |
| DWRVIIPPRPSA (12) | CAP | Chondrocytes | 34 |
| CDCRGDCFC (9) | RGD-4C | Angiogenic blood vasculature | 35 |
| CRGDK/RGPD/EC (11) | iRGD | Various tumors | 36 |
| cRGDf(NMeV) (5) | cRGD | Angiogenic blood vessels | 49 |
| NGR (3) | NGR | Angiogenic blood vessels | 55 |

D. Purification of Proteins

It may be desirable to purify UIM peptides, peptide-mimics or analogs thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present disclosure concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur. Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present disclosure is discussed below.

E. Peptide Synthesis

UIM-containing peptides may be generated synthetically for use in various embodiments of the present disclosure. Because of their relatively small size, the peptides of the disclosure can be synthesized in solution or on a solid support in accordance with conventional techniques. Various automatic synthesizers are commercially available and can be used in accordance with known protocols. See, for example, Stewart & Young, 1984; Tam et al., 1983; Merrifield, 1986; Barany & Merrifield, 1979, each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the disclosure is inserted into an expression vector, transformed or transfected into an appropriate host cell and cultivated under conditions suitable for expression.

2. THERAPIES

A. Cancer

The present disclosure envisions the use of the claimed UIM-containing peptides for the treatment of cancer and other diseases characterized by pathologic neovascularization. In particular, as explained herein, these peptides interfere with the normal interactions between epsins and VEGF and VEGFR-2, thereby disturbing the angiogenic processes driven by tumor formation. As a result, aberrant and non-functional vessels are produced that serve to impair blood flow to, e.g., a growing tumor and thus inhibit both its growth and spread.

Thus, in one aspect, the present disclosure seeks to treat cancers. The types of cancers are not limited except that they should have a vascular component, and thus would include any solid tumor such as brain cancer, head & neck cancer, throat cancer, nasopharyngeal cancer, esophageal cancer, lung cancer, stomach cancer, liver cancer, pancreatic cancer, colon cancer, rectal cancer, prostate cancer, testicular cancer, ovarian cancer, uterine cancer, cervical cancer, breast cancer, or skin cancer.

In addition to cancer, the present application also provides methods of treating non-cancer disease states that involve abnormal vascular development. In particular, abnormal vascular development is a contributing factor in certain diseases of the retina. Other diseases of vascular malformation include hereditary haemorrhagic telangiectasia (HHT), neurofibromatosis type 1, familial cavernous malformation, and forms of lymphangiogenesis.

B. Atherosclerosis and Heart Disease

Heart disease and its manifestations, including coronary artery disease, myocardial infarction, congestive heart failure and cardiac hypertrophy, clearly presents a major health risk in the United States today. The cost to diagnose, treat and support patients suffering from these diseases is well into the billions of dollars. The causes and effects of cardiac hypertrophy have been extensively documented, but the underlying molecular mechanisms have not been fully elucidated. What is known, however, is that atherosclerosis plays a major role in this pathologic process.

Treatment with pharmacological agents still represents the primary mechanism for reducing or eliminating the manifestations of heart failure. Diuretics constitute the first line of treatment for mild-to-moderate heart failure. Unfortunately, many of the commonly used diuretics (e.g., the thiazides) have numerous adverse effects. For example, certain diuretics may increase serum cholesterol and triglycerides. Moreover, diuretics are generally ineffective for patients suffering from severe heart failure. If diuretics are ineffective, vasodilatory agents may be used. The angiotensin converting (ACE) inhibitors (e.g., enalopril and lisinopril) not only provide symptomatic relief, they also have been reported to decrease mortality. Again, however, the ACE inhibitors are associated with adverse effects that result in their being contraindicated in patients with certain disease states (e.g., renal artery stenosis). Similarly, inotropic agent therapy (i.e., a drug that improves cardiac output by increasing the force of myocardial muscle contraction) is associated with a panoply of adverse reactions, including gastrointestinal problems and central nervous system dysfunction.

Thus, the present application addresses therapies for atherosclerosis and heart disease. By treatment, the methods include reducing one or more of the symptoms of heart failure, atherosclerosis, primary pulmonary hypertension, or cardiac hypertrophy. These symptoms include reduced exercise capacity, reduced blood ejection volume, increased left ventricular end diastolic pressure, increased pulmonary capillary wedge pressure, reduced cardiac output, cardiac index, increased pulmonary artery pressures, increased left ventricular end systolic and diastolic dimensions, and increased left ventricular wall stress, wall tension and wall thickness, elevated right ventricular systolic pressure, and elevated pulmonary arterial systolic pressures. Other aspects of treatment include improve quality of life, reduced disease-related morbidity and mortality, and reduction of confusion, fatigue, chest pain, dyspnea, and/or irregular heartbeat.

C. Obesity

Another aspect of the present disclosure concerns new methods for the treatment and prevention of obesity. Obesity has become a worldwide pandemic in recent years due to a global trend toward increased energy-dense food intake and decreased physical activity. Excessive accumulation of adipose tissue plays a central role in obesity and obesity-related complications such as cardiovascular diseases, insulin resistance and Type 2 Diabetes Mellitus (T2DM). A comprehensive understanding of the molecular mechanisms underlying adipocyte differentiation, proliferation and growth are of both fundamental and clinical relevance.

Although it is well established that weight loss can be achieved through reduced caloric intake and increased physical activity, obesity has continued to be an intractable problem in Western countries, especially in the United States. The discovery of safe and effective drugs to induce weight loss has been a major research goal for decades. However, to date the drugs that have shown efficacy have been burdened with significant side effects or have shown only modest efficacy. For example, amphetamines have been used effectively as appetite suppressants but have a strong risk of dependence along with other side effects. The discovery of leptin, a peptide hormone that plays a major role in appetite regulation, was considered to be a potential breakthrough in the treatment of obesity, but in clinical trials, leptin was not effective. More recently, cannabinoid receptor antagonists were under development as anti-obesity drugs but showed unacceptable psychiatric side effects. Similarly, drugs designed to reduce fat absorption in the digestive tract have been associated with significant gastrointestinal side effects.

Obesity is a medical condition generally defined as where a subject exhibits excess body fat accumulated to the extent that it may have an adverse effect on health. It is typically defined by body mass index (BMI) and may be further evaluated in terms of fat distribution via the waist-hip ratio and total cardiovascular risk factors. BMI is related to both percentage body fat and total body fat. BMI is calculated by dividing the subject's mass by the square of his or her height (in metric units: kilograms/meters$^2$). The definitions established by the World Health Organization (WHO) in 1997 and published in 2000 are listed below:

| BMI | Classification |
|---|---|
| <18.5 | underweight |
| 18.5-24.9 | normal weight |
| 25.0-29.9 | overweight |
| 30.0-34.9 | class I obesity |
| 35.0-39.9 | class II obesity |
| ≥40.0 | class III obesity |

Obesity increases the risk of many physical and mental conditions. These comorbidities are most commonly shown in metabolic syndrome, a combination of medical disorders which includes: T2DM, high blood pressure, high blood cholesterol, and high triglyceride levels.

A substantial body of research supports an association between obesity and a chronic, "smoldering" inflammatory state. Obesity is associated with overproduction of inflammatory cytokines and chronic activation of inflammatory signaling pathways, including the NF-kB pathway. Chronic inflammation in adipose tissue is linked with the development of insulin resistance in skeletal muscle. Chronic activation of the NF-κB pathway has been shown to induce insulin resistance and NF-κB inhibition has been proposed as a therapeutic strategy for the treatment of T2DM.

D. Formulations

The present disclosure discloses peptides numerous compositions, which in certain aspects of the disclosure, are administered to animals. For example, UIM peptides will be formulated for administration. Where clinical applications are contemplated, it will be necessary to prepare pharmaceutical compositions of these compounds and compositions in a form appropriate for the intended application. Generally, this will entail preparing compositions that are essentially free of pyrogens, as well as other impurities that could be harmful to humans or animals.

One will generally desire to employ appropriate salts and buffers to render agents suitable for introduction into a patient. Aqueous compositions of the present disclosure comprise an effective amount of the agent, dissolved or dispersed in a pharmaceutically acceptable carrier or aqueous medium. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present disclosure, its use in therapeutic compositions is contemplated. Supplementary active ingredients, such as other anti-cancer agents, can also be incorporated into the compositions.

The active compounds may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Solutions of the active ingredients as free base or pharmacologically acceptable salts can be prepared in water suitably mixed with surfactant, such as hydroxypropylcellulose. Dispersions also can be prepared in glycerol, liquid polyethylene glycols, mixtures thereof and in oils. Under ordinary conditions of storage and use, these preparations contain a preservative to prevent growth of microorganisms. Intravenous vehicles include fluid and nutrient replenishers. Preservatives include antimicrobial agents, anti-oxidants, chelating agents and inert gases. The pH and exact concentration of the various components in the pharmaceutical are adjusted according to well-known parameters.

An effective amount of the agents is determined based on the intended goal. The term "unit dose" refers to a physically discrete unit suitable for use in a subject, each unit containing a predetermined quantity of the therapeutic composition calculated to produce the desired response in association with its administration, i.e., the appropriate route and treatment regimen. The quantity to be administered, both according to number of treatments and unit dose, depends on the subject to be treated, the state of the subject, and the protection desired. Precise amounts of the therapeutic composition also depend on the judgment of the practitioner and are peculiar to each individual.

All of these forms are generally selected to be sterile and stable under the conditions of manufacture and storage.

E. Routes of Administration

The active compounds of the present disclosure can advantageously be formulated for enteral administration, e.g., formulated for oral administration. The pharmaceutical forms may include sesame oil, peanut oil or aqueous propylene glycol; and sterile powders for the extemporaneous preparation of ingestible compositions, including tablets, pills and capsules. Also, it is contemplated that the agents of the present disclosure can be provided in the form of a food additive and incorporated into a daily dietary program.

In addition to the compounds formulated for enteral administration, parenteral formulations such as intravenous or intramuscular injection are envisioned. Administration may also be nasal, buccal, rectal, vaginal or topical. Alternatively, administration may be by intratumoral, intradermal, subcutaneous, or intraperitoneal injection. Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the particular methods of preparation are vacuum-drying and freeze-drying techniques which yield a powder of the active ingredient plus any additional desired ingredient from a previously sterile-filtered solution thereof.

F. Combination Treatments—Cancer

In one embodiment, the UIM-containing peptides may be used in conjunction with another cancer therapy, such as radiation, chemotherapy, immunotherapy, hormone therapy, toxin therapy or surgery. These compositions would be provided in a combined amount effective to kill or inhibit proliferation of the cell. This process may involve contacting the cells with the agents at the same time. This may be achieved by contacting the cell with a single composition or pharmacological formulation that includes both agents, or by contacting the cell with two distinct compositions or formulations, at the same time, wherein one composition includes UIM peptide and the other includes the second agent.

Alternatively, the UIM peptide therapy may precede or follow the other agent treatment by intervals ranging from minutes to weeks. In embodiments where the other agent and UIM peptides are applied separately to the cell, tissue or organism, one would generally ensure that a significant period of time did not expire between the time of each delivery, such that the agents would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

Multiple administrations of each agent are contemplated. For example, where the UIM peptide therapy is "A" and the secondary agent or therapy is "B," the following are contemplated:

| | | | | | |
|---|---|---|---|---|---|
| A/B/A | B/A/B | B/B/A | A/A/B | A/B/B | B/A/A |
| A/B/B/B | B/A/B/B | B/B/B/A | B/B/A/B | A/A/B/B | A/B/A/B |
| A/B/B/A | B/B/A/A | B/A/B/A | B/A/A/B | A/A/A/B | B/A/A/A |
| A/B/A/A | A/A/B/A | | | | |

Patients will be evaluated for neurological changes considered to be independent of tumor and graded using NCI Common Toxicity Criteria (neurotoxicity). Aside from baseline audiometric testing, repeat audiometric testing for ototoxicity is performed at the physician's discretion for patients who had evidence of hearing loss or progression of hearing loss by neurological examination. In addition, blood counts should be performed biweekly, and serum creatinine, alkaline phosphatase, bilirubin and alanine amino-transferase tested before each cycle. Doses may be modified during the course of treatment, primarily based on neutrophil and platelet counts or ototoxicity.

Chemotherapy.

A variety of chemical compounds, also described as "chemotherapeutic" or "genotoxic agents," are intended to be of use in the combined treatment methods disclosed herein. In treating cancer according to the disclosure, one would contact the tumor cells with an agent in addition to the expression construct. Various classes of chemotherapeutic agents are contemplated for use with in combination with peptides of the present disclosure. For example, selective estrogen receptor antagonists ("SERMs"), such as Tamoxifen, 4-hydroxy Tamoxifen (Afimoxfene), Falsodex, Raloxifene, Bazedoxifene, Clomifene, Femarelle, Lasofoxifene, Ormeloxifene, and Toremifene.

Chemotherapeutic agents contemplated to be of use, include, e.g., camptothecin, actinomycin-D, and mitomycin C. The disclosure also encompasses the use of a combination of one or more DNA damaging agents, whether radiation-based or actual compounds, such as the use of X-rays with cisplatin or the use of cisplatin with etoposide. The agent may be prepared and used as a combined therapeutic composition, or kit, by combining it with a UIM peptide, as described above.

Heat shock protein 90 is a regulatory protein found in many eukaryotic cells. HSP90 inhibitors have been shown to be useful in the treatment of cancer. Such inhibitors include Geldanamycin, 17-(Allylamino)-17-demethoxygeldanamycin, PU-H71 and Rifabutin.

Agents that directly cross-link DNA or form adducts are also envisaged. Agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include Adriamycin, also known as Doxorubicin, Etoposide, Verapamil, Podophyllotoxin, and the like. Widely used in a clinical setting for the treatment of neoplasms, these compounds are administered through bolus injections intravenously at doses ranging from 25-75 mg/m$^2$ at 21 day intervals for Doxorubicin, to 35-50 mg/m$^2$ for etoposide intravenously or double the intravenous dose orally. Microtubule inhibitors, such as taxanes, also are contemplated. These molecules are diterpenes produced by the plants of the genus *Taxus*, and include paclitaxel and docetaxel.

Epidermal growth factor receptor inhibitors, such as Iressa, mTOR, the mammalian target of rapamycin, also known as FK506-binding protein 12-rapamycin associated protein 1 (FRAP1) is a serine/threonine protein kinase that regulates cell growth, cell proliferation, cell motility, cell survival, protein synthesis, and transcription. Rapamycin and analogs thereof ("rapalogs") are therefore contemplated for use in combination cancer therapy in accordance with the present disclosure.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Radiation.

Factors that cause DNA damage and have been used extensively for cancer therapy and include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells. The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

Surgery.

Approximately 60% of persons with cancer will undergo surgery of some type, which includes preventative, diagnostic or staging, curative and palliative surgery. Curative surgery as a cancer treatment may be used in conjunction with other therapies, such as the treatment of the present disclosure, chemotherapy, radiotherapy, hormonal therapy, gene therapy, immunotherapy and/or alternative therapies. Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present disclosure may be used in conjunction with removal of superficial cancers, precancers, or incidental amounts of normal tissue.

Cytokine Therapy.

Another possible combination therapy with the peptides claimed herein is TNF-α (tumor necrosis factor-alpha), a cytokine involved in systemic inflammation and a member of a group of cytokines that stimulate the acute phase reaction. The primary role of TNF is in the regulation of immune cells. TNF is also able to induce apoptotic cell death, to induce inflammation, and to inhibit tumorigenesis and viral replication.

Immunotherapy.

Immunotherapy is generally defined as fostering an immune response against a tumor cell or cancer. This can take many forms, and may overlap with cytokine therapy to the extent that administered cytokines help stimulate the immune system. However, one particular immunotherapy involves the provision on anti-cancer antibodies. Where the antibodies themselves are therapeutic, this can be considered a passive immunotherapy. Examples of therapeutic antibodies include Herceptin® and Erbitux®.

Hormone Therapy.

Hormone therapies are most commonly employed where a cancer has some hormonal aspect, such as breast and ovarian cancers. Unlike hormone replacement, cancer hormone therapy seeks to block the positive effect of some hormones on cancer cells, and thus are actually hormone antagonists (e.g., anti-estrogens).

Toxin Therapy.

Toxins may be used to selectively kill any disease causing cell, including a tumor cell. A variety of toxins have been used for this purpose, including cholera toxin, ricin and pertussin toxin. The difficulty with use of toxins in in vivo applications is their non-selectivity, and toxicity to non-target cells. As such, schemes for selective delivery are envisioned, most commonly using tumor-homing peptides and antibodies that bind to structures not present on normal cells but found on cancer cells, or structures that are over-expressed on cancer cells as compared to normal cells.

Phenyl N-Tert-Butyl Nitrones (PBNs).

The compound phenyl N-tert-butyl nitrone (PBN) was first synthesized in the 1950's, but in 1968 it was discovered to be very useful to trap and stabilize free radicals in chemical reactions and hence it was termed a spin-trap (Janzen, 1971). Although PBN is the prototype spin-trap, several other nitrones have been synthesized and found useful to trap and characterize free radicals in chemical reactions. These spin traps were used in chemical reactions first, but in the mid-1970's they began to be used to trap free radicals in biochemical and biological systems (Floyd et al., 1977; Poyer et al., 1978). Pharmacokinetic studies have shown that PBN is readily and rapidly distributed almost equally to all tissues, has a half-life in rats of about 132 minutes and is eliminated mostly in the urine. Relatively few metabolism studies have been done, but it is known that some ring hydroxylation (primarily in the para position) of the compound occurs in the liver.

Novelli first showed that PBN could be used to protect experimental animals from septic shock (Novelli et al., 1986), and indeed this was later confirmed by other groups (Pogrebniak et al., 1992). The use of PBN and derivations as pharmacological agents began after discoveries in 1988 that showed that PBN had neuroprotective activity in experimental brain stroke models (Floyd, 1990; Floyd et al., 1996; Carney et al., 1991). These results were repeated and extended, (see Clough-Helfman et al., 1991; Cao et al., 1994; Folbergrova et al., 1995; Pahlmark et al., 1996). Others inventors have summarized the extensive neuroprotective pharmacological research effort on PBN and derivatives (Floyd, 1997; Hensley et al., 1996). In addition to neurodegenerative diseases, PBN has been shown to protect in other pathological conditions where ROS-mediated processes are involved, including diabetes and many other conditions. The mechanistic basis of why PBN and some of its derivatives are so neuroprotective in experimental stroke and several other neurodegenerative models has not been completely elucidated yet. However, it is clear that its action cannot simply be explained by its ability to trap free radicals.

The general formula for PBNs is:

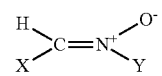

wherein X is phenyl or

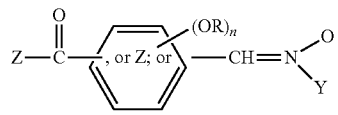

R is H,
and n is a whole integer from 1 to 5; or

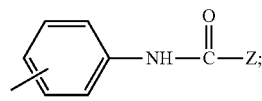

Y is a tert-butyl group that can be hydroxylated or acetylated on one or more positions;
phenyl; or

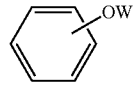

wherein W is

or Z; and Z is a $C_1$ to $C_5$ straight or branched alkyl group.

U.S. Pat. No. 5,569,902 (incorporated herein by reference) describes the use of nitrone free radical trapping agents for the treatment of cancer. Specifically, PBN and related compounds are described as being useful in the preparation of an anti-carcinogenic diet and the preparation of such supplemented diets. Those subjects most likely to beneficially receive the nitrones would include: (1) those having had pretumor tests indicating a high probability of the presence of tumors, (2) those exposed to very potent carcinogenic environments and their probability of tumor progression is high, and (3) to those whose genetic predisposition makes their likelihood of tumor development high.

U.S. Patent Publication 2007/0032453 (incorporated herein by reference) describes the effect of the anti-inflammatory phenyl N-tert-butyl nitrones (PBNs) on gliomas using MRI techniques. PBN itself was able to control tumor development when provided to a subject either before, at the time of or after tumor implantation. Thus, it was proposed to use PBN, and related nitrone free radical trapping agents, as therapeutic agents for gliomas.

U.S. Pat. No. 5,488,145 (incorporated herein by reference) describes 2,4-disulfonyl phenyl-tert-butyl nitrone and its pharmaceutically acceptable salts. These materials were described as useful pharmaceutical agents for oral or intravenous administration to patients suffering from acute central nervous system oxidation as occurs in a stroke or from gradual central nervous system oxidation which can exhibit itself as progressive central nervous system function loss.

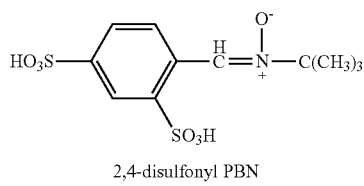

2,4-disulfonyl PBN 2,4-disulfonyl PBN's two sulfonate groups was expected to exhibit improved water solubility, but was also expected to exhibit poor transport across the blood/brain barrier because of its lipophobic character. However, when the present compound was made and tested in vivo, it showed an unexpected increase in efficacy as compared to PBN. This increase in efficacy occurred along with an increase in potency as compared to PBN. In direct contrast to this marked increase in potency and efficacy there was a marked and highly significant decrease in toxicity as compared to PBN.

These results were unexpected because in the general literature on structure/activity relationships within specific defined families of compounds therapeutic potency typically covaries with toxicity. Thus, most related compounds maintain their ratio of therapeutic potency to toxicity. In contrast, the compound of this disclosure deviates from this expected relationship when its potency increased and its toxicity decreased relative to closely related analogs.

Accordingly, in one aspect, the disclosure provides the PBN-disulfonyl compound and its pharmaceutically acceptable salts. In a second aspect, the disclosure provides intravenously- and orally-administrable pharmaceutical compositions having this compound or its salt as active ingredient.

2,4-ds PBN may exists at higher pHs in an ionized salt form:

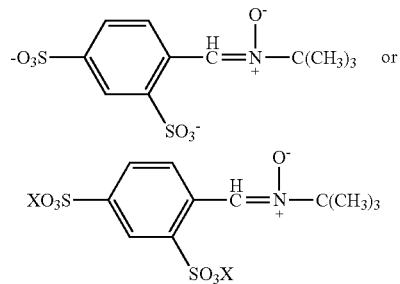

where X is a pharmaceutically acceptable cation. Most commonly, this cation is a monovalent material such as sodium, potassium or ammonium, but it can also be a multivalent alone or cation in combination with a pharmaceutically acceptable monovalent anion, for example calcium with a chloride, bromide, iodide, hydroxyl, nitrate, sulfonate, acetate, tartrate, oxalate, succinate, palmoate or the like anion; magnesium with such anions; zinc with such anions or the like. When these combinations of a polyvalent cation and a monovalent anion are illustrated in structural formulae, herein, the monovalent anion is identified as "Y."

Among these materials, the free acid and the simple sodium, potassium or ammonium salts are most preferred with the calcium and magnesium salts also being preferred but somewhat less so.

2,4-ds PBN can be prepared by a two-step reaction sequence. In the first step, commercially available tertiary butyl nitrate (2-methyl-2-nitropropane) is converted to the corresponding n-hydroxyl amine using a suitable catalyst such as an activated zinc/acetic acid catalyst or an aluminum/mercury amalgam catalyst. This reaction can be carried out in 0.5 to 12 hours and especially about 2 to 6 hours or so at a temperature of about 15-100° C. in a liquid reaction medium such as alcohol/water mixture in the case of the zinc catalyst or an ether/water mixture in the case of the aluminum amalgam catalyst.

In the second step, the freshly formed hydroxylamine is reacted with 4-formyl-1,3-benzenedisulfonic acid, typically with a slight excess of the amine being used. This reaction can be carried out at similar temperature conditions. This reaction is generally complete in 10 to 24 hours.

The product so formed is the free acid and is characterized by a molecular weight of 89 g/mole. It is a white powdery material which decomposes upon heating. It is characterized by a solubility in water of greater than 1 gram/ml and a $^1$H NMR spectrum in $D_2O$ of 8.048 ppm (dd, 8.4, 1.7 Hz); 8.836 ppm (d, 8.4 Hz); 8.839 ppm (d, 1.7 Hz); 8.774 ppm (s). The various salts can be easily formed by admixing the free acid in aqueous medium with two equivalents of the appropriate base, for example, KOH for the potassium salt, and the like.

F. Combination Therapy—Atherosclerosis and Hearts Disease

In one embodiment, the UIM-containing peptides may be used in conjunction with another therapy, in particular one that focuses on reduction of lipids and atherogenic substances and actions. These compositions would be provided in a combined amount effective to prevent, inhibit or reduce atherosclerosis. This process may involve administering to subject both agents/therapies at the same time. This may be achieved by administering a single composition or pharmacological formulation that includes both agents, or by administering two distinct compositions or formulations, at the same time, wherein one composition includes UIM peptide and the other includes the second agent.

Alternatively, the UIM peptide therapy may precede or follow the other agent treatment by intervals ranging from minutes to weeks. In embodiments where the other agent and UIM peptides are applied separately to the subject, one would generally ensure that a significant period of time did not expire between each delivery, such that the agents would still be able to exert an advantageously combined effect. In such instances, it is contemplated that one may administer both modalities within about 12-24 hr of each other and, more preferably, within about 6-12 hr of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

Multiple administrations of each agent are contemplated. For example, where the UIM peptide therapy is "A" and the secondary agent or therapy is "B," the following are contemplated:

| | | | | | |
|---|---|---|---|---|---|
| A/B/A | B/A/B | B/B/A | A/A/B | A/B/B | B/A/A |
| A/B/B/B | B/A/B/B | B/B/B/A | B/B/A/B | A/A/B/B | A/B/A/B |
| A/B/B/A | B/B/A/A | B/A/B/A | B/A/A/B | A/A/A/B | B/A/A/A |
| A/B/A/A | A/A/B/A | | | | |

Below are some exemplary but non-limiting examples of therapies that could be used in conjunction with the UIM peptides of the present disclosure.

1. Antihyperlipoproteinemics

In certain embodiments, administration of an agent that lowers the concentration of one of more blood lipids and/or lipoproteins, known herein as an "antihyperlipoproteinemic," may be combined with a cardiovascular therapy according to the present invention, particularly in treatment of atherosclerosis and thickenings or blockages of vascular tissues. In certain aspects, an antihyperlipoproteinemic agent may comprise an aryloxyalkanoic/fibric acid derivative, a resin/bile acid sequesterant, a HMG CoA reductase inhibitor, a nicotinic acid derivative, a thyroid hormone or thyroid hormone analog, a miscellaneous agent or a combination thereof.

a. Aryloxyalkanoic Acid/Fibric Acid Derivatives

Non-limiting examples of aryloxyalkanoic/fibric acid derivatives include beclobrate, enzafibrate, binifibrate, ciprofibrate, clinofibrate, clofibrate (atromide-S), clofibric acid, etofibrate, fenofibrate, gemfibrozil (lobid), nicofibrate, pirifibrate, ronifibrate, simfibrate and theofibrate.

b. Resins/Bile Acid Sequesterants

Non-limiting examples of resins/bile acid sequesterants include cholestyramine (cholybar, questran), colestipol (colestid) and polidexide.

c. HMG CoA Reductase Inhibitors

Non-limiting examples of HMG CoA reductase inhibitors include lovastatin (mevacor), pravastatin (pravochol) or simvastatin (zocor).

d. Nicotinic Acid Derivatives

Non-limiting examples of nicotinic acid derivatives include nicotinate, acepimox, niceritrol, nicoclonate, nicomol and oxiniacic acid.

e. Thryroid Hormones and Analogs

Non-limiting examples of thyroid hormones and analogs thereof include etoroxate, thyropropic acid and thyroxine.

f. Miscellaneous Antihyperlipoproteinemics

Non-limiting examples of miscellaneous antihyperlipoproteinemics include acifran, azacosterol, benfluorex, b-benzalbutyramide, camitine, chondroitin sulfate, clomestrone, detaxtran, dextran sulfate sodium, 5,8,11,14,17-eicosapentaenoic acid, eritadenine, farazabol, meglutol, melinamide, mytatrienediol, omithine, g-oryzanol, pantethine, pentaerythritol tetraacetate, a-phenylbutyramide, pirozadil, probucol (lorelco), b-sitosterol, sultosilic acid-piperazine salt, tiadenol, triparanol and xenbucin.

2. Antiarteriosclerotics

Non-limiting examples of an antiarteriosclerotic include pyridinol carbamate.

3. Antithrombotic/Fibrinolytic Agents

In certain embodiments, administration of an agent that aids in the removal or prevention of blood clots may be combined with administration of a modulator, particularly in treatment of atherosclerosis and vasculature (e.g., arterial) blockages. Non-limiting examples of antithrombotic and/or fibrinolytic agents include anticoagulants, anticoagulant antagonists, antiplatelet agents, thrombolytic agents, thrombolytic agent antagonists or combinations thereof.

In certain aspects, antithrombotic agents that can be administered orally, such as, for example, aspirin and wafarin (coumadin) are preferred.

a. Anticoagulants

A non-limiting example of an anticoagulant include acenocoumarol, ancrod, anisindione, bromindione, clorindione, coumetarol, cyclocumarol, dextran sulfate sodium, dicumarol, diphenadione, ethyl biscoumacetate, ethylidene dicoumarol, fluindione, heparin, hirudin, lyapolate sodium, oxazidione, pentosan polysulfate, phenindione, phenprocoumon, phosvitin, picotamide, tioclomarol and warfarin.

b. Antiplatelet Agents

Non-limiting examples of antiplatelet agents include aspirin, a dextran, dipyridamole (persantin), heparin, sulfinpyranone (anturane) and ticlopidine (ticlid).

c. Thrombolytic Agents

Non-limiting examples of thrombolytic agents include tissue plasminogen activator (activase), plasmin, pro-urokinase, urokinase (abbokinase) streptokinase (streptase), anistreplase/APSAC (eminase).

3. Antihypertensive Agents

Non-limiting examples of antihypertensive agents include sympatholytic, alpha/beta blockers, alpha blockers, anti-angiotensin II agents, beta blockers, calcium channel blockers, vasodilators and miscellaneous antihypertensives.

a. Alpha Blockers

Non-limiting examples of an alpha blocker, also known as an a-adrenergic blocker or an a-adrenergic antagonist, include amosulalol, arotinolol, dapiprazole, doxazosin, ergoloid mesylates, fenspiride, indoramin, labetalol, nicergoline, prazosin, terazosin, tolazoline, trimazosin and yohimbine. In certain embodiments, an alpha blocker may comprise a quinazoline derivative. Non-limiting examples of quinazoline derivatives include alfuzosin, bunazosin, doxazosin, prazosin, terazosin and trimazosin.

b. Alpha/Beta Blockers

In certain embodiments, an antihypertensive agent is both an alpha and beta adrenergic antagonist. Non-limiting examples of an alpha/beta blocker comprise labetalol (normodyne, trandate).

c. Anti-Angiotension II Agents

Non-limiting examples of anti-angiotension II agents include angiotensin converting enzyme inhibitors and angiotension II receptor antagonists. Non-limiting examples of angiotension converting enzyme inhibitors (ACE inhibitors) include alacepril, enalapril (vasotec), captopril, cilazapril, delapril, enalaprilat, fosinopril, lisinopril, moveltopril, perindopril, quinapril and ramipril. Non-limiting examples of an angiotensin II receptor blocker, also known as an angiotension II receptor antagonist, an ANG receptor blocker or an ANG-IL type-1 receptor blocker (ARBS), include angiocandesartan, eprosartan, irbesartan, losartan and valsartan.

d. Sympatholytics

Non-limiting examples of a sympatholytic include a centrally acting sympatholytic or a peripherially acting sympatholytic. Non-limiting examples of a centrally acting sympatholytic, also known as an central nervous system (CNS) sympatholytic, include clonidine (catapres), guanabenz (wytensin) guanfacine (tenex) and methyldopa (aldomet). Non-limiting examples of a peripherally acting sympatholytic include a ganglion blocking agent, an adrenergic neuron blocking agent, a β-adrenergic blocking agent or a α1-adrenergic blocking agent. Non-limiting examples of a ganglion blocking agent include mecamylamine (inversine) and trimethaphan (arfonad). Non-limiting of an adrenergic neuron blocking agent include guanethidine (ismelin) and reserpine (serpasil). Non-limiting examples of a β-adrenergic blocker include acenitolol (sectral), atenolol (tenormin), betaxolol (kerlone), carteolol (cartrol), labetalol (normodyne, trandate), metoprolol (lopressor), nadanol (corgard), penbutolol (levatol), pindolol (visken), propranolol (inderal) and timolol (blocadren). Non-limiting examples of α-1-adrenergic blocker include prazosin (minipress), doxazocin (cardura) and terazosin (hytrin).

e. Vasodilators

In certain embodiments a cardiovascular therapeutic agent may comprise a vasodilator (e.g., a cerebral vasodilator, a coronary vasodilator or a peripheral vasodilator). In certain preferred embodiments, a vasodilator comprises a coronary vasodilator. Non-limiting examples of a coronary vasodilator include amotriphene, bendazol, benfurodil hemisuccinate, benziodarone, chloracizine, chromonar, clobenfurol, clonitrate, dilazep, dipyridamole, droprenilamine, efloxate, erythrityl tetranitrane, etafenone, fendiline, floredil, ganglefene, herestrol bis(b-diethylaminoethyl ether), hexobendine, itramin tosylate, khellin, lidoflanine, mannitol hexanitrane, medibazine, nicorglycerin, pentaerythritol tetranitrate, pentrinitrol, perhexiline, pimethylline, trapidil, tricromyl, trimetazidine, trolnitrate phosphate and visnadine.

In certain aspects, a vasodilator may comprise a chronic therapy vasodilator or a hypertensive emergency vasodilator. Non-limiting examples of a chronic therapy vasodilator include hydralazine (apresoline) and minoxidil (loniten). Non-limiting examples of a hypertensive emergency vasodilator include nitroprusside (nipride), diazoxide (hyperstat IV), hydralazine (apresoline), minoxidil (loniten) and verapamil.

f. Miscellaneous Antihypertensives

Non-limiting examples of miscellaneous antihypertensives include ajmaline, g aminobutyric acid, bufeniode, cicletainine, ciclosidomine, a cryptenamine tannate, fenoldopam, flosequinan, ketanserin, mebutamate, mecamylamine, methyldopa, methyl 4-pyridyl ketone thiosemicarbazone, muzolimine, pargyline, pempidine, pinacidil, piperoxan, primaperone, a protoveratrine, raubasine, rescimetol, rilmenidene, saralasin, sodium nitrorusside, ticrynafen, trimethaphan camsylate, tyrosinase and urapidil.

In certain aspects, an antihypertensive may comprise an arylethanolamine derivative, a benzothiadiazine derivative, a N-carboxyalkyl(peptide/lactam) derivative, a dihydropyridine derivative, a guanidine derivative, a hydrazines/phthalazine, an imidazole derivative, a quanternary ammonium compound, a reserpine derivative or a suflonamide derivative.

Arylethanolamine Derivatives. Non-limiting examples of arylethanolamine derivatives include amosulalol, bufuralol, dilevalol, labetalol, pronethalol, sotalol and sulfinalol.

Benzothiadiazine Derivatives. Non-limiting examples of benzothiadiazine derivatives include althizide, bendroflumethiazide, benzthiazide, benzylhydrochlorothiazide, buthiazide, chlorothiazide, chlorthalidone, cyclopenthiazide, cyclothiazide, diazoxide, epithiazide, ethiazide, fenquizone, hydrochlorothizide, hydroflumethiazide, methyclothiazide, meticrane, metolazone, paraflutizide, polythizide, tetrachlormethiazide and trichlormethiazide.

N-carboxyalkyl(peptide/lactam) Derivatives. Non-limiting examples of N-carboxyalkyl(peptide/lactam) derivatives include alacepril, captopril, cilazapril, delapril, enalapril, enalaprilat, fosinopril, lisinopril, moveltipril, perindopril, quinapril and ramipril.

Dihydropyridine Derivatives. Non-limiting examples of dihydropyridine derivatives include amlodipine, felodipine, isradipine, nicardipine, nifedipine, nilvadipine, nisoldipine and nitrendipine.

Guanidine Derivatives. Non-limiting examples of guanidine derivatives include bethanidine, debrisoquin, guanabenz, guanacline, guanadrel, guanazodine, guanethidine, guanfacine, guanochlor, guanoxabenz and guanoxan.

Hydrazines/Phthalazines. Non-limiting examples of hydrazines/phthalazines include budralazine, cadralazine, dihydralazine, endralazine, hydracarbazine, hydralazine, pheniprazine, pildralazine and todralazine.

Imidazole Derivatives. Non-limiting examples of imidazole derivatives include clonidine, lofexidine, phentolamine, tiamenidine and tolonidine.

Quanternary Ammonium Compounds. Non-limiting examples of quanternary ammonium compounds include azamethonium bromide, chlorisondamine chloride, hexamethonium, pentacynium bis(methylsulfate), pentamethonium bromide, pentolinium tartrate, phenactropinium chloride and trimethidinium methosulfate.

Reserpine Derivatives. Non-limiting examples of reserpine derivatives include bietaserpine, deserpidine, rescinnamine, reserpine and syrosingopine.

Sulfonamide Derivatives. Non-limiting examples of sulfonamide derivatives include ambuside, clopamide, furosemide, indapamide, quinethazone, tripaamide and xipamide.

4. Surgical Therapeutic Intervention

In certain aspects, the secondary therapy may comprise a surgery of some type, which includes, for example, preventative, diagnostic or staging, curative and palliative surgery. Surgery, and in particular a curative surgery, may be used in conjunction with other therapies, such as the present invention and one or more other agents.

Such surgical therapies for vascular and cardiovascular diseases and disorders are well known to those of skill in the art, and may comprise, but are not limited to, performing surgery on an organism, providing a cardiovascular mechanical prostheses, angioplasty, coronary artery reperfusion, catheter ablation, providing an implantable cardioverter defibrillator to the subject, mechanical circulatory support or a combination thereof. Non-limiting examples of a mechanical circulatory support that may be used in the present invention comprise an intra-aortic balloon counterpulsation, left ventricular assist device or combination thereof.

G. Combination Therapy—Obesity

In one embodiment, the UIM-containing peptides may be used in conjunction with another therapy, in particular one that focuses on reduction of weight or prevention of weight gain. These compositions would be provided in a combined amount effective to prevent, inhibit or reduce obesity. This process may involve administering to subject both agents/ therapies at the same time. This may be achieved by administering a single composition or pharmacological formulation that includes both agents, or by administering two distinct compositions or formulations, at the same time, wherein one composition includes UIM peptide and the other includes the second agent.

Alternatively, the UIM peptide therapy may precede or follow the other agent treatment by intervals ranging from minutes to weeks. In embodiments where the other agent and UIM peptides are applied separately to the subject, one would generally ensure that a significant period of time did not expire between each delivery, such that the agents would still be able to exert an advantageously combined effect. In such instances, it is contemplated that one may administer both modalities within about 12-24 hr of each other and, more preferably, within about 6-12 hr of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

Multiple administrations of each agent are contemplated. For example, where the UIM peptide therapy is "A" and the secondary agent or therapy is "B," the following are contemplated:

| A/B/A | B/A/B | B/B/A | A/A/B | A/B/B | B/A/A |
|---|---|---|---|---|---|
| A/B/B/B | B/A/B/B | B/B/B/A | B/B/A/B | A/A/B/B | A/B/A/B |
| A/B/B/A | B/B/A/A | B/A/B/A | B/A/A/B | A/A/A/B | B/A/A/A |
| A/B/A/A | A/A/B/A | | | | |

Some exemplary but non-limiting examples of therapies that could be used in conjunction with the UIM peptides of the present disclosure include naltrexone (Bupropion), Phentermine (Adipex-P, Suprenza), Phentermine-topiramate (Qsymia), Lorcaserin (Belviq), and Orlistat (Xenical).

3. EXAMPLES

The following examples are included to demonstrate particular embodiments of the disclosure. It should be appreciated by those of skill in the art that the techniques disclosed in the examples which follow represent techniques discovered by the inventor to function well in the practice of the disclosure, and thus can be considered to constitute specifically contemplated modes for its practice. However, those of skill in the art should, in light of the present disclosure, appreciate that many changes can be made in the specific embodiments which are disclosed and still obtain a like or similar result without departing from the spirit and scope of the disclosure.

Example 1—Cancer

A. Materials and Methods
Antibodies, Reagents and Chemicals.

Polyclonal rabbit antibodies for epsins 1 and 2 were obtained as previously described (Pasula et al., 2012 and Rosenthal et al., 1999). Epsin 1 antibody (goat) was purchased from Santa Cruz Biotechnology. Anti-phospho-VEGFR2 (pY11175), anti-PLCγ, anti-ERK, anti-phospho-ERK, anti-AKT, anti-phospho-AKT, anti-PDGFR-β and anti-Snail antibodies were purchased from Cell Signaling Technology. Anti-phospho-VEGFR2 (pY1054/1059) antibody was purchased from Millipore. Anti-FGFR1 antibody was purchased from Abcam. Anti-EGFR antibody was purchased from Rockland. Anti-vimentin antibody was purchased from Dako. VEGF-A, FGF and PDGF were purchased from R&D systems. VEGFR2 kinase inhibitor was purchased from Calbiochem. BrdU, 4-hydroxytamoxifen and human fibronectin were purchased from Sigma. Anti-CD31 antibody and matrigel (in vitro and in vivo-phenol-free) were purchased from BD Biosciences. Integrin αv and β3 plasmids were purchased from Addgene (Cambridge, Mass., USA). All other chemicals were purchased from Sigma or elsewhere. Anti-VEGF (B20-4.1.1) antibody was a kind gift from Genentech (California).

Peptide Synthesis.

All peptides were synthesized at ≥95% purity by HPLC and dissolved in ddH$_2$O (total charge "Neutral"). Peptide endotoxin (EU/mg) was monitored using LAL kit (Pierce) per manufacturer's instructions.

Animals Models.

C56BL/6 mice and TRAMP prostate cancer models were obtained from Jackson Laboratory. SCID/NOD immune-deficient mice were purchased from Charles River Labs (Wilmington, Mass.). WT-Flk, EC-iDKO, EC-iDKO-Flk and EC-iDKO-Notch mice were generated by crossing conditional double knockout mice (EC-iDKO) with Flk-1$^{fl/fl}$ or NICD$^{LSL}$ mice as described in (FIGS. 13A-D) (Pasula et al., 2012; Tessneer et al., 2014). All animal protocols have been approved by the IACUC in Oklahoma Medical Research Foundation. Animal tumor models were established as follows:

(1) Subcutaneous Tumor Models (LLC, melanoma B16 and glioma U87/SCID): LLC, melanoma and glioma tumor models were established as previously described (Pasula et al., 2012). Synthetic peptides were administered at 10 mg/kg intravenously every second day beginning after small tumors were established (20-50 mm$^3$; approximately 12 days post implantation). Tumor volumes were monitored every other day until euthanized following IACUC tumor scoring system.

(2) TRAMP Prostate Tumor Model (Transgenic Adenocarcinoma of Mouse Prostate). Mice aged 20 weeks received control or UPI peptides by intraperitoneal injection every second day (20 mg/kg) until the mice died or were euthanized following IACUC tumor scoring system. Mortality rates were recorded. Prostate tumors were analyzed by weighing genitourinary tract (GU), H&E staining, IHC, IF staining and Western blotting as previously described (Pasula et al., 2012; Tessneer et al., 2013). Lymph nodes, lung, liver, spleen and bones were similarly analyzed for metastasis.

(3) B16 Melanoma Metastasis Model. 1×10$^6$ B16 melanoma cancer cells were subcutaneously implanted into C56BL/6 mice. Established tumors (400-500 mm$^3$) were surgically removed then UPI or control peptides were intravenously injected every second day (10 mg/kg) for five weeks. Mice were sacrificed after 5 weeks and tissues (including lung, liver and lymph nodes, etc.) were harvested and analyzed for metastasis by gross morphology, H&E, IHC or IF staining, as well as Western blotting.

(4) Orthotopical Glioma Tumor Models (U87/SCID and GL261/C56BL/6). Orthotopic glioma models were established by implanting U87 or GL261 glioma cells in the forebrain of SCID or C57BL/6 mice, respectively, as previously described (Doblas et al., 2012). Tumors were monitored by MRI as previously described (Pasula et al., 2012). Once tumors reached 10-20 mm³ in size, control or UPI peptides were administered intravenously every second day (10 mg/kg). Tumor volume was analyzed by MRI every other day until the mice died or were euthanized following IACUC tumor scoring system. Mortality rates were recorded. Anti-VEGF antibody (B20-4.1.1) serves as positive control (5 mg/kg).

Toxicity Analysis of UPI Peptide in Plasma Ex Vivo.

Age and gender matched wild type mice were intravenously injected with PBS (Control) or different concentration of UPI peptide every second day for up to 3 months. Plasma biochemical parameters were evaluated by the UT-Southwestern Medical Center Core Facility in Dallas, Tex.

Pharmacokinetic Analysis of UPI Peptide in Plasma Ex Vivo.

Plasma obtained from wild type mice was incubated with 1 µg/ml biotinylated-UPI plasma at 37° C. for various time points. Residual biotinylated-UPI was measured by ELISA using Biotin Kit from MyBioSource (San Diego, Calif.). Background was determined using basal plasma (no UPI added) and subtracted during analysis.

Kinetic Analysis and FUPI Peptide Distribution In Vivo.

LLC or B16 tumor-bearing mice were intravenously injected with 20 mg/kg FUPI peptide then sacrificed at different time points. Both tumor and non-tumor tissues were collected, fixed in 4% PFA and processed for IF staining with anti-CD31 to visualize blood vessels. Images were captured with green channel (FUPI), red channel (CD31) and blue channel (DAPI) simultaneously. FITC and CD31 fluorescent intensity was quantified using Metamorph software. The number of FUPI and CD31-positive vessels were counted and presented as a percentage of FUPI-positive vessels-to-total CD31-positive vessels.

Co-Administration of Anti-VEGF Antibody or VEGFR2 Kinase Inhibitor and UPI Peptide in LLC Tumor Model.

LLC tumor-bearing mice were intravenously injected with anti-VEGF antibody (B20-4.1.1) (1.5 mg/kg), UPI (10 mg/kg) or co-injected with anti-VEGF/UPI every second day for 12 days. Similarly, VEGFR2 kinase inhibitor was injected (0.5 mg/kg) or co-injected with inhibitor/UPI. Tumor growth was monitored as described above.

In Vivo Angiogenesis Assays.

In vivo angiogenesis was analyzed using matrigel plugs and retina neovascularization as previously described (Tessneer et al., 2014; Liu et al., 2009; Valapala et al., 2011; Cai et al., 2012; Nakayama et al., 2013) with the following modifications:

(1) Matrigel Plug Angiogenesis Assay. C56BL/6 mice were subcutaneously injected with 400 µl phenol-free matrigel (BD Biosciences cat #356231) containing 500 ng/ml VEGF and 100 µg/ml UPI or control peptide. After 6 days, mice were sacrificed then the plugs were removed, fixed in 4% PFA and processed for IF staining for CD31.

(2) Retina Neovascularization. Wild-type pups were intraocularly injected with 1 µl of control or UPI peptide (1 µg/µl) at P1, P3 and P5 as previously described (Cai et al., 2012). Pups were sacrificed at P6 then retinas were whole-mount and stained with isolectin B4 antibody as previously reported (Nakayama et al., 2013).

Hypoxia Analysis in Subcutaneous U87 Glioma Tumors.

Mice bearing subcutaneous U87 tumors were intraperitoneal injected with the hypoxia probe, pimonidazole hydrochloride (50 mg/ml stock solution; Hypoxyprobe, Inc, Burlington, Mass.), at 60 mg/kg body weight for 1 hr. Mice were then sacrificed and tumors fixed in 4% PFA. Hypoxia was measured by IF staining of tumor samples. Areas of hypoxia were quantified using Image J software.

In Situ VEGFR2 Monitoring in the Orthotopic U87 Glioma Model.

Control or UPI-peptide treated U87 glioma tumor-bearing mice were anesthetized with isofluorane, set up with a tail-vein catheter, put on a cradle, and inserted in a 7.0 Tesla small animal MRI system (Bruker Biospin). VEGFR2-targeted MRI probe (anti-VEGFR2-Gd-albumin-biotin) was administered as previously described (He et al., 2013). Pre- and 90 min post-contrast MRI images were taken following administration. Intensity of VEGFR2 was quantified using Image J software.

Biochemical Pulldown Assay Using Ex Vivo Tumors.

LLC or GL261 glioma tumors was homogenized in lysis buffer containing 50 mM Tris-HCl pH7.5, 150 mM NaCl, 0.05% NP-40, 10% Glycerol, 1× cocktail, and 20 mM NEM. Protein concentration was determined by BCA kit (Pierce). 0.5-2 mg lysates were co-incubated with 100 µM biotinylated UPI or control peptides, followed by the addition of Neutri-Avidin beads (Invitrogen) for pulldown binding assay. Beads were washed twice with lysis buffer, then twice with 1:1 lysis buffer PBS. Beads were then boiled for 5 min in 2× sample loading buffer. Denatured proteins were subjected to Western blotting using anti-VEGFR2, anti-EGFR, anti-FGFR1 and anti-PDGFR-β antibodies.

Construction and Mammalian Expression of Human VEGFR2 Kinase Domain (KD).

Human VEGFR2 kinase domain (KD) (McTigue et al., 2012) was PCR-amplified from full length VEGFR2 template and cloned into TA cloning vector, pGEM-Teasy (Promega). Cloning was confirmed by sequencing (OMRF Core Facility). Resulting VEGFR2 KD with a 6×His tag at the C-terminus was then inserted into mammalian expression vector, pcDNA3, by EcoRV/NotI sites. Resulting plasmid was transfected into 293T cells using Lipofectamine 2000. Twenty-four hours post-transfection, expression of His-tagged VEGFR2 KD was confirmed by Western blotting with anti-His antibody.

Construction and Purification of Recombinant VEGFR2 KD Protein.

The inventors used "BacPAK Baculovirus expression system" from Clontech Inc. In brief, the pGEM-Teasy-VEGFR2 KD-His created above was inserted into a transfer vector, pBacPAK8, by PstI/NotI restriction enzyme sites followed by in vivo recombination with BacPAK6 viral DNA in SF21 insect cells. Plaque selection and expression confirmation of VEGFR2 KD in SF21 insect cells were performed according to manufacturer's instruction. Subsequent VEGFR2 purification was performed as previously reported (McTigue et al., 2012; Leppanen et al., 2010). In brief, VEGFR2 KD was overexpressed in SF21 insect baculovirus expression system at high multiplicity. Three days after infection, cell pellets were lysed by dounce homogenization and short sonication in 20 mM Tris, pH 8.0, 10 mM imidazole, 20 mM NaCl, 5% (v/v) glycerol, 1× protein inhibitors cocktail (Calbiochem) and 10 mM NEM (N-ethylmaleimide). The lysate was centrifuged for 50 min at 35,000 rpm using a Ti90 rotor. The soluble fraction was loaded onto a $Ni^{2+}$ charged chelating sepharose (GE Healthcare) column. Before sample loading, the column was equilibrated with five column volumes (CV) of cell lysis buffer. After sample loading, the column was washed with cell lysis buffer, then VEGFR2 KD was eluted with 20 mM Tris, pH 8.0, 500 mM imidazole, 20 mM NaCl, 5% (v/v) glycerol and protein inhibitors cocktail (Calbiochem). VEGFR2 KD was pooled for sodium dodecyl sulfate polyacrylamide gel electrophoresis (SDS-PAGE) analysis. Pooled material was loaded onto a 6 ml anion exchanger Resource Q column (GE Healthcare) and washed extensively with 20 mM HEPES, pH 8.0, 1 mM DTT, 1 mM EDTA. Protein was eluted using a 60 ml linear NaCl gradient in 20 mM HEPES, pH 8.0, 500 mM NaCl, 1 mM DTT, 1 mM EDTA. Finally, VEGFR2 KD was purified by gel filtration on a Superdex 200 (GE Healthcare) column in 20 mM HEPES, pH7.5, 150 mM NaCl and 5% glycerol.

SPR (Biacore) Analysis of UPI-VEGFR2 Binding Affinity.

Binding of UPI or UPI-Mut (Q9A, A13S, and K16A) peptides to VEGFR2 KD were analyzed with surface plasmon resonance (SPR) in the Biacore 2000 biosensor (GE). CM5 biosensor chip flow cells were covalently coated with the recombinant VEGFR2 KD via standard amine coupling. The binding was analyzed in running buffer of 20 mM HEPES pH 7.5, 150 mM NaCl, and 5% glycerol. The kinetics of peptide interaction with VEGFR2 KD was determined by varying the ligand concentrations over a surface to which a specified concentration of receptors had been coupled. The contact time of peptides was 2 min and the flow rate was 5 ml/min. The flow cells were regenerated after every injection with 10 mM Glycine, pH 1.7. The data were evaluated by subtracting the sensorgram obtained from the empty control flow cell from the sensorgram of the flow cells containing VEGFR2 KD. Assuming 1:1 binding, the dissociation constant was determined using SigmaPlot8.0 Software package.

UIM Peptide Competition (Epsin1-VEGFR2 Interference) Assay.

Epsin 1-HA (tag) and VEGFR2 KD-His(tag) were co-transfected into 293T cells using Lipofectamine 2000 (manufacturer's protocol). After 20 hours, cells were lysed in detergent-free hypotonic buffer (5 mM $NaCl_2$ in 10 mM HEPES, pH 7.4) containing protease inhibitor cocktail (Roche) and 10 mM NEM (N-ethylmaleimide). Cells were homogenized in dounce homogenizer 10 times. Cell lysates were centrifuged at 13,000 rpm at 4° C. for 10 min, and then the cleared supernatant collected. After incubating for 4 hr at 4° C. with 300 µM peptide(s), supernatants were adjusted to isotonic condition by adding $NaCl_2$ up to 150 mM. Anti-His tag antibody (GenScript) was then added for immunoprecipitation (2 µg antibody in 200 µL lysates) at 4° C. overnight. Immunocomplex was precipitated by addition of 30 µL rec-protein G beads (Invitrogen). Beads were washed 5 times in isotonic buffer with protease inhibitors. Samples were boiled for 5 min using 2× sample loading buffer prior to Western blotting.

UPI Peptide Binding to Angiogenic Receptors in $HUVEC^{\alpha v \beta 3}$ by Biotin-ELISA Assay Cultured $HUVEC^{\alpha v \beta 3}$ cells were treated with angiogenic factor VEGF (or PDGF, EGF, FGF) and harvested. Cells were lysed in a buffer containing 25 mM Tris-HCl (pH 7.6), 150 mM NaCl, 0.25% NP-40 and 0.25% sodium deoxycholate with 1× protease inhibitors and 20 mM NEM. Two mg cell lysates were co-incubated with biotinylated UPI or control peptides with anti-VEGFR2 antibody (or anti-PDGFR-β, anti-EGFR, anti-FGFR1) and rec-G beads (Invitrogen) for immunoprecipitation. Immunocomplex were washed with lysis buffer and Immunocomplex was eluted using 50 µl of low pH elution buffer (0.1 M Glycine pH 2.0) at room temperature for 10 min. Eluted supernatant was collected, followed by an addition of 1-3 µL of neutralization buffer (1 M Tris, pH 9.5) to balance the pH. The eluted samples were subjected to biotin-ELISA analysis (MyBioSource). Background was subtracted from a basal sample (without adding peptide).

Bioinformatic Analysis of UPI Peptides and Putative Binding with VEGFR2:

(1) Molecular Dynamics Simulation: Three-dimensional (3D) structures of UIM and UPI were predicted by PEP-FOLD (bioserv.rpbs.univ-paris-diderot.fr/PEP-FOLD) (Maupetit et al., 2009). Models were clustered by the sOPEP energy value (the coarse grained energy), then ranked based on their cluster scores. The top 5 clusters were used for the proposed native and near-native conformations. PEP-FOLD yielded a predicted model with an average root mean square deviation (RMSD) of 2.1 Å based on NMR structure (Thevenet et al., July).

(2) Molecular Docking Procedure: Docking experiments were performed using ClusPro program (Comeau et al., 2004). 3D crystal structures of ubiquitin (PDB ID: 1UBQ) and VEGFR2 kinase domain (PDB ID: 3U6J) were obtained from NCBI Protein Database. Apo-open crystal structure of VEGFR2 kinase domain was obtained by removing pyrazolone, the co-crystallized VEGFR2 kinase inhibitor, from its binding site. Simulated models of UIM and UPI peptide were then docked into ubiquitin or VEGFR2 kinase domain independently to generate predicted binding models of UIM-Ub, UPI-Ub, UIM-VEGFR2 and UPI-VEGFR2. The obtained UPI-Ub model with the high scores and best topologies was further docked into VEGFR2 kinase domain to generate the model of UPI-Ub-VEGFR2 super complex.

Standard and Previously Published Methodologies.

Western blotting, Hematoxylin and Eosin (H&E) staining, immunohistochemistry (IHC), immunofluorescence staining (IF), confocal microscopy, transmission electron microscopy (TEM), and cell culture maintenance, were performed according to standard methodologies. Confocal images were captured using an Olympus IX81 Spinning Disc Confocal Microscope with an Olympus plan Apo Chromat 60× objective and Hamamatsu Orca-$R^2$ Monochrome Digital Camera C1D600. Site-directed mutagenesis was performed using QuikChange II XL Site-Directed Mutagenesis Kit" (Agilent Technologies, Inc) and confirmed by DNA sequencing (OMRF Sequencing Facility). HUVEC transfection, FACS analysis, in vitro angiogenesis assays, VEGF signaling and VEGFR2 internalization assays were performed as previously described (Pasula et al., 2012). In vivo FITC-dextran perfusion assays to evaluate vessel function were performed as previously described (Pasula et al., 2012).

Statistical Analysis.

Data were presented as the mean±SEM. Data were analyzed by a two-tailed student's t test or ANOVA with Bonferron's procedure for multiple comparisons. A p value of less than 0.05 was considered statistically significant.

TABLE 1

Peptide sequences used in this study

| Name of peptide* | Peptide sequence | Total number of amino acids |
|---|---|---|
| UIM of Epsin | SGEEELQLQLALAMSKEE (SEQ ID NO: 1) | 18 |
| UIM of Hrs | QEEEELQLALALSQSEAEEK (SEQ ID NO: 37) | 20 |
| UIM of Eps15 | SEEDMIEWAKRESEREEEQR (SEQ ID NO: 38) | 20 |
| AP (penetratin) | RQIKIWFQNRRMKWKK (SEQ ID NO: 12) | 16 |
| iRGD | CRGDK/RGPD/EC (SEQ ID NO: 36) | 9 |
| PM anchoring | MGCIKSKRK (SEQ ID NO: 4) | 9 |
| Control peptide (Scrambled UIM) | QSLQESGMELEAELALEK (SEQ ID NO: 39) | 18 |

*PM: Plasma Membrane; AP: Antennapedia peptide (penetratin)

TABLE 2

Design of chimeric UIM peptides

| Name of peptide | Tracking marker at the N-terminal | Chimeric UIM peptide | Chimeric UIM peptide sequences** | Total number of amino acids |
|---|---|---|---|---|
| AP-UIM | ±FITC | (F)-AP-UIM | (Fluo-)-*RQIKIWFQNRRMKWKK* SGEEELQLQLALAMSKEE (SEQ ID NO: 40) | 34 |
| [F]UI | ±FITC | (F)-UIM-iRGD⁺ | (Fluo-)-SGEEELQLQLALAMSKEE CRGDKGPDC (SEQ ID NO: 41) | 27 |
| [F]UPI | ±FITC | (F)-UIM-PM-iRGD⁺ | (Fluo-)-SGEEELQLQLALAMSKEE MGCIKSKRKCRGDKGPDC (SEQ ID NO: 42) | 36 |
| UPI-Mut (Triple mutant) | N/A | UIM-PM-iRGD | SGEEELQIALALSMSAE**EMGCIKSKRKCRG DKGPDC (SEQ ID NO: 43) | 36 |
| Hrs-UIM | N/A | Hrs-UIM-PM-iRGD | QEEEELQLALALSQSEAEEKMGCIKSKRKC RGDKGPDC (SEQ ID NO: 44) | 38 |
| Eps15-UIM | N/A | Eps15-UIM-PM-iRGD | SEEDMIEWAKRESEREEEQRMGCIKSKRKC RGDKGPDC (SEQ ID NO: 45) | 38 |
| Control peptide 1 | ±FITC | (F)-Scrambled-control-1 | (Fluo)QSLQESGMELEAELALEK** MGCIKSKRKCRGDKGPDC (SEQ ID NO: 46) | 36 |
| Control peptide 2 | ±FITC | (F)-Scrambled-control-2 | (Fluo-)-*RQIKIWFQNRRMKWKK* QSLQESGMELEAELALEK*** (SEQ ID NO: 47) | 34 |

Note:
(1) AP: Italics and in Bold; Italics: UIM; Underlined: IRGD; Italics and underlined: PM anchoring peptide;
(2) UPI-Mut: indicating triple mutation (Q9→A9, A13→S13, K16→A16)
(3) ***Scrambled epsin UIM peptide; ⁺iRGD is cyclic;
(4) peptides were synthesized over 95% purity; If not specifically indicated, all peptides are synthesized using D-isomers of amino acids;
(5) In in-vitro binding assays, biotin-ELISA or biochemical pulldown assays, peptides were biotinylated.

TABLE 3

UPI peptide toxicity assays-plasma biomarkers

| | ALB (U/dL) | AST (U/L) | ALT (U/L) | BUN (mg/dL) | CK (U/L) | CREA (mg/dL) | GGT (U/L) | LDH (U/L) | TBIL (mg/dL) |
|---|---|---|---|---|---|---|---|---|---|
| PBS Ctr | 2 ± 0.2 | 66.5 ± 2.1 | 63.5 ± 20.5 | 20.0 ± 2.0 | 201.5 ± 33.2 | 0.170 ± 0.01 | <5 | 525.5 ± 62.9 | <0.01 |
| 10 mg/kg | 1.98 ± 0.1 | 62.3 ± 3.6 | 63.5 ± 10.8 | 18.0 ± 0.8 | 163.5 ± 50.0 | 0.173 ± 0.02 | <5 | 397.8 ± 26.0 | <0.01 |
| 25 mg/kg | 2.0 ± 0.1 | 55.0 ± 5.3 | 65.3 ± 4.0 | 18.7 ± 2.5 | 165.7 ± 8.6 | 0.160 ± 0.02 | <5 | 365.7 ± 77.9 | <0.01 |
| 50 mg/kg | 2.2 ± 0.2 | 52.0 ± 4.4 | 71.7 ± 6.0 | 21.0 ± 2.0 | 153.7 ± 33.9 | 0.180 ± 0.02 | <5 | 481.5 ± 12.1 | <0.01 |
| P value* | 0.8457 | 0.154 | 0.8652 | 0.1233 | 0.3985 | 0.8322 | N/A | 0.189 | N/A |

*Statistical analysis: One-way ANOVA
Description of biomarkers in blood test
ALB: Albumin; generated by liver and required to keep fluid from leaking out of blood vessels;
AST: Aspartate aminotransferase; when body tissue or an organ such as the hear tor liver is diseased or damaged, additional AST is released into the bloodstream, high AST suggests organ damage.
ALT: alanine aminotransferase, predominantly contained within liver cells and to a lesser degree in the muscle cells. If the liver is injured or damaged, the liver cells spill this enzyme into the blood, raising the ALT enzyme;
BUN: Blood Urea Nitrogen; generally, a high blood urea nitrogen level means kidneys aren't working well;
CK: Creatine kinase; indicator of muscle function; levels of CK rise after a heart attack, skeletal muscle inury;
CREA: A Creatinine test reveals important information about kidneys; CREA high means kidney not functional properly (Waste Filtration);
LDH: Lactate dehydrogenase; LDH is most often measured to check for tissue damage. The protein LDH is in many body tissues, especially the heart, liver, kidney, muscles, brain, blood cells, and lungs. When tissues are damaged by injury or disease, they release more LDH into the bloodstream.
GGT: Gamma-glutamyl transpeptidase: Testing for GGT helps doctors evaluate diseases of the liver, gallbladder, and bile ducts (tubes that carry bile from the liver to the gallbladder and intestine). It also can be used to check for liver damage related to ingestion of toxic substances or alcohol abuse;
TBIL: Total Bilirubin. Bilirubin is a normal component of red blood cells. When these cells break down free bilirubin is released in the blood. Bilirubin is then carried to the liver where it is broken down and excreted. When the liver is not functioning properly, bilirubin builds up in the body, causing jaundice (yellowing of the skin and eyes and darkening of the urine). TBIL is raised in acute liver disease.

TABLE 4

Molecular modeling prediction of putative interacting residues between UPI peptide and VEGFR2 kinase domain

| UPI peptide | VEGFR2 kinase domaine | H-bonds (Å) |
|---|---|---|
| Q9 | R1027 | 2.72 |
| | I1025 | 3.15 |
| | I1053 | 3.08 |
| A13 | R1027 | 2.76 |
| K16 | R1027 | 2.40 and 3.03 |
| | R1080 | 3.05 |
| | D1064 | 3.08 |

*Only showing part of predicted interacting residues.

TABLE 5

Site-directed mutagenesis

| Point mutations | Residues | Mutated to | Mutation type | Notes |
|---|---|---|---|---|
| VEGFR2 KD | R1027, R1080 | All to Ala | Double mutations | UPI-VEGFR2 binding |
| UPI(Epsin-UIM) | A9, A13, K16 | Q9→A A13→S K16→A | Triple mutations | UPI-VEGFR2 binding |

* Oligos for site-directed mutagenesis and mutated plasmids are available for request.
** Mutation direction was predicted using online tools.

B. Results

Novel Tumor Targeting Epsin Inhibitory Peptide Exclusively Homes to Tumor Vessels and Inhibits Tumor Growth and Metastasis.

The inventors postulated that a synthetic UIM peptide designed to competitively prohibit epsin from binding to VEGFR2 could disrupt functional tumor angiogenesis and thereby tumor growth (Pasula et al., 2012). Toward this end, they chemically synthesized a UIM-containing, tumor vasculature-targeting peptide, referred herein as UPI (FIG. 1A; Tables 1 and 2). Specifically, they conjugated the C-terminus of a UIM peptide to the tumor endothelial cell-homing peptide iRGD, which facilitates peptide homing to and internalization by tumor endothelial cells (Sugahara et al., 2009 and Sugahara et al., 2009) iRGD mediates the specific uptake of iRGD-conjugated peptides by tumor endothelial cells by first binding αvβ3 or αvβ5 integrin, then neuropilin-1, overexpressed on the surface of tumor endothelial cells (Sugahara et al., 2010). To further enrich the plasma membrane localization of the UIM peptide conjugate, a plasma membrane anchoring peptide from the Lyn Kinase H4 domain (Chen & De Camilli, 2005 and Kovarova et al., 2001) known to bind lipid rafts through palmitoylation and myristoylation was inserted between UIM and iRGD. Molecular modeling revealed that this novel UPI peptide forms a helical structure and, consistent with epsin UIM function, binds ubiquitin similarly to the published UIM of yeast Vps27 (FIG. 1A; FIGS. 5A-C) (Swanson et al., 2003). As a positive control, the inventors also conjugated the non-selective plasma membrane permeable peptide, Antennapedia (AP) (also known as penetratin) (Joliot & Prochiantz, 2004), to the N-terminus of the UIM peptide, thus creating AP-UIM (Tables 1 and 2).

Figure 8:
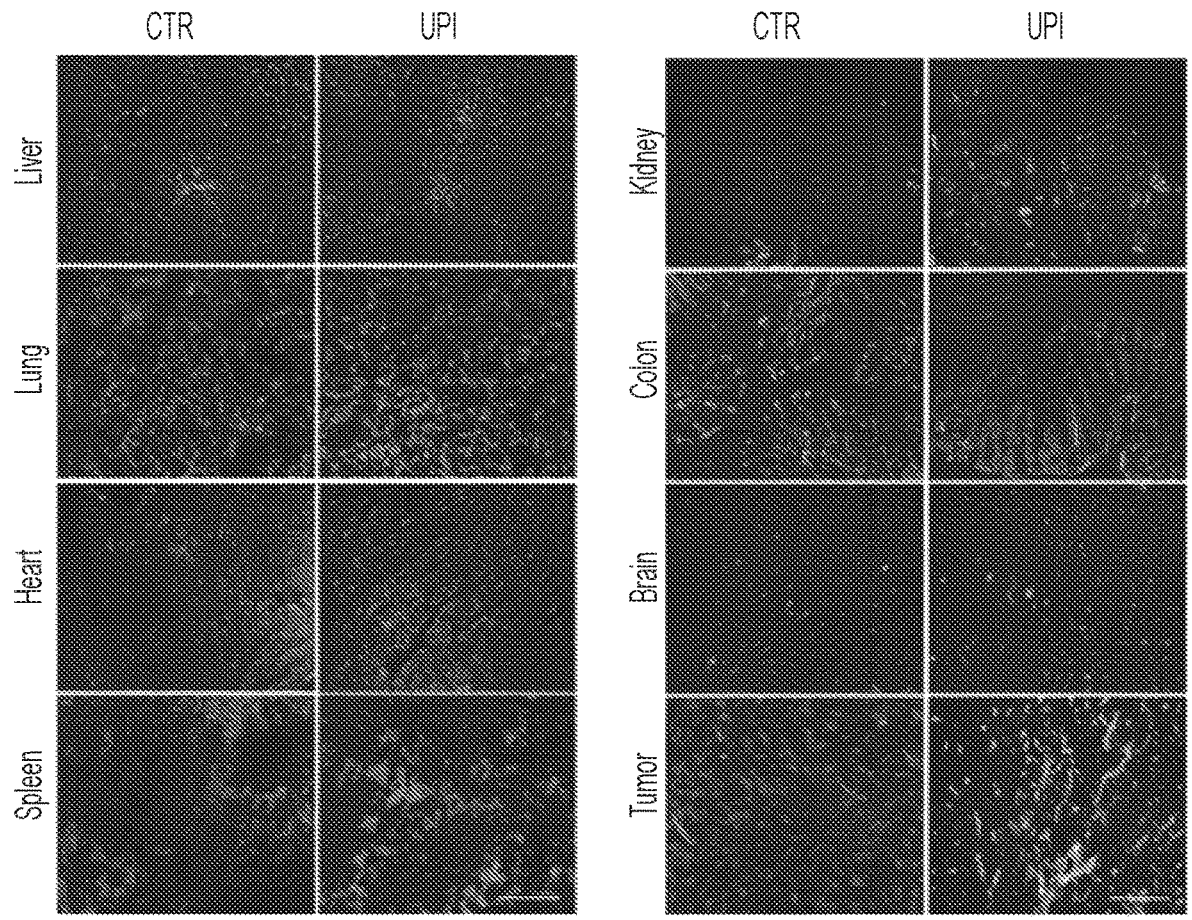
FIG. 8. FUPI peptide specifically homes to tumors. B16 tumor-bearing mice were sacrificed at 24-hr time point after control (PBS) or FUPI peptide injection (10 mg/kg, i.v.-injection). Tumor and major organs were stained with CD31 (red) and imaged at red channel (CD31), blue channel (DAPI) and green channel (FUPI). Note that green (FITC) is seen only in tumors. Yellowish color suggests the FUPI peptide and CD31 colocalize in vessels. Other major organs (liver, lung, heart, spleen, kidney, colon, brain, etc) are free of green color, n=4; scale bar: 200 µm.

To ensure targeting specificity and efficacy of the UPI, the inventors treated HUVEC overexpressing αvβ3 integrin (HUVEC$^{αvβ3}$) with FITC-conjugated UPI (FUPI) or AP-UIM (FITC-AP-UIM) (Table 2). Normal quiescent endothelial cells, such as HUVEC, express endogenous αvβ3 integrin. However, compared to tumor endothelial cells this expression is considerably lower. By overexpressing αvβ3 integrin in HUVEC, the inventors distinguished peptide targeting to endothelial cells in quiescent versus tumor vasculature. Overexpression of αvβ3 integrin was monitored by FACS and Western blotting (FIGS. 6A-C). As predicted, FUPI peptide accumulated selectively in HUVEC$^{αvβ3}$, but not in HUVEC alone (FIG. 1B). Importantly, accumulation was highly enriched at the plasma membrane (FIG. 6D), mirroring the steady state intracellular localization of epsins. In contrast, the non-selective FITC-AP-UIM accumulated in both HUVEC and HUVEC$^{αvβ3}$ as expected (FIG. 6E). Given the selective nature of the UPI peptide in vitro, the inventors next validated its tumor vascular-targeting efficacy in vivo after intravenous (i.v.) administration into Lewis lung carcinoma (LLC) and B16F10 (B16) melanoma subcutaneous tumor-bearing mice. To circumvent stability issues common in i.v. administered peptide drugs, the inventors designed a cyclic iRGD homing sequence (Bogdanowich-Knipp et al., 1999) within the UPI (FIG. 1A) and utilized D-isomers during peptide synthesis; both of which protect the peptide from circulating peptidases (Plescia et al., 2005). Pharmacokinetic analysis demonstrated that D-amino acid-containing peptides were stable when added to plasma ex vivo and incubated at 37° C. (FIG. 7A). Intravenous injection of FUPI into mice harboring established subcutaneous LLC or B16 melanoma tumors revealed significant concentration within tumor vasculature, but not other major organs including liver, lung, heart, spleen, kidney, colon and brain (FIG. 1C; FIG. 8). This finding supports a function for iRGD in homing to tumor endothelium (Sugahara et al., 2009). Additional biomarker analysis of PBS or UPI peptide-treated mice revealed no statistical differences in kidney, liver or muscle functions (Table 3), indicating that the UPI peptide treatment does not interfere with major physiological functions. Consistent with the in vitro data, FUPI localized to and was retained within the vessels of B16 melanoma tumors for up to 48 hours after injection (FIGS. 7B-C). These findings strongly suggest that the UPI peptide effectively and specifically homes to tumor vasculature when administered intravenously.

To investigate the therapeutic potential of these novel tumor vessel-targeting UPI peptide, LLC subcutaneous tumor-bearing mice with established tumors 20-50 mm$^3$ in size (approximately 12 days post-implantation) were injected intravenously with UPI peptide on alternating days for 14 days using concentrations of 2.5, 5, and 10 mg/kg. Control peptide was i.v. injected at 10 mg/kg. LLC tumor growth, monitored on alternating days during peptide administration, was significantly impeded by UPI peptide in a dose-dependent manner with 10 mg/kg yielding maximal inhibition (FIG. 1D). Similarly, UPI peptide administered intravenously at 10 mg/kg every-second-day effectively impaired subcutaneous B16 melanoma tumor growth (FIG. 1E). Using the same dosing regimen (10 mg/kg, iv-injection) initiated 12 days post-tumor implantation, UPI but not control peptide treatment significantly retarded subcutaneous human U87 tumor growth in SCID mice (FIG. 1F). To evaluate therapeutic potential in a spontaneous tumor model, the inventors also utilized Transgenic Adenocarcinoma of Mouse Prostate (TRAMP) mice, which develop progressive prostate cancer between 10 and 20 weeks of age with 100% frequency (Greenberg et al., 1995). The inventors began by administering 20 mg/kg of UPI peptide by intraperitoneal (i.p.) injection on alternating days at 20 weeks of age to establish tumor presence prior to peptide delivery. Mice were sacrificed at 35 weeks and examined for primary prostate tumors. While large tumors were observed in the prostate and nearby seminal vesicles of control peptide-treated TRAMP mice, smaller and less frequent tumors were observed in mice receiving UPI peptide treatment (FIG. 1G; FIG. 9A). These data strongly support the hypothesis that utilizing homing sequences to specifically target epsin UIM to tumor vascular endothelial cells is a potential therapeutic approach to combat tumor growth. Further, by utilizing the plasma membrane targeting sequences to effectively home the UPI peptide to the plasma membrane of tumor endothelial cells, the inventors achieved significantly greater tumor inhibition relative to AP-UIM or UIM peptide containing only iRGD (UI peptide) (FIG. 9B), reinforcing the importance of plasma membrane microenvironment enrichment of the UIM peptide offered by the plasma membrane anchoring sequence.

Given the targeted specificity of the UPI peptide to tumor vasculature and the functional importance of tumor angiogenesis for establishing metastatic potential (Zetter, 1998; Zetter, 1998 and Saharinen et al., 2011), the inventors reasoned that the UPI peptide may impair metastasis by disrupting functional tumor angiogenesis. Because of the aggressive nature of the spontaneous TRAMP model and subcutaneous B16 melanoma model, the inventors proceeded to monitor tumor metastasis in the UPI peptide-treated TRAMP mice and B16 tumor-bearing mice. Because of the aggressive nature of the spontaneous TRAMP model and subcutaneous B16 melanoma model, the inventors proceeded to monitor tumor metastasis in the UPI peptide-treated TRAMP mice and B16 tumor-bearing mice. Gross morphological analysis, as well as H&E staining, revealed dramatic reductions in the frequency of metastasis in lungs and liver of UPI peptide-treated TRAMP mice (FIG. 1H). Accordingly, expression of the cancer cell marker, vimentin, and metastatic marker, snail, were significantly reduced in the lung and liver isolated from UPI peptide-treated TRAMP mice (FIG. 1I). Importantly, TRAMP mice receiving UPI peptide treatment (20 mg/kg; every-other-day by i.p.) had an average increased life expectancy of 3 months or beyond (FIG. 1J). However, smaller tumors metastasize less frequently, and since UPI peptide-treatment reduced primary tumor size in TRAMP mice, the inventors cannot rule out that reduced metastasis is not a secondary result of impaired primary tumor growth. To address this, the inventors utilized B16 melanoma tumor-bearing mice. After primary B16 tumors reached 400-500 mm$^3$ they were surgically removed, then mice were randomized into two groups and post-operatively administered control or UPI peptide (10 mg/kg, every-other-day by i.v.) for five weeks. UPI peptide treatment significantly inhibited B16 melanoma metastasis to lymph node and lung (FIGS. 1K-L), decreased vimentin and melan-a (specific melanoma marker) immunofluorescence staining (FIGS. 1K-L), reduced the frequency of metastasis, the number of metastatic cancer cells in lymph nodes and the number of tumor nodules (foci) in lungs, and attenuated vimentin and snail protein expression (FIG. 1M). Collectively, these data indicate UPI peptide administration not only impedes primary tumor growth but also significantly attenuates metastasis, presumably by disrupting functional tumor angiogenesis.

UPI Peptide Selectively Disrupts Epsin-VEGFR2 Interaction and Prevents Epsin-Mediated VEGFR2 Downregulation.

To explore the molecular basis underlying the therapeutic efficacy of the UPI peptide, the inventors examined the competitive binding of UPI peptide in 293T cells overexpressing the VEGFR2 kinase domain (KD) and epsin 1. Cell lysates were incubated with control or UPI peptides followed by co-immunoprecipitation analysis of VEGFR2 KD and epsin 1. UPI, but not control peptides significantly abolished epsin 1 interaction with VEGFR2 KD (FIG. 2A). Importantly, UPI peptides consisting of either D- or L-isomer amino acids exhibited similar inhibitory effects on epsin 1-VEGFR2 KD binding (FIG. 10A), further supporting the use of D-UPI peptides in in vivo studies. Additionally, UPI peptide treatment effectively inhibited endogenous epsin 1-VEGFR2 binding when administered to intact HUVEC$^{\alpha v \beta 3}$ and analyzed by co-immunoprecipitation assay of epsin 1 by VEGFR2 (FIG. 10B). Importantly, UPI peptide-mediated inhibition of the epsin 1-VEGFR2 interaction augmented VEGF-induced VEGFR2 phosphorylation (FIG. 2B) and increased phosphorylation of downstream effectors, PLCγ and ERK (FIG. 2C; FIG. 10C). Consistent with enhanced signaling, cell surface biotin-labeled VEGF internalization assays and FACS analysis of cell surface VEGFR2 expression in UPI peptide-treated HUVEC$^{\alpha v \beta 3}$ revealed impaired endocytosis of VEGFR2 and substantial increases in VEGFR2 accumulation at the plasma membrane (FIGS. 10D-E), suggesting that the UPI peptide inhibits VEGFR2 endocytosis and degradation. To test the specificity of UPI peptide-mediated targeting on the VEGF signaling pathway, HUVEC$^{\alpha v \beta 3}$ were treated with a combination of control or anti-VEGF antibody and either UPI or control peptide prior to VEGF stimulation. Anti-VEGF antibody administration suppressed UPI peptide-mediated increases in VEGFR2 phosphorylation (FIGS. 11A-B). Collectively, these studies endorse the design of the UPI peptide as an inhibitor of epsin function selectively on VEGFR2 signaling in endothelial cells.

Multistep enrichment of the UPI peptide in tumor endothelial cells and sustained VEGF-dependent VEGFR2 signaling could prove critical for maximizing UPI peptide-mediated tumor inhibition through aberrant tumor angiogenesis. However, whether UPI peptide targets other angiogenic signaling pathways in addition to VEGFR2 is unknown. To address this, the inventors co-incubated biotinylated UPI or control peptides and Neutri-Avidin beads in lysates from LLC ex vivo tumors. Western blot analysis of pulldowns showed strong co-precipitation of VEGFR2 by UPI peptide (FIG. 2D). However, UPI peptide failed to co-precipitate EGFR, FGFR1 or PDGFR-β, suggesting that the UPI peptide binds VEGFR2 specifically; a finding consistent with epsin specificity for VEGFR2 (Pasula et al., 2012). This result was further confirmed using biotinylated UPI peptide in an ELISA assay (FIG. 11C). To further investigate the targeting specificity of UPI peptide for VEGFR2, downstream signaling of EGFR, FGFR1, PDGFR-β and TGFβ-R1 were assessed after UPI peptide treatment of HUVEC$^{\alpha v \beta 3}$ (FIG. 2E; FIGS. 11D-F). Consistently, these major angiogenic receptor signaling pathways were not affected by UPI peptide. Similarly, VEGFR2, but not other angiogenic receptors, was increased in tumors from UPI peptide treated tumor-bearing mice (FIGS. 11G-I). Additionally, UPI peptide did not alter endogenous epsin protein levels in both HUVEC$^{\alpha v \beta 3}$ cells and tumors (FIGS. 11J-K), or VEGFR1 and Notch signaling in HUVEC$^{\alpha v \beta 3}$ cells (FIGS. 12A-D). Notably, no VEGFR3 expression was detected in HUVEC$^{\alpha v \beta 3}$ cells (FIG. 12A). These findings in combination with the observation that in vivo co-injection of UPI peptide with anti-VEGF antibody or VEGFR2 kinase inhibitor impaired UPI peptide therapeutic efficacy (FIG. 2F), suggest that UPI peptide specifically targets to activated VEGFR2.

To interrogate UPI peptide as a competitive inhibitor of epsin function specifically targeting VEGFR2 in vivo, several recently generated unique animal models were used to establish LLC tumor models, including inducible endothelial cell-specific epsin deficient mice (EC-iDKO), wild type mice or EC-iDKO mice heterozygous for VEGFR2 (WT-Flk and EC-iDKO-Flk, respectively), and EC-iDKO mice that express a transgene encoding an active Notch, NICD to rescue defective Notch signaling in EC-iDKO mice, hence referred as EC-iDKO-Notch mice (FIG. 13). Loss of a single VEGFR2 allele in wild type mice (WT-Flk) significantly hinders VEGF signaling and, thereby, tumor growth compared to wild type mice (FIG. 2G, FIG. 14A). Administering UPI peptide rescued the retarded tumor growth phenotype of WT-Flk mice (FIG. 2G) because the UPI peptide acts as an inhibitor of VEGFR2 internalization and degradation resulting in sustained VEGFR2 signaling and normalized tumor angiogenesis (FIG. 14A). In contrast, UPI peptide treatment of either EC-iDKO or EC-iDKO-Flk mice, where epsins are specifically knocked out in endothelial cells, did not alter tumor volumes compared to control peptide (FIG. 2G), implying that UPI peptide modulates tumor growth via its effect on the epsin-VEGFR2 interaction (FIG. 14B); since epsins are deleted, UPI peptide is no longer effective. Further, no difference in tumor growth between EC-iDKO mice and EC-iDKO-Notch mice was seen upon UPI peptide treatment, suggesting that UPI peptide does not affect tumor angiogenesis through the Notch pathway (FIG. 2H). By utilizing these genetically modified animal models in combination with pharmacological studies, the inventors concluded that UPI peptide hinders tumor growth by specifically inhibiting epsin-VEGFR2 binding, resulting in elevated VEGFR2 signaling and aberrant tumor angiogenesis.

It is well established that epsin UIM binds ubiquitinated cell surface receptors, such as activated VEGFR2 (Pasula et al., 2012 and Tessneer et al., 2014), partially via its highly conserved, albeit weak and non-specific interaction with ubiquitin (FIG. 5C). However, the molecular mechanisms driving the specificity with which epsin UIM and the UPI peptide interact with VEGFR2, but not other ubiquitinated angiogenic receptors, in endothelial cells remains unknown. To delineate the molecular interactions mediating this specificity, the inventors used de novo structural prediction and molecular modeling. Their model predicts that UPI peptide can dock directly into a previously unidentified pocket in the VEGFR2 cytoplasmic domain (FIG. 5D). The UIM residues predicted to mediate this docking are unique to epsin UIM (Q9, A13 and K16) and may play a critical role in mediating the specific interaction with residues R1027 and R1080 of VEGFR2 (FIGS. 2I-J; Table 4). Therefore, the inventors speculated that Q9, A13 and K16 in epsin UIM possess specific biological functions for regulation of the epsin-VEGFR2 interaction, and tumor angiogenesis. To test this hypothesis, they generated a series of point mutations within these critical UIM and VEGFR2 residues (Table 5) and used co-immunoprecipitation with anti-VEGFR2 or anti-epsin 1 to evaluate effects on epsin 1-VEGFR2 binding. Predictably, Q9A/A13S/K16A triple mutations in epsin UIM attenuated epsin 1-VEGFR2 interactions in 293T cells (FIG. 2K). Reciprocally, R1027A and R1080A mutations in VEGFR2 also decreased epsin 1-VEGFR2 interactions (FIG. 2L). These data strongly support the inventors' molecular model predictions of a novel UPI binding pocket within VEGFR2 that provides the specificity with which the UPI peptide modulates VEGFR2 function.

To substantiate the above mutation studies, the inventors generated a UPI-Mut peptide bearing the Q9A/A13S/K16A triple mutation in the epsin UIM (Table 2). Consistently, UPI-Mut peptide failed to disrupt epsin-VEGFR2 interaction indicating reduced binding of UPI-Mut peptide to VEGFR2 and failed competitive inhibition of epsin (FIG. 2M). To definitively determine the importance of these critical residues in controlling epsin binding-affinity to VEGFR2, surface plasmon resonance (SPR) was employed to analyze the binding affinity between recombinant VEGFR2 KD and wild-type or mutant UPI peptides. UPI-Mut peptide significantly reduced the binding affinity compared to wild type UPI peptide (FIG. 2N). To evaluate whether the reduced binding affinity of UPI-Mut peptide could attenuate UPI peptide binding to VEGFR2 in ex vivo LLC or GL261 tumors, the inventors co-incubated biotinylated UPI, UPI-Mut or control peptide and Neutr-Avidin beads for pulldown of VEGFR2 in homogenized tumor lysates. As shown in FIGS. 15A-D, UPI-Mut peptide exhibited reduced binding to VEGFR2. In agreement with previous results, neither UPI nor UPI-Mut peptide pulled down EGFR, FGFR1 or PDGFR-β (FIGS. 15A and 15C). Furthermore, UPI-Mut peptide administered to LLC tumor-bearing mice failed to inhibit tumor growth compared to mice treated with UPI peptide (FIG. 2O). Collectively, these data support a unique role for these three critical residues within the epsin UIM in driving the specificity of the epsin-VEGFR2 interaction.

Given that amino acid residues Q9, A13 and K16 are unique to the epsin UIM, the inventors wanted to determine their significance in facilitating epsin-VEGFR2 binding. To do this, they replaced the epsin UIM in the UPI peptide with UIMs from other endocytic proteins including Eps15 and Hrs, creating peptides Eps15-UIM and Hrs-UIM (Tables 1 and 2). Importantly, when administered to LLC tumor-bearing mice, neither Eps15-UIM nor Hrs-UIM peptides affected tumor growth (FIG. 2P). These results were similar to those obtained using the UPI-Mut peptide, and contrast with the effective tumor inhibition promoted by the UPI peptide, thus emphasizing the unique qualities within the epsin UIM that enable it to specifically interact with VEGFR2 to modulate VEGF signaling and tumor angiogenesis.

UPI Peptide Promotes In Vitro and In Vivo Neoangiogenesis and Disrupts Tumor Angiogenesis by Stabilizing VEGFR2 Signaling.

The inventors reasoned that this specific mode of action of the UPI peptide would impair VEGFR2 signaling downregulation and thus promote VEGF-induced angiogenesis in in vitro angiogenesis assays. Control and UPI peptides were used to treat HUVEC$^{\alpha v \beta 3}$ in the presence or absence of VEGF. UPI peptide treatment greatly elevated VEGF-induced HUVEC$^{\alpha v \beta 3}$ proliferation as determined by BrdU labeling (FIG. 3A), migration using wound-healing assays (FIG. 3B), and tube formation in a three-dimensional matrix gel assay (FIG. 3C).

To complement the above in vitro angiogenic assays, the inventors examined the effect of the UPI peptide in regulating neoangiogenesis using in vivo matrigel plugs and retina neovascularization models. Matrigel, pre-mixed with UPI or control peptide (100 μg/ml) in the presence or absence of VEGF, was subcutaneously implanted into C57BL/6 mice. Six days post-implantation, matrigel plugs were removed and processed for staining using the vascular endothelial marker, CD31. The UPI peptide promoted VEGF-stimulated in vivo neoangiogenesis as evident by increased new blood vessel formation in the UPI peptide-containing VEGF-positive matrigel plugs, relative to UPI peptide alone or control peptide plus VEGF (FIGS. 3D-E). Similarly, intra-ocular injection of UPI peptide (100 μg/ml) in mouse pups at postnatal day 1(P1), P3 and P5 caused a significant increase in retinal neoangiogenesis as determined by isolectin B4 immunofluorescence staining of retinas isolated at P6 (FIG. 3F). These findings strongly support the hypothesis that UPI is a pro-angiogenic agent that promotes both in vitro and in vivo neoangiogenesis.

Of significance, upon examination of tumor vessels from control and UPI peptide-treated subcutaneous LLC and U87 tumors (by CD31 staining), UPI peptide induced tumor vessel proliferation and promoted their dilation (FIGS. 3G-H). These aberrant vessel characteristics (indicative of aberrant tumor angiogenesis) are consistent with previous studies testing the effects of genetic epsin disruption on tumor angiogenesis (Pasula et al., 2012). Further, VEGFR2 protein levels were dramatically increased in both subcutaneous tumor models treated with UPI peptide (FIG. 3I), indicating impaired VEGFR2 degradation. Consistent with UPI peptide-mediated increase in angiogenic properties, including increased vessel number and dilation, VEGFR2 phosphorylation as determined by immunofluorescence of subcutaneous U87 tumor vasculature was significantly augmented by UPI peptide-injection (FIG. 3J), further validating the specificity of targeting of the UPI peptide to the VEGFR2 pathway.

UPI Peptide Treatment Produces Dysfunctional and Hyper-Leaky Tumor Vessels, and Retards Tumor Growth in Orthotopic Glioblastoma Models.

Given that administration of UPI peptide produced a striking morphological change in tumor vessels, the inventors examined the effects of this change on tumor vessel function. Subcutaneous U87 tumor-bearing mice were treated with control or UPI peptide for 3 weeks followed by perfusion with fixable FITC-dextran of large molecular weight. Mice were sacrificed and tumor vessels were stained with CD31. UPI, but not control peptide, produced extensive leakage of fluorescent dextran into tumor tissues (FIG. 4A), indicative of vessel hyper-permeability, which coincided with decreased α-smooth muscle actin (α-SMA) coverage of tumor vessels (FIG. 4B). Examination by transmission electron microscopy of subcutaneous tumors extracted from U87 tumor-bearing SCID mice revealed increased fenestrations and open cell-cell junctions between tumor vessel endothelial cells of UPI peptide-treated tumors (FIGS. 16A-B). Consequently, semi-thin sections showed prominent red blood cell leakage from tumor vessels accompanied by dying tumor cells in response to UPI peptide treatment (FIG. 4C; FIGS. 16C-D). Also, tumors from UPI peptide-treated mice exhibited profound increases in hypoxia (FIG. 4D), presumably a result of impaired vascular delivery of oxygen. Notably, the vascular effects of UPI peptide are limited to tumor vessels with negligible hyper-permeability or leakage such as that observed in quiescent vasculature of tissues like intestine (FIG. 4E), brain, kidney, stomach or liver (FIG. 17). These data further support results from plasma biomarker examination (Table 3) suggesting minimal toxicity of the peptide. Together, these data strongly suggest that UPI peptide treatment perturbs tumor vessel function specifically and results in profound leakage and damaging hypoxia.

Lastly, to determine pre-clinical implications of UPI peptide treatment as a potential human cancer therapeutic, the inventors employed mouse and human orthotopic glioma models. They began by orthotopically injecting mouse glioma cells, GL261, into the forebrain of C57BL/6 mice. When tumor size reached 10-20 mm$^3$ (approximately day 14 post-inoculation), mice were randomized into two groups receiving either control or UPI peptide (10 mg/kg) by i.v. injection every-other-day. Tumor growth was monitored on alternating days by MRI. UPI peptide treatment hindered tumor growth (FIG. 4F). MRI analysis of tumor growth at day 23 post-inoculation revealed significant tumor reduction in UPI peptide treated mice (FIG. 4G). Remarkably, UPI peptide treatment also prolonged survival of tumor-bearing mice beyond the study endpoint, with efficacy comparable to current anti-VEGF antibody therapy (FIG. 4H). To investigate the potential for application of the UPI peptide in a human cancer model, the inventors orthotopically implanted human glioma U87 cells in the right forebrain of the immune-deficient SCID mice and subjected them to i.v. injection of control or UPI peptide (10 mg/kg) every two days beginning after tumors were established (10-20 mm$^3$; approximately 9 days post-inoculation. Tumor growth was monitored as described above. Consistently, UPI peptide therapy depressed U87 glioblastoma tumor growth (FIG. 18). Strikingly, when tumors of equal size were compared, MRI analysis revealed severe necrosis in the glioma of UPI peptide-treated SCID mice, as evidenced by the appearance of large voids (FIG. 4I). Notably, tumors receiving UPI peptide required almost twice as much time to achieve similar tumor mass as control peptide treated tumors (35 days compared to 18 days). Elevated necrosis after UPI peptide administration corresponded tightly with heightened VEGFR2 in the tumor vasculature, which is indicated by in situ labelling analysis of vascular VEGFR2 (FIG. 4I). These data support the inventors' earlier conclusions that UPI peptide hinders tumor growth by exacerbating VEGFR2-mediated tumor angiogenesis. Further, the corresponding increase in necrosis strongly suggests that the dysfunctional and hyper-leaky tumor vessels resulting from UPI peptide treatment promote tumor cell death. The impaired tumor growth and enhanced tumor necrosis observed after UPI peptide administration likely contributed to the extended life expectancy of the U87 tumor-bearing SCID mice (FIG. 4J). Although significant, the extended life expectancy of UPI peptide treated human U87 glioma tumor-bearing SCID mice was not as dramatic as the increased life expectancy observed in GL261 glioma tumor-bearing C57BL/6 mice receiving UPI peptide therapy (FIG. 4H). Given the importance of a functional immune system in combating tumor development and progression (de Visser & Eichten, 2006), these results offer concrete support on the synergistic effect of the UPI peptide and the host immune defense on fighting tumor invasion. In summary, these data suggest that UPI peptide is a potent suppressive agent of tumor growth and metastasis, functioning by disrupting tumor angiogenesis. These data support this in various preclinical cancer models, including the human U87 glioblastoma model. The inventors also show that administration of the UPI peptide can significantly increase survival rates and extend life expectancy while imposing negligible toxicity.

C. Discussion

Tumor angiogenesis is a critical event in cancer progression and metastasis, making it an attractive target for anti-cancer therapeutic strategies (Ferrara & Kerbel, 2005; Ferrara & Kerbel, 2005; Carmeliet, 2003; Saaristo et al., 2000; Yancopoulos et al., 2000; Ridgway et al., 2006; Noguera-Troise et al., 2006 and Dikic & Schmidt, 2010). Previous therapeutic approaches have focused predominantly on inhibiting tumor angiogenesis by inhibiting pro-angiogenic signaling pathways such as VEGF and Notch. Alternatively, the inventors propose a distinct therapeutic strategy for suppressing tumor growth based on the discovery that loss of epsin-mediated VEGFR2 degradation also hindered tumor progression by impairing proper downregulation of VEGFR2 signaling (Pasula et al., 2012). This strongly suggests that inhibition of VEGFR2 signaling downregulation and subsequent uncontrolled tumor angiogenesis may be a valuable therapeutic strategy. The inventors discovered that the epsin UIM played a critical regulatory role in VEGFR2 internalization and downregulation (Pasula et al., 2012), thereby providing us with a strong therapeutic rationale to exogenously disrupt the interaction between epsin and VEGFR2 through competitive inhibition by the epsin UIM peptide. Here, the inventors report that a novel chimeric UPI peptide produces remarkable inhibition of tumor growth in LLC (lung), B16 (melanoma), TRAMP (prostate) and U87 and GL261 (glioblastoma) pre-clinical cancer models (FIGS. 1A-M; FIGS. 4A-K). By tagging the epsin UIM motif (Chen et al., 1998) with a tumor vasculature homing peptide, iRGD (Sugahara et al., 2009), and a plasma membrane anchoring sequence (Kovarova et al., 2001), they created a novel chimeric peptide that specifically targets tumor vasculature and concentrates at the endothelial cell plasma membranes close to activated VEGFR2. Localized delivery of the peptide to the tumor vasculature affords a lower dose of UPI peptide and negligible penetration into normal endothelium, both contributed to the minimal toxicity observed. Importantly, in vitro and in vivo angiogenic experiments (FIGS. 3A-J) demonstrate that the UPI peptide is an ideal mimetic of previously described anti-tumor phenotype in endothelial-specific epsin-deficient mice (Pasula et al., 2012). Here, it substantially stabilized VEGFR2 protein to enhance VEGFR2 signaling and produce disorganized, dilated and dysfunctional leaky tumor vessels (FIG. 3A-J; FIG. 4A-K). Consequently, this peptide not only retarded tumor growth, but also impeded cancer metastasis (FIGS. 1A-M). Its potent tumor inhibitory effect and minimum cytotoxicity provides a strong rationale for us as a translational cancer therapeutic.

Therapeutic efficacy is dependent on several aspects including localized delivery, minimal toxicity, enhanced stability and targeting specificity. As discussed above, incorporating both the iRGD homing sequence and plasma membrane anchoring sequence ensured effective delivery, epsin-specific inhibition occurring only in tumor endothelial cells, and minimal toxicity due to negligible penetration into normal endothelium (FIG. 1A). As a result, the UPI peptide showed minimal side effects when administered to mice for a prolonged period (FIG. 4E; FIG. 17 and Table 3). To enhance in vivo stability and protect against circulating peptidases, the UPI peptide was synthesized using D-isomer amino acids, and designed with a cyclic iRGD sequence (two cysteine residues that form a disulfide bond) (FIG. 1A). Incorporation of these modifications increased stability, evident in the 48 hr retention of UPI in vivo (FIGS. 7A-C). The inventors conclude from these data that the epsin UIM within their UPI peptide specifically targets VEGFR2, thereby competitively inhibiting endogenous epsin function and mirroring the tumor-inhibitory phenotype in epsin-deficient animals. This specificity was determined through the use of pharmacologic agents, genetically modified animal models, biochemical approaches and molecular modeling (FIGS. 2A-P; FIGS. 11A-11K, FIGS. 15A-D). As a result of these studies, the inventors have identified a novel binding mechanism that governs the specificity with which epsin UIM interacts with activated VEGFR2. The resulting interaction competitively prohibits epsin binding to VEGFR2 and subsequent epsin-mediated VEGFR2 internalization and downregulation (FIG. 4K). Residues facilitating this interaction are unique to epsin UIM and drive the specificity with which UPI peptide targets VEGFR2, but not other angiogenic receptors.

UPI peptide disrupts the tightly regulated balance of VEGFR2 signaling, resulting in aberrant tumor angiogenesis and formation of dysfunctional tumor vasculature (FIG. 4K). Moreover, UPI peptide was equally as effective in inhibiting tumor growth as currently available anti-VEGF therapies (FIG. 4F). Although counter-intuitive and opposing in function to other anti-angiogenic approaches, these findings using the UPI peptide strongly suggest that the anti-tumorigenic effect of dysfunctional angiogenesis is a result of altered VEGFR2 signaling balance and can be achieved by either inhibiting or facilitating signaling. Collectively, the inventors' originally designed localized tumor-targeting approach has yielded a UPI peptide that holds uniquely high anti-angiogenic and anti-metastatic potential for cancer treatment (Burgess, 2013 and Klauber-Demore, 2012).

Example 2—Atherosclerosis

A. Materials and Methods

Tamoxifen-inducible Cre-driven global (iDKO) and constitutive Ve-cadherin Cre-driven endothelial-cell specific (EC-DKO) epsin 1 and 2 double knockout mice in ApoE$^{-/-}$ genetic background were established and fed western diet (WD) for ten weeks. Aortic lesions were analyzed by histology and oil red O staining. Expression of selectins, adhesion molecules and chemoattractants were analyzed by western blot or real time PCR (RT-PCR). Molecular mechanism was identified by molecular/cellular, biochemical, and genetic approaches.

B. Results

Histological analysis revealed that global epsin deletion in ApoE$^{-/-}$ mice significantly reduced atherosclerotic lesion area in aortic arch compared to control ApoE$^{-/-}$ mice. Similar results were obtained in aortic root by oil red O staining. Similarly, EC-iDKO in ApoE$^{-/-}$ mice presented reduced atherosclerotic lesion in aortic arch and root (FIGS. 19A-C). Accordingly, macrophage infiltration is also reduced in epsin-deficient mice (FIG. 19D). In aortic arch, immune cell infiltration is significantly attenuated (FIGS. 19E-F). Functional analysis revealed that endothelium-dependent aortic relaxation is greatly improved in EC-DKO/ApoE$^{-/-}$ mice (FIG. 19G). However, deletion of epsins in endothelium has no effect on the metabolism of glucose and lipid profile (FIG. 19H).

Epsins are upregulated in primary mouse aortic endothelial cell (EC) (MAEC) treated by oxLDL (FIG. 20A) and human atherosclerosis patients (FIG. 20B), suggesting epsins may promote atherosclerosis. ER stress markers are all downregulated in epsin-deficient mice (FIGS. 20C-D), indicating epsins modulate ER homeostasis and inflammation, these results were further confirmed in MAEC (FIG. 20E).

To further investigate the mechanism, MAEC were treated by oxLDL and immunoprecipitate with epsin1 antibody, followed by mass spectrometry analysis. The inventors identified that IP3R1, cytoskeletal proteins, stress response proteins and endocytosis proteins bind epsin1 (FIG. 21A). Atherosclerosis-prone substances or mediators oxLDL, cholesterol and 7KC significantly downregulated IP3R1 in WT MAECs, however it is stabilized in epsin-deficient cells (FIG. 21B) in a protesome-dependent fashion (FIG. 21C), these results were further confirmed in ApoE$^{-/-}$ and EC-DKO-ApoE$^{-/-}$ mice (FIG. 21D) and MAEC treated by 7KC. Furthermore, IP3R1 is downregulated in atherosclerosis patients (FIG. 21F).

Downregulating expression of IP3R1 augmented ER stress (FIG. 22A) and inflammation (FIG. 22C). Inhibition of IP3R1-promoted ER stress by 4-PBA inhibits ER stress and inflammation (FIGS. 22B and 22D), suggesting that ER stress promotes inflammation.

To link inflammation and atherosclerosis, the inventors measured the inflammatory readouts adhesion molecules and selections. In MAEC culture, deletion of epsins greatly reduced expression of P-selectin and adhesion molecules, ICAM1 and VCAM1. Furthermore, TNFα and LPS-induced upregulation of P- and E-selectins, ICAM1 and VCAM1 were remarkably attenuated by loss of epsins (FIG. 23A), reflected by impaired binding of WT macrophage on epsin deleted ECs (FIG. 23B). Macrophage chemoattractant, MCP-1, was also downregulated in epsin deleted MAEC compared to WT, consistent with impaired macrophage infiltration of the atheroma in EC-iDKO/ApoE$^{-/-}$ mice analyzed by Moma-2 immunofluorescent staining (FIG. 22C). TNFα, LPS or ox-LDL stimulated P-NFkb, P-JNK and P-p38 signaling is drastically attenuated, responsible for the reduction in leukocyte-endothelial interaction. Inflammation markers INF-γ (FIG. 23D) and TNF, IL-6 in serum is also reduced in epsin-deficient mice (FIG. 23E).

Furthermore, epsins bound to and facilitated proteasomal degradation of IP3R1 in endothelium under pro-inflammatory conditions (FIGS. 24A-C). Deletion of UIM in epsin1 greatly attenuated Epsin1-IP3R1 interaction (FIG. 24D), suggesting UIM is critical in facilitating the interaction and degradation (FIG. 24D). Truncation analysis of IP3R1 suggests that N-terminal of IP3R1 is the key for the interaction (FIG. 24E).

In preclinical mouse models, FITC-Lyp-UIM can be targeted into atheroma (FIG. 25A). In carotid atherosclerotic model, injection of Lyp-UIM peptide greatly reduced atherosclerosis lesion development when fed on a western diet (FIGS. 25B-C). In apoE$^{-/-}$ mouse model, injection of UIM peptide significantly inhibited lesion development in aortic roots and arches after 2 months on a western diet (FIGS. 25D-E).

TABLE 6

| Epsin 1 Binding Protein Under Inflammation Identified Mass Spectrometry | | |
|---|---|---|
| Category of putative Epsin1 binding proteins in Mass spec data | Putative Epsin1 binding proteins | Remarks |
| (1) Cytoskeletal or associated proteins | Filamin-C, A, SPTAN-1, 2, FN1, SVIL, Myosin-9, IQGAP-1, ACTN-4, ACTN-1, ACTB, ARPC1B, Drebrin, IVL, phostensin, GRN, ELM3, KRT77, ZYX, KRT6C, KRT74, KRT4, VIM, CRNN, KRT13, TUBA1A, KRT18, ACTB, ACTR2, ARPC18, TMOD3, CAV-1, CFL1, MYL6, PFN1, LGALS7, DCD, CSTB, STATH, 14-3-3 zeta/delta, GAPDH, RIP-A1 | IQGAP-1 binds actin is known in inflammation Vim binds actin is known |
| (2) Stress response related protein | GRP78, HSP90, HSP70, HSP78, EEF2, HSPB1, XRCC6, XRCC5 | GRP78 interaction with TRIM21/Ro52 is known |
| (3) Histones and Inflammatory mediators | Histone H3.1t, Histone H2A, H2B, Histone H4, ILF3 | |
| (4) Receptor, nuclear receptor binding protein and E3 ligase | ITPR1 (IP3R1), NRBP1 and TRIM21/Ro52 | IP3R1 binds GRP78 is known |
| (5) Endocytosis and protein trafficking | Clathrin1, Epsin1, Epsin2, ARF4, COPA, ANXA1 | Authentication of IP result |

TABLE 6-continued

Epsin 1 Binding Protein Under Inflammation Identified Mass Spectrometry

| Category of putative Epsin1 binding proteins in Mass spec data | Putative Epsin1 binding proteins | Remarks |
| --- | --- | --- |
| (6) Gene expression and translation | 1. Transcriptional factors: SMARCH4, CPSF6<br>2. RNA helicases: DHX9, DDX21, DDX3X, DDX5, DDX1;<br>3. RNA binding and processing proteins: RBM33, FUS;<br>4. Ribosomal proteins: total 32<br>5. Elongation factor: EEF1A1, EEF1D, EEF2. | |

Example 3—Obesity

Generation of Tamoxifen-Inducible Global Epsin DKO (iDKO) Mice.

Global deficiency of epsins 1 and 2 (DKO) causes embryonic lethality (Chen et al., 2009). To study epsin function in specific cell types and to circumvent lethality, the inventors generated mice in a C57BL/6 background with epsin 1 flanked by loxP sites (epsin 1f/f) on a global epsin 2-deficient background (epsin 1f/f epsin 2−/−). iDKO mice were created by crossing epsin 1f/f epsin 2−/− mice with Cre-ERT2 deleter mice that express Cre recombinase in all cells upon tamoxifen injection (Hayashi & McMahon, 2002). Control wild-type (WT) mice are defined as epsin 1f/f epsin 2+/+, Cre-ERT2-negative or epsin 1+/+, epsin 2+/+, Cre-ERT2-positive (with or without tamoxifen injection). After tamoxifen administration for ~10 days, the inventors examined epsin 1 expression in majority variety of tissues or organs. Results suggest that epsin 1 expression in major insulin targeting tissues, adipose, skeletal muscle and liver, is decreased by 85%~95%.

Epsins-Deficient Mice are Significantly Resistant to Body Weight (BW) Gain.

Three month-old, gender-matched iDKO or WT female mice were fed HFD (Ouchi et al., 2010) as shown in FIGS. 26A-B. After 3-6 months of HFD feeding, WT mice exhibit significant increases in BW. In contrast, iDKO mice exhibit no obvious weight gain (FIGS. 26A-B) and are comparable to mice on normal chow diet (ND) (FIGS. 26A-B); a similar result was obtained in male mice (data not shown). Taken together, mice deficient of epsins are resistant to HFD-induced BW gain, suggesting that epsins play a critical role in body weight control.

Epsins-Deficient Mice Fed HFD have Reduced Adiposity.

Five male and female WT and iDKO mice fed HFD for 17 weeks were used to perform DEXA scan. Male iDKO mice gain much less fat mass (3.975 g, or 14.5% of BW) compared to WT (14.86 g, or 37.4% of BW). Epsin loss did not statistically affect lean mass (p=0.26), indicating that the differences in BW (WT-iDKO=12.7 g) are mainly from changes in fat mass (WT-iDKO=10.89 g). Similar results were obtained in the female mice. These findings strongly suggest changes in fat mass are the main contributor (~89%) responsible for BW differences between WT and iDKO mice. Epsin loss did not affect body length or organ and tissue weight in a 3-month HFD feeding (liver, lung, skeletal muscle, bone, etc.) (data not shown). Single epsin 2 KO has neglected effect on BW and fat pads of mice fed by HFD or normal chow diet. Taken together, absence of epsins protects against HFD-induced obesity as a result of impaired adiposity. Adipogenic gene expression (PPAR-gamma, CEBPα/β, and aP2) is all downregulated in adipose tissues revealed by qPCR (data not shown).

Obesity is Positively Correlated with Higher Expression of Epsins.

The inventors compared epsin expression in leptin-deficient mice (ob/ob) and lean mice fed on normal chow diet. As shown in FIGS. 27A-C, epsin expression in ob/ob or HFD-induced obese mice is significantly upregulated in adipose tissues, a finding further confirmed by immunofluorescent staining (FIGS. 27A-C). This result can be phenocopied in mice fed by HFD (FIGS. 27A-C).

Loss of Epsins Significantly Reduces Circulating Insulin Levels.

The inventors measured the circulating insulin levels of WT and iDKO male (M) and female (F) mice fed HFD. iDKO mice exhibit significant reductions in circulating insulin levels (0.2-0.3 ng/ml in male, 0.7-0.9 ng/ml in female), compared to WT male and female mice (both around 1.8-3.5 ng/ml).

Epsins Regulate Lipid Metabolism.

Figure 28D:
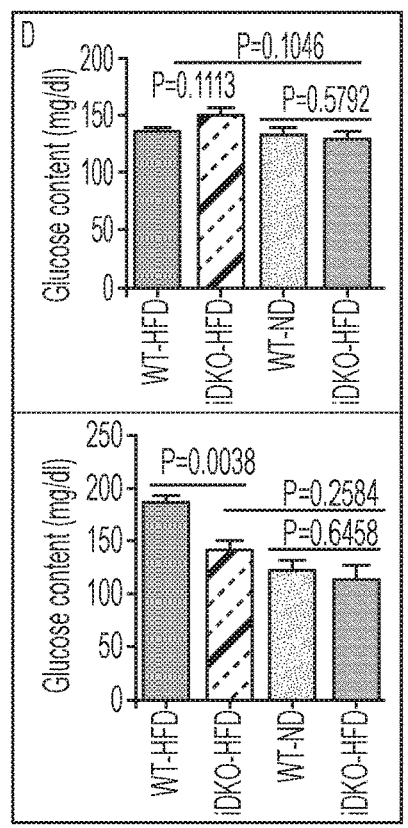

The inventors identified that epsin loss significantly reduced the size of adipocytes (FIG. 28A). H&E (data not shown) and Oil Red O staining uncovered that lipid metabolism is greatly improved in liver (FIG. 28B-top), a finding confirmed by total triglyceride (TG) analysis in liver (FIG. 28B-bottom). Insulin tolerance test (ITT) and glucose tolerance test (GTT) were performed (Ouchi et al., 2010; Ma et al., 2002; Erickson et al., 1996; Hotamisligil et al., 1996; Yuan et al., 2001; Elchebly et al., 1999; Ozcan et al., 2004; Copps et al., 2010 and Saberi et al., 2009) in WT and iDKO mice fed either HFD or ND. Compared to WT mice, insulin signaling is sustained in iDKO mice fed HFD; similarly, glucose clearance in blood is greater in iDKO mice fed HFD (FIG. 28C). Furthermore, after 16-hr fasting, basal glucose levels in iDKO mice fed HFD were lower than WT on HFD, but no difference was observed between iDKO and WT fed ND (FIG. 28D-bottom). Collectively, these data suggest that epsin depletion enhances insulin sensitivity, despite the fact that basal glucose levels were not different in non-fasted WT and iDKO mice (FIG. 28D-top).

Epsins Bind IRS1 Complex in 3T3-L1 Preadipocyte Cells.

In 3T3-L1 cells, insulin induces the interaction of epsin 1 with IRS1/IR/IGF-1R in IP analysis (FIG. 29).

Downregulation of Epsin Expression in 3T3-L1 Cell Line Impairs Adipocyte Differentiation.

The inventors utilized epsins 1 and 2 shRNA expressing lentivirus to downregulate epsin expression in 3T3 L1 cell line. As shown in FIG. 30, reduced epsin expression attenuated 3T3-L1 differentiation.

Specific Deletion of Epsins in Adipocytes Diminishes Fat Pad Development.

The inventors recently generated adipocyte-specific epsin-deficient mice using aP2-cre transgenic mice. The results suggest that epsin loss in adipocytes significantly reduces HFD-induced BW and fat pads (FIGS. 31A-C); a similar finding to the results obtained from the iDKO mice (FIGS. 26A-B).

Loss of Epsins in Fat Tissues Attenuated Phosphor-AKT and Phosphor-mTOR Signaling.

As shown in FIGS. 32A-B, insulin activated P-AKT and P-mTOR signaling are significantly inhibited in fat pads in the absence of epsins.

Loss of Epsins do not Change Food Intake, RER and Mitochondrial Biogenesis.

Relative food intake-to-body weight was not changed in epsin-deficient mice versus WT (data not shown). The inventors measured RER (Respiratory Exchange Ratio) by flow calorimetry system, and no differences have been found between control and iDKO mice. Further, mitochondrial biogenesis in major metabolic tissues (skeletal muscle, liver and fat pads) exhibited no difference by analyzing PHB1 (prohinitin 1), PGC1α and cytochrome-c expression. This finding was confirmed by mitotracker staining (data not shown). UCP1 expression in WAT and BAT remains consistent between WT and iDKO mice.

Loss of Epsins Significantly Changed Lipid Profile in Plasma of Mice Fed HFD.

Loss of epsins significantly reduced cholesterol (900-1100 mg/dl in Control versus 500-700 mg/dl in iDKO; P<0.05) and LDL/VLDL (320-380 mg/dl in Control versus 180-220 mg/dl in iDKO; P<0.05), suggesting that epsins impact lipid metabolism.

Therapeutic Activity of Epsin UIM Peptide.

The inventors have tested a UIM peptide (AP-UIM) in HFD-induced obesity model. UIM peptide administration by i.p significantly attenuated body weight gain when mice were fed HFD (FIGS. 33A-C), strongly suggesting that administration of epsin UIM peptide could have a significant effect in combating obesity.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

4. REFERENCES

The following references, to the extent that they provide exemplary procedural or other details supplementary to those set forth herein, are specifically incorporated herein by reference.

Barany & Merrifield, In: *The Peptides*, Gross and Meienhofer (Eds.), Academic Press, NY, 1-284, 1979.
Bergers & Hanahan, *Nature Reviews Cancer* 8, 592, 2008.
Bogdanowich-Knipp et al., *The Journal of Peptide Research: Official Journal of the American Peptide Society* 53, 530, 1999.
Brower, *Nature Biotechnology* 17, 963, 1999.
Burgess, *Nature Reviews Cancer* 13, 4, 2013.
Cai et al., *Biomaterials* 33, 8771, 2012.
Cao et al., *Brain Res.*, 644:267-272, 1994.
Capaldi et al., *Biochem. Biophys. Res. Comm.*, 74(2):425-433, 1977.
Carmeliet & Jain, *Nature*, 473:298, 2011.
Carmeliet, *Nat. Med.*, 9(6):653-660, 2003.
Carney et al., *Proc. Natl. Acad. Sci. USA*, 88:3633-3636, 1991.
Chen & De Camilli, *Proc. Natl. Acad. Sci. USA*, 102(8): 2766-2771. 2005.
Chen et al., *Nature*, 394(6695):793-797, 1998.
Chen et al., *Proc. Natl. Acad. Sci. USA*, 106(33):13838-13843, 2009.
Clough-Helfman et al., *Free Radic. Res. Commun.*, 15:177-186, 1991.
Comeau et al., *Bioinformatics* 20, 45, 2004.
Coon et al., *Commun Integr. Biol.* 4, 95, 2011.
Copps et al., *Cell Metab.* 11, 84-92, 2010.
De Visser et al., *Nature Reviews Cancer* 6, 24, 2006.
Dikic & Schmidt, *Bioessays* 32, 481, 2010.
Doblas et al., *NMR Biomed* 25, 685, 2012.
Dvorak, *J Clin Oncol* 20, 4368, 2002.
Elchebly et al., *Science* 283:1544-1548, 1999.
Erickson et al., *Science* 274:1704-1707, 1996.
Ferrara & Kerbel, *Nature*, 438:967, 2005.
Ferrara et al., *Biochem Biophys Res Commun* 333:328, 2005.
Ferrara et al., *Nat Rev Drug Discov* 3, 391, 2004.
Floyd et al., *Biochem. Biophys. Res. Commun.*, 74:79-84, 1977.
Floyd et al., *FASEB J.*, 4:2587-2597, 1990.
Floyd et al., In: *Neuroprotective Approaches to the Treatment of Parkinson's Disease and other Neurodegenerative Disorders*, Chapman et al. (Eds.), Academic Press Limited, London, 69-90, 1996.
Floyd, *Adv. Pharmacol.*, 38:361-378, 1997.
Folbergrova et al., *Proc. Natl. Acad. Sci. USA*, 92:5057-5061, 1995.
Folkman, *The New England journal of medicine*, 285:1182, 1971.
Gaur et al., *Seminars in oncology* 36, S12, 2009.
Greenberg et al., *Proceedings of the National Academy of Sciences of the United States of America* 92, 3439, 1995.
Hayashi & McMahon, *Dev. Biol.* 244:305-318, 2002.
He et al., *Am J Nucl Med Mol Imaging* 3, 300, 2013.
Hensley et al., In: *Neuroprotective Agents and Cerebral Ischaemia*, Green and Cross (Eds.), Academic press Ltd., London, 299-317, 1996.
Hotamisligil et al., *Science* 274, 1377-1379, 1996.
J. Plescia et al., *Cancer Cell* 7, 457, 2005.
Jain et al., *Nat Clin Pract Oncol* 3, 24, 2006.
Janzen, *Acc. Chem. Res.*, 4:31-40, 1971.
Joliot & Prochiantz, *Nature Cell Biology* 6, 189, 2004.
Jubb et al., *Nature Reviews Cancer* 6, 626, 2006.
Kerbel, *N Engl J Med*, 358:2039, 2008.
Kim et al., *Nature* 362:841, 1993.
Klauber-Demore, *The Journal of Clinical Investigation* 122, 4341, 2012.
Kovarova et al., *Mol Cell Biol.* 21, 8318, 2001.
Leppanen et al., *Proceedings of the National Academy of Sciences of the United States of America* 107, 2425, 2010.
Liu et al., *Journal of Cell Science* 122, 3294, 2009.
Ma et al., *J Biol. Chem.* 277:34658-34661, 2002.
Maupetit et al., *Nucleic Acids Res* 37, W498, 2009.
McTigue et al., *Proceedings of the National Academy of Sciences of the United States of America* 109, 18281, 2012.
Merrifield, *Science*, 232(4748):341-347 1986.
Messa et al., *Elife*, e03311, 2014.

Nakayama et al., *Nature Cell Biology* 15, 249, 2013.
Noguera-Troise et al., *Nature,* 444(7122):1032-1037, 2006.
Novelli et al., In: *Oxygen Free Radicals in Shock*, Novelli and Ursini (Eds.), Karger, Basel, 119-124, 1986.
Ouchi et al., Science 329:454-457, 2010.
Ozcan et al., Science 306:457-461, 2004.
Pahlmark et al., *Acta Physiol. Scand.,* 157:41-51, 1996.
Pasula et al., *The Journal of Clinical Investigation* 122, 4424, 2012.
Pogrebniak et al., *Surgery,* 112:130-139, 1992.
Poyer et al., *Biochim. Biophys. Acta,* 539:402-409, 1978.
Presta et al., *Cancer research* 57, 4593, 1997.
Ridgway et al., *Nature,* 444(7122):1083-1087, 2006.
Rosenthal et al., *J. Biol. Chem.,* 274(48):33959-33965, 1999.
Saaristo et al., *Oncogene* 19, 6122, 2000.
Saberi et al., Cell Metab. 10, 419-429, 2009.
Saharinen et al., *Trends Mol. Med.* 17, 347, 2011.
Stewart & Young, In: *Solid Phase Peptide Synthesis,* 2$^{nd}$ Ed., Pierce Chemical Co., 1984.
Sugahara et al., *Cancer Cell* 16, 510, 2009.
Sugahara et al., *Science* 328, 1031, 2010.
Swanson et al., *The EMBO Journal* 22, 4597, 2003.
Tam et al., *J. Am. Chem. Soc.,* 105:6442, 1983.
Tessneer et al., *Arteriosclerosis, Thrombosis, and Vascular Biology* 34, 331, 2014.
Tessneer et al., *ISRN Oncology* 2013, 8, 2013.
Tessneer et al., *J Can Res Updates* 2, 144, 2013.
Thevenet et al., *Nucleic Acids Res* 40, W288, July
Valapala et al., *Journal of Cell Science* 124, 1453, 2011.
Weis & Cheresh, *Nature medicine,* 17:1359, 2011.
Yancopoulos et al., *Nature* 407, 242, 2000.
Yuan et al., *Science* 293:1673-1677, 2001.
Zetter, *Annual Review of Medicine* 49, 407, 1998.
Ziyad & Iruela-Arispe, *Genes Cancer* 2, 1085, 2011.
U.S. Pat. No. 5,488,145
U.S. Pat. No. 5,569,902
U.S. Patent Publication 2007/0032453

What is claimed is:

1. A method of reducing the risk of myocardial infarction in a subject, treating heart disease in a subject, reducing an atherosclerotic plaque rupture in a subject, reducing the risk of restenosis in a subject, inhibiting atherosclerosis in a subject, reducing vascular inflammation in a subject, or reducing weight in a subject comprising administering to said subject a peptide comprising a ubiquitin interactive motif (UIM)-containing peptide comprising the sequence CKGGRAKDCSGEEELQLQLALAMSKEE (SEQ ID NO: 6).

2. The method of claim 1, wherein the subject has or is at risk of myocardial infarction, heart disease, atherosclerotic plaque rupture, restenosis, atherosclerosis, or vascular inflammation.

3. The method of claim 1, wherein the UIM-containing peptide is about 27 to about 50 residues in length.

4. The method of claim 2, wherein the subject exhibits one or more symptoms of heart disease selected from decreased exercise capacity, decreased blood ejection volume, increased left ventricular end diastolic pressure, increased pulmonary capillary wedge pressure, decreased cardiac output, pathologic cardiac index, increased pulmonary artery pressures, increased left ventricular end systolic and diastolic dimensions, increased left and right ventricular wall stress, or wall tension, decreased quality of life, or increased disease-related morbidity and mortality.

5. The method of claim 2, further comprising administering to the subject a second anti-atherosclerosis therapy.

6. The method of claim 5, wherein the second-atherosclerosis therapy is a statin.

7. The method of claim 1, wherein the subject has excess body fat or is overweight.

8. The method of claim 7, wherein the subject has class I, class II, or class III obesity.

9. The method of claim 1, wherein the UIM-containing peptide consists of the sequence CKGGRAKDCSGEEELQLQLLALAMSKEE (SEQ ID NO:6).

10. The method of claim 7, wherein the UIM-containing peptide is 27 to about 50 residues in length.

11. The method of claim 7, wherein the subject also suffers from renal disease, cardiovascular disease, diabetes, autoimmune disease, respiratory disease, neurodegenerative disease, liver disease, infectious disease, cancer, or has or will undergo transplant.

12. The method of claim 1, wherein the subject is a human subject.

13. The method of claim 1, wherein the administration is intravenous, intra-arterial, intra-nasal, transdermal, or oral.

14. The method of claim 1, wherein the administration is daily, every other day, weekly, or monthly.

\* \* \* \* \*

UNITED STATES PATENT AND TRADEMARK OFFICE
CERTIFICATE OF CORRECTION

| | |
|---|---|
| PATENT NO. | : 11,084,852 B2 |
| APPLICATION NO. | : 15/736022 |
| DATED | : August 10, 2021 |
| INVENTOR(S) | : Yunzhou Dong et al. |

It is certified that error appears in the above-identified patent and that said Letters Patent is hereby corrected as shown below:

In the Specification

At Column 1, Line 16, please add the following new paragraph before the "BACKGROUND" paragraph:
FEDERALLY SPONSORED RESEARCH
This invention was made with government support under Grant Numbers HL093242 and HL118676, awarded by the National Institutes of Health. The Government has certain rights in the invention.

Signed and Sealed this
Fifth Day of December, 2023

Katherine Kelly Vidal
*Director of the United States Patent and Trademark Office*

SEQUENCE LISTING

```
<160> NUMBER OF SEQ ID NOS: 59

<210> SEQ ID NO 1
<211> LENGTH: 18
<212> TYPE: PRT
<213> ORGANISM: Artificial sequence
<220> FEATURE:
<223> OTHER INFORMATION: Synthetic peptide

<400> SEQUENCE: 1

Ser Gly Glu Glu Glu Leu Gln Leu Gln Leu Ala Leu Ala Met Ser Lys
1               5                   10                  15

Glu Glu

<210> SEQ ID NO 2
<211> LENGTH: 36
<212> TYPE: PRT
<213> ORGANISM: Artificial sequence
<220> FEATURE:
<223> OTHER INFORMATION: Synthetic peptide

<400> SEQUENCE: 2

Ser Gly Glu Glu Glu Leu Gln Leu Gln Leu Ala Leu Ala Met Ser Lys
1               5                   10                  15

Glu Glu Met Gly Cys Ile Lys Ser Lys Arg Lys Cys Arg Gly Asp Lys
            20                  25                  30

Gly Pro Asp Cys
        35

<210> SEQ ID NO 3
<211> LENGTH: 9
<212> TYPE: PRT
<213> ORGANISM: Artificial sequence
<220> FEATURE:
<223> OTHER INFORMATION: Synthetic peptide

<400> SEQUENCE: 3

Cys Arg Gly Asp Lys Gly Pro Asp Cys
1               5

<210> SEQ ID NO 4
<211> LENGTH: 9
<212> TYPE: PRT
<213> ORGANISM: Artificial sequence
```

```
<220> FEATURE:
<223> OTHER INFORMATION: Synthetic peptide

<400> SEQUENCE: 4

Met Gly Cys Ile Lys Ser Lys Arg Lys
1               5

<210> SEQ ID NO 5
<211> LENGTH: 27
<212> TYPE: PRT
<213> ORGANISM: Artificial sequence
<220> FEATURE:
<223> OTHER INFORMATION: Synthetic peptide

<400> SEQUENCE: 5

Cys Gly Asn Lys Arg Thr Arg Gly Cys Ser Gly Glu Glu Glu Leu Gln
1               5                   10                  15

Leu Gln Leu Ala Leu Ala Met Ser Lys Glu Glu
            20                  25

<210> SEQ ID NO 6
<211> LENGTH: 27
<212> TYPE: PRT
<213> ORGANISM: Artificial sequence
<220> FEATURE:
<223> OTHER INFORMATION: Synthetic peptide

<400> SEQUENCE: 6

Cys Lys Gly Gly Arg Ala Lys Asp Cys Ser Gly Glu Glu Glu Leu Gln
1               5                   10                  15

Leu Gln Leu Ala Leu Ala Met Ser Lys Glu Glu
            20                  25

<210> SEQ ID NO 7
<211> LENGTH: 27
<212> TYPE: PRT
<213> ORGANISM: Artificial sequence
<220> FEATURE:
<223> OTHER INFORMATION: Synthetic peptide

<400> SEQUENCE: 7

Ser Gly Glu Glu Glu Leu Gln Leu Gln Leu Ala Leu Ala Met Ser Lys
1               5                   10                  15

Glu Glu Met Gly Cys Ile Lys Ser Lys Arg Lys
            20                  25

<210> SEQ ID NO 8
<211> LENGTH: 9
<212> TYPE: PRT
<213> ORGANISM: Artificial sequence
<220> FEATURE:
<223> OTHER INFORMATION: Synthetic peptide

<400> SEQUENCE: 8

Cys Gly Asn Lys Arg Thr Arg Gly Cys
1               5

<210> SEQ ID NO 9
<211> LENGTH: 9
<212> TYPE: PRT
<213> ORGANISM: Artificial sequence
<220> FEATURE:
<223> OTHER INFORMATION: Synthetic peptide

<400> SEQUENCE: 9
```

```
Cys Lys Gly Gly Arg Ala Lys Asp Cys
1               5
```

<210> SEQ ID NO 10
<211> LENGTH: 5
<212> TYPE: PRT
<213> ORGANISM: Artificial sequence
<220> FEATURE:
<223> OTHER INFORMATION: Synthetic peptide

<400> SEQUENCE: 10

```
Leu Ala Leu Ala Leu
1               5
```

<210> SEQ ID NO 11
<211> LENGTH: 16
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feat
<222> LOCATION: (2)..(5)
<223> OTHER INFORMATION: Xaa = Glu or Asp
<220> FEATURE:
<221> NAME/KEY: misc_feat
<222> LOCATION: (6)..(6)
<223> OTHER INFORMATION: Xaa = large hydrophobic residue, typically Leu
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (10)..(12)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: misc_feat
<222> LOCATION: (16)..(16)
<223> OTHER INFORMATION: Xaa = Glu or Asp

<400> SEQUENCE: 11

```
Xaa Xaa Xaa Xaa Xaa Xaa Xaa Xaa Ala Xaa Xaa Xaa Ser Xaa Xaa Xaa
1               5                   10                  15
```

<210> SEQ ID NO 12
<211> LENGTH: 16
<212> TYPE: PRT
<213> ORGANISM: Artificial sequence
<220> FEATURE:
<223> OTHER INFORMATION: Synthetic peptide

<400> SEQUENCE: 12

```
Arg Gln Ile Lys Ile Trp Phe Gln Asn Arg Arg Met Lys Trp Lys Lys
1               5                   10                  15
```

<210> SEQ ID NO 13
<211> LENGTH: 13
<212> TYPE: PRT
<213> ORGANISM: Artificial sequence
<220> FEATURE:
<223> OTHER INFORMATION: Synthetic peptide

<400> SEQUENCE: 13

```
Gly Arg Lys Lys Arg Gln Arg Arg Pro Pro Gln
1               5                   10
```

<210> SEQ ID NO 14
<211> LENGTH: 18
<212> TYPE: PRT
<213> ORGANISM: Artificial sequence
<220> FEATURE:
<223> OTHER INFORMATION: Synthetic peptide

<400> SEQUENCE: 14

```
Leu Leu Ile Ile Leu Arg Arg Arg Ile Arg Lys Gln Ala His Ala His
1               5                   10                  15

Ser Lys
```

<210> SEQ ID NO 15
<211> LENGTH: 27
<212> TYPE: PRT
<213> ORGANISM: Artificial sequence
<220> FEATURE:
<223> OTHER INFORMATION: Synthetic peptide

<400> SEQUENCE: 15

```
Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25
```

<210> SEQ ID NO 16
<211> LENGTH: 27
<212> TYPE: PRT
<213> ORGANISM: Artificial sequence
<220> FEATURE:
<223> OTHER INFORMATION: Synthetic peptide

<400> SEQUENCE: 16

```
Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25
```

<210> SEQ ID NO 17
<211> LENGTH: 21
<212> TYPE: PRT
<213> ORGANISM: Artificial sequence
<220> FEATURE:
<223> OTHER INFORMATION: Synthetic peptide

<400> SEQUENCE: 17

```
Lys Glu Thr Trp Trp Glu Thr Trp Trp Thr Glu Trp Ser Gln Pro Lys
1               5                   10                  15

Lys Lys Arg Lys Val
            20
```

<210> SEQ ID NO 18
<211> LENGTH: 18
<212> TYPE: PRT
<213> ORGANISM: Artificial sequence
<220> FEATURE:
<223> OTHER INFORMATION: Synthetic peptide

<400> SEQUENCE: 18

```
Lys Leu Ala Leu Lys Leu Ala Leu Lys Ala Leu Lys Ala Ala Leu Lys
1               5                   10                  15
```

Leu Ala

<210> SEQ ID NO 19
<211> LENGTH: 9
<212> TYPE: PRT
<213> ORGANISM: Artificial sequence
<220> FEATURE:
<223> OTHER INFORMATION: Synthetic peptide

<400> SEQUENCE: 19

Arg Arg Trp Trp Arg Arg Trp Arg Arg
1               5

<210> SEQ ID NO 20
<211> LENGTH: 12
<212> TYPE: PRT
<213> ORGANISM: Artificial sequence
<220> FEATURE:
<223> OTHER INFORMATION: Synthetic peptide

<400> SEQUENCE: 20

Phe Cys Asp Gly Phe Tyr Ala Cys Tyr Lys Asp Val
1               5                   10

<210> SEQ ID NO 21
<211> LENGTH: 21
<212> TYPE: PRT
<213> ORGANISM: Artificial sequence
<220> FEATURE:
<223> OTHER INFORMATION: Synthetic peptide

<400> SEQUENCE: 21

Leu Gly Ala Ser Trp His Arg Pro Asp Lys Cys Cys Leu Gly Tyr Gln
1               5                   10                  15

Lys Arg Pro Leu Pro
            20

<210> SEQ ID NO 22
<211> LENGTH: 10
<212> TYPE: PRT
<213> ORGANISM: Artificial sequence
<220> FEATURE:
<223> OTHER INFORMATION: Synthetic peptide

<400> SEQUENCE: 22

Leu Gly Ala Ser Trp His Arg Pro Asp Lys
1               5                   10

<210> SEQ ID NO 23
<211> LENGTH: 9
<212> TYPE: PRT
<213> ORGANISM: Artificial sequence
<220> FEATURE:
<223> OTHER INFORMATION: Synthetic peptide

<400> SEQUENCE: 23

Cys Pro Gly Pro Glu Gly Ala Gly Cys
1               5

<210> SEQ ID NO 24
<211> LENGTH: 5
<212> TYPE: PRT
<213> ORGANISM: Artificial sequence
<220> FEATURE:
<223> OTHER INFORMATION: Synthetic peptide

```
<400> SEQUENCE: 24

Cys Arg Glu Lys Ala
1               5

<210> SEQ ID NO 25
<211> LENGTH: 9
<212> TYPE: PRT
<213> ORGANISM: Artificial sequence
<220> FEATURE:
<223> OTHER INFORMATION: Synthetic peptide

<400> SEQUENCE: 25

Cys Thr Pro Ser Pro Phe Ser His Cys
1               5

<210> SEQ ID NO 26
<211> LENGTH: 12
<212> TYPE: PRT
<213> ORGANISM: Artificial sequence
<220> FEATURE:
<223> OTHER INFORMATION: Synthetic peptide

<400> SEQUENCE: 26

Ser Phe His Gln Phe Ala Arg Ala Thr Leu Ala Ser
1               5                   10

<210> SEQ ID NO 27
<211> LENGTH: 11
<212> TYPE: PRT
<213> ORGANISM: Artificial sequence
<220> FEATURE:
<223> OTHER INFORMATION: Synthetic peptide

<400> SEQUENCE: 27

His Ile Gln Leu Ser Pro Phe Gln Ser Trp Arg
1               5                   10

<210> SEQ ID NO 28
<211> LENGTH: 4
<212> TYPE: PRT
<213> ORGANISM: Artificial sequence
<220> FEATURE:
<223> OTHER INFORMATION: Synthetic peptide

<400> SEQUENCE: 28

Leu Lys Lys Pro
1

<210> SEQ ID NO 29
<211> LENGTH: 4
<212> TYPE: PRT
<213> ORGANISM: Artificial sequence
<220> FEATURE:
<223> OTHER INFORMATION: Synthetic peptide

<400> SEQUENCE: 29

Glu Pro Lys Lys
1

<210> SEQ ID NO 30
<211> LENGTH: 4
<212> TYPE: PRT
<213> ORGANISM: Artificial sequence
<220> FEATURE:
<223> OTHER INFORMATION: Synthetic peptide

<400> SEQUENCE: 30
```

Glu Leu Lys Lys
1

<210> SEQ ID NO 31
<211> LENGTH: 4
<212> TYPE: PRT
<213> ORGANISM: Artificial sequence
<220> FEATURE:
<223> OTHER INFORMATION: Synthetic peptide

<400> SEQUENCE: 31

Pro Tyr Glu Glu
1

<210> SEQ ID NO 32
<211> LENGTH: 7
<212> TYPE: PRT
<213> ORGANISM: Artificial sequence
<220> FEATURE:
<223> OTHER INFORMATION: Synthetic peptide

<400> SEQUENCE: 32

Pro Phe Ser Ser Thr Lys Thr
1               5

<210> SEQ ID NO 33
<211> LENGTH: 13
<212> TYPE: PRT
<213> ORGANISM: Artificial sequence
<220> FEATURE:
<223> OTHER INFORMATION: Synthetic peptide

<400> SEQUENCE: 33

Cys Thr Val Ala Leu Pro Gly Gly Tyr Val Arg Val Cys
1               5                   10

<210> SEQ ID NO 34
<211> LENGTH: 12
<212> TYPE: PRT
<213> ORGANISM: Artificial sequence
<220> FEATURE:
<223> OTHER INFORMATION: Synthetic peptide

<400> SEQUENCE: 34

Asp Trp Arg Val Ile Ile Pro Pro Arg Pro Ser Ala
1               5                   10

<210> SEQ ID NO 35
<211> LENGTH: 9
<212> TYPE: PRT
<213> ORGANISM: Artificial sequence
<220> FEATURE:
<223> OTHER INFORMATION: Synthetic peptide

<400> SEQUENCE: 35

Cys Asp Cys Arg Gly Asp Cys Phe Cys
1               5

<210> SEQ ID NO 36
<211> LENGTH: 11
<212> TYPE: PRT
<213> ORGANISM: Artificial sequence
<220> FEATURE:
<223> OTHER INFORMATION: Synthetic peptide

<400> SEQUENCE: 36

```
Cys Arg Gly Asp Lys Arg Gly Pro Asp Glu Cys
1               5                   10

<210> SEQ ID NO 37
<211> LENGTH: 20
<212> TYPE: PRT
<213> ORGANISM: Artificial sequence
<220> FEATURE:
<223> OTHER INFORMATION: Synthetic peptide

<400> SEQUENCE: 37

Gln Glu Glu Glu Glu Leu Gln Leu Ala Leu Ala Leu Ser Gln Ser Glu
1               5                   10                  15

Ala Glu Glu Lys
            20

<210> SEQ ID NO 38
<211> LENGTH: 20
<212> TYPE: PRT
<213> ORGANISM: Artificial sequence
<220> FEATURE:
<223> OTHER INFORMATION: Synthetic peptide

<400> SEQUENCE: 38

Ser Glu Glu Asp Met Ile Glu Trp Ala Lys Arg Glu Ser Glu Arg Glu
1               5                   10                  15

Glu Glu Gln Arg
            20

<210> SEQ ID NO 39
<211> LENGTH: 18
<212> TYPE: PRT
<213> ORGANISM: Artificial sequence
<220> FEATURE:
<223> OTHER INFORMATION: Synthetic peptide

<400> SEQUENCE: 39

Gln Ser Leu Gln Glu Ser Gly Met Glu Leu Glu Ala Glu Leu Ala Leu
1               5                   10                  15

Glu Lys

<210> SEQ ID NO 40
<211> LENGTH: 34
<212> TYPE: PRT
<213> ORGANISM: Artificial sequence
<220> FEATURE:
<223> OTHER INFORMATION: Synthetic peptide

<400> SEQUENCE: 40

Arg Gln Ile Lys Ile Trp Phe Gln Asn Arg Arg Met Lys Trp Lys Lys
1               5                   10                  15

Ser Gly Glu Glu Glu Leu Gln Leu Gln Leu Ala Leu Ala Met Ser Lys
            20                  25                  30

Glu Glu

<210> SEQ ID NO 41
<211> LENGTH: 27
<212> TYPE: PRT
<213> ORGANISM: Artificial sequence
<220> FEATURE:
<223> OTHER INFORMATION: Synthetic peptide

<400> SEQUENCE: 41

Ser Gly Glu Glu Glu Leu Gln Leu Gln Leu Ala Leu Ala Met Ser Lys
```

```
                1               5                   10                  15

Glu Glu Cys Arg Gly Asp Lys Gly Pro Asp Cys
            20                  25

<210> SEQ ID NO 42
<211> LENGTH: 36
<212> TYPE: PRT
<213> ORGANISM: Artificial sequence
<220> FEATURE:
<223> OTHER INFORMATION: Synthetic peptide

<400> SEQUENCE: 42

Ser Gly Glu Glu Glu Leu Gln Leu Gln Leu Ala Leu Ala Met Ser Lys
1               5                   10                  15

Glu Glu Met Gly Cys Ile Lys Ser Lys Arg Lys Cys Arg Gly Asp Lys
            20                  25                  30

Gly Pro Asp Cys
        35

<210> SEQ ID NO 43
<211> LENGTH: 36
<212> TYPE: PRT
<213> ORGANISM: Artificial sequence
<220> FEATURE:
<223> OTHER INFORMATION: Synthetic peptide

<400> SEQUENCE: 43

Ser Gly Glu Glu Glu Leu Gln Leu Ala Leu Ala Leu Ser Met Ser Ala
1               5                   10                  15

Glu Glu Met Gly Cys Ile Lys Ser Lys Arg Lys Cys Arg Gly Asp Lys
            20                  25                  30

Gly Pro Asp Cys
        35

<210> SEQ ID NO 44
<211> LENGTH: 38
<212> TYPE: PRT
<213> ORGANISM: Artificial sequence
<220> FEATURE:
<223> OTHER INFORMATION: Synthetic peptide

<400> SEQUENCE: 44

Gln Glu Glu Glu Glu Leu Gln Leu Ala Leu Ala Leu Ser Gln Ser Glu
1               5                   10                  15

Ala Glu Glu Lys Met Gly Cys Ile Lys Ser Lys Arg Lys Cys Arg Gly
            20                  25                  30

Asp Lys Gly Pro Asp Cys
        35

<210> SEQ ID NO 45
<211> LENGTH: 38
<212> TYPE: PRT
<213> ORGANISM: Artificial sequence
<220> FEATURE:
<223> OTHER INFORMATION: Synthetic peptide

<400> SEQUENCE: 45

Ser Glu Glu Asp Met Ile Glu Trp Ala Lys Arg Glu Ser Glu Arg Glu
1               5                   10                  15

Glu Glu Gln Arg Met Gly Cys Ile Lys Ser Lys Arg Lys Cys Arg Gly
            20                  25                  30

Asp Lys Gly Pro Asp Cys
```

<210> SEQ ID NO 46
<211> LENGTH: 36
<212> TYPE: PRT
<213> ORGANISM: Artificial sequence
<220> FEATURE:
<223> OTHER INFORMATION: Synthetic peptide

<400> SEQUENCE: 46

Gln Ser Leu Gln Glu Ser Gly Met Glu Leu Glu Ala Glu Leu Ala Leu
1               5                   10                  15
Glu Lys Met Gly Cys Ile Lys Ser Lys Arg Lys Cys Arg Gly Asp Lys
            20                  25                  30
Gly Pro Asp Cys
        35

<210> SEQ ID NO 47
<211> LENGTH: 34
<212> TYPE: PRT
<213> ORGANISM: Artificial sequence
<220> FEATURE:
<223> OTHER INFORMATION: Synthetic peptide

<400> SEQUENCE: 47

Arg Gln Ile Lys Ile Trp Phe Gln Asn Arg Arg Met Lys Trp Lys Lys
1               5                   10                  15
Gln Ser Leu Gln Glu Ser Gly Met Glu Leu Glu Ala Glu Leu Ala Leu
            20                  25                  30
Glu Lys

<210> SEQ ID NO 48
<211> LENGTH: 31
<212> TYPE: PRT
<213> ORGANISM: Artificial sequence
<220> FEATURE:
<223> OTHER INFORMATION: Synthetic peptide

<400> SEQUENCE: 48

Lys Asp Glu Pro Gln Arg Arg Ser Ala Arg Leu Ser Ala Lys Pro Ala
1               5                   10                  15
Pro Pro Lys Pro Glu Pro Lys Pro Lys Ala Pro Lys Lys
            20                  25                  30

<210> SEQ ID NO 49
<211> LENGTH: 5
<212> TYPE: PRT
<213> ORGANISM: Artificial sequence
<220> FEATURE:
<223> OTHER INFORMATION: Synthetic peptide

<400> SEQUENCE: 49

Cys Arg Gly Asp Lys
1               5

<210> SEQ ID NO 50
<211> LENGTH: 32
<212> TYPE: PRT
<213> ORGANISM: Artificial sequence
<220> FEATURE:
<223> OTHER INFORMATION: Synthetic peptide

<400> SEQUENCE: 50

Ser Gly Glu Glu Glu Leu Gln Leu Gln Leu Ala Leu Ala Met Ser Lys

```
1               5                   10                  15
Glu Glu Met Gly Cys Ile Lys Ser Lys Arg Lys Cys Arg Gly Asp Lys
            20                  25                  30
```

<210> SEQ ID NO 51
<211> LENGTH: 18
<212> TYPE: PRT
<213> ORGANISM: Artificial sequence
<220> FEATURE:
<223> OTHER INFORMATION: Synthetic peptide

<400> SEQUENCE: 51

```
Gln Glu Glu Glu Glu Leu Gln Leu Ala Leu Ala Leu Ser Gln Ser Glu
1               5                   10                  15
Ala Glu
```

<210> SEQ ID NO 52
<211> LENGTH: 18
<212> TYPE: PRT
<213> ORGANISM: Artificial sequence
<220> FEATURE:
<223> OTHER INFORMATION: Synthetic peptide

<400> SEQUENCE: 52

```
Ser Glu Glu Asp Met Ile Glu Trp Ala Lys Arg Glu Ser Glu Arg Glu
1               5                   10                  15
Glu Glu
```

<210> SEQ ID NO 53
<211> LENGTH: 18
<212> TYPE: PRT
<213> ORGANISM: Artificial sequence
<220> FEATURE:
<223> OTHER INFORMATION: Synthetic peptide

<400> SEQUENCE: 53

```
Gln Glu Gln Glu Asp Leu Glu Leu Ala Ile Ala Leu Ser Lys Ser Glu
1               5                   10                  15
Ile Ser
```

<210> SEQ ID NO 54
<211> LENGTH: 18
<212> TYPE: PRT
<213> ORGANISM: Artificial sequence
<220> FEATURE:
<223> OTHER INFORMATION: Synthetic peptide

<400> SEQUENCE: 54

```
Asp Glu Glu Glu Leu Ile Arg Lys Ala Ile Glu Leu Ser Leu Lys Glu
1               5                   10                  15
Ser Arg
```

<210> SEQ ID NO 55
<211> LENGTH: 18
<212> TYPE: PRT
<213> ORGANISM: Artificial sequence
<220> FEATURE:
<223> OTHER INFORMATION: Synthetic peptide

<400> SEQUENCE: 55

```
Glu Glu Asp Pro Asp Leu Lys Ala Ala Ile Gln Glu Ser Leu Arg Glu
1               5                   10                  15
Ala Glu
```

-continued

```
<210> SEQ ID NO 56
<211> LENGTH: 18
<212> TYPE: PRT
<213> ORGANISM: Artificial sequence
<220> FEATURE:
<223> OTHER INFORMATION: Synthetic peptide

<400> SEQUENCE: 56

Lys Glu Glu Glu Asp Leu Ala Lys Ala Ile Glu Leu Ser Leu Lys Glu
1               5                   10                  15

Gln Arg

<210> SEQ ID NO 57
<211> LENGTH: 18
<212> TYPE: PRT
<213> ORGANISM: Artificial sequence
<220> FEATURE:
<223> OTHER INFORMATION: Synthetic peptide

<400> SEQUENCE: 57

Lys Glu Asp Glu Asp Ile Ala Lys Ala Ile Glu Leu Ser Leu Gln Glu
1               5                   10                  15

Gln Lys

<210> SEQ ID NO 58
<211> LENGTH: 18
<212> TYPE: PRT
<213> ORGANISM: Artificial sequence
<220> FEATURE:
<223> OTHER INFORMATION: Synthetic peptide

<400> SEQUENCE: 58

Ser Gly Glu Glu Glu Leu Gln Leu Gln Leu Ala Leu Ala Met Ser Arg
1               5                   10                  15

Glu Val

<210> SEQ ID NO 59
<211> LENGTH: 15
<212> TYPE: PRT
<213> ORGANISM: Artificial sequence
<220> FEATURE:
<223> OTHER INFORMATION: Synthetic peptide

<400> SEQUENCE: 59

Glu Glu Glu Leu Ile Arg Lys Ala Ile Glu Leu Ser Leu Lys Glu
1               5                   10                  15
```